(12) United States Patent
Mazitschek et al.

(10) Patent No.: US 8,304,451 B2
(45) Date of Patent: Nov. 6, 2012

(54) HISTONE DEACETYLASE AND TUBULIN DEACETYLASE INHIBITORS

(75) Inventors: Ralph Mazitschek, Arlington, MA (US); Nicholas Paul Kwiatkowski, Auburn, MA (US); James Elliot Bradner, Cambridge, MA (US)

(73) Assignees: President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 804 days.

(21) Appl. No.: 12/299,430

(22) PCT Filed: May 2, 2007

(86) PCT No.: PCT/US2007/010587
§ 371 (c)(1),
(2), (4) Date: Mar. 26, 2009

(87) PCT Pub. No.: WO2007/130429
PCT Pub. Date: Nov. 15, 2007

(65) Prior Publication Data
US 2009/0209590 A1 Aug. 20, 2009

Related U.S. Application Data

(60) Provisional application No. 60/797,211, filed on May 3, 2006.

(51) Int. Cl.
*A61K 31/357* (2006.01)
*C07D 407/12* (2006.01)
(52) U.S. Cl. ............... 514/452; 549/370
(58) Field of Classification Search ............... 514/452; 549/369
See application file for complete search history.

(56) References Cited

U.S. PATENT DOCUMENTS

| | | | |
|---|---|---|---|
| 4,608,390 A | 8/1986 | Summers, Jr. |
| 4,631,211 A | 12/1986 | Houghten |
| 4,639,462 A | 1/1987 | Kramer et al. |
| 4,683,195 A | 7/1987 | Mullis et al. |
| 4,683,202 A | 7/1987 | Mullis |
| 4,820,828 A | 4/1989 | Demers et al. |
| 4,833,080 A | 5/1989 | Brent et al. |
| 4,861,798 A | 8/1989 | Tramposch et al. |
| 5,045,538 A | 9/1991 | Schneider et al. |
| 5,059,698 A | 10/1991 | Schulthess et al. |
| 5,096,815 A | 3/1992 | Ladner et al. |
| 5,143,854 A | 9/1992 | Pirrung et al. |
| 5,175,191 A | 12/1992 | Marks et al. |
| 5,176,996 A | 1/1993 | Hogan et al. |
| 5,198,346 A | 3/1993 | Ladner et al. |
| 5,223,409 A | 6/1993 | Ladner et al. |
| 5,225,173 A | 7/1993 | Wai |
| 5,238,781 A | 8/1993 | Schadeli |
| 5,256,775 A | 10/1993 | Froehler |
| 5,264,564 A | 11/1993 | Matteucci |
| 5,283,317 A | 2/1994 | Saifer et al. |
| 5,288,514 A | 2/1994 | Ellman |
| 5,304,121 A | 4/1994 | Sahatjian |
| 5,328,470 A | 7/1994 | Nabel et al. |
| 5,359,115 A | 10/1994 | Campbell et al. |
| 5,362,899 A | 11/1994 | Campbell |
| 5,393,741 A | 2/1995 | Pettersen et al. |
| 5,440,016 A | 8/1995 | Blondelle et al. |
| 5,480,971 A | 1/1996 | Houghten et al. |
| 5,659,016 A | 8/1997 | Nakamura et al. |
| 5,700,811 A | 12/1997 | Breslow et al. |
| 5,763,182 A | 6/1998 | Nakamura et al. |
| 5,837,313 A | 11/1998 | Ding et al. |
| 5,886,026 A | 3/1999 | Hunter et al. |
| 5,891,507 A | 4/1999 | Jayaraman |
| 6,030,945 A | 2/2000 | Ashkenazi |
| 6,068,987 A | 5/2000 | Dulski et al. |
| 6,071,305 A | 6/2000 | Brown et al. |
| 6,099,562 A | 8/2000 | Ding et al. |
| 6,153,252 A | 11/2000 | Hossainy et al. |
| 6,190,619 B1 | 2/2001 | Kilcoin et al. |
| 6,195,612 B1 | 2/2001 | Pack-Harris |
| 6,203,551 B1 | 3/2001 | Wu |

(Continued)

FOREIGN PATENT DOCUMENTS

DE 32 422 252 1/1987

(Continued)

OTHER PUBLICATIONS

Bundgaard, Design of Prodrugs, 1985, Elsevier, Chapter 1, p. 1-4.*
"Inhibitor", http://www.biology-online.org/dictionary/inhibitor, accessed Apr. 7, 2011.*
Zhu, Phosphine-Catalyzed Synthesis of 1,3-dioxan-4-ylidenes, 2005, Organic Letters, vol. 7, No. 7, p. 1387-1390.*
Extended European Search Report for EP 07872648.6 mailed Apr. 13, 2011.

(Continued)

*Primary Examiner* — Golam M M Shameem
*Assistant Examiner* — Karen Cheng
(74) *Attorney, Agent, or Firm* — Wolf, Greenfield & Sacks, P.C.; C. Hunter Baker

(57) ABSTRACT

In recognition of the need to develop novel therapeutic agents and efficient methods for the synthesis thereof, the present invention provides novel inhibitors of histone deacetylases, tubulin deacetylases, and/or aggresome inhibitors, and pharmaceutically acceptable salts and derivatives thereof. The inventive compounds fall into two classes—"isotubacin" class and "isoisotubacin" class—all of which include a 1,3-dioxane core. The present invention further provides methods for treating disorders regulated by histone deacetylase activity, tubulin deacetylase activity, and/or the aggresome (e.g., proliferative diseases, cancer, inflammatory diseases, protozoal infections, protein degradation disorders, protein deposition disorders, etc.) comprising administering a therapeutically effective amount of an inventive compound to a subject in need thereof. The present invention also provides methods for preparing compounds of the invention.

31 Claims, 16 Drawing Sheets

U.S. PATENT DOCUMENTS

| | | |
|---|---|---|
| 6,231,600 B1 | 5/2001 | Zhong |
| 6,248,127 B1 | 6/2001 | Shah et al. |
| 6,251,136 B1 | 6/2001 | Guruwaiya et al. |
| 6,258,121 B1 | 7/2001 | Yang et al. |
| 6,273,913 B1 | 8/2001 | Wright et al. |
| 6,428,960 B1 | 8/2002 | Clark et al. |
| 6,495,719 B2 | 12/2002 | Lan-Hargest et al. |
| 6,512,123 B2 | 1/2003 | Grossmann et al. |
| 6,517,889 B1 | 2/2003 | Jayaraman |
| 6,541,661 B1 | 4/2003 | Delorme et al. |
| 6,777,217 B1 | 8/2004 | Schreiber et al. |
| 6,897,220 B2 | 5/2005 | Delorme et al. |
| 6,960,685 B2 | 11/2005 | Watkins et al. |
| 7,244,853 B2 | 7/2007 | Schreiber et al. |
| 7,250,504 B2 | 7/2007 | Grozinger et al. |
| 7,994,362 B2 | 8/2011 | Schreiber et al. |
| 2001/0027340 A1 | 10/2001 | Wright et al. |
| 2003/0004209 A1 | 1/2003 | Hunter et al. |
| 2003/0129724 A1 | 7/2003 | Grozinger et al. |
| 2003/0187027 A1 | 10/2003 | Schreiber et al. |
| 2003/0216345 A1 | 11/2003 | Nakanishi et al. |
| 2004/0072849 A1 | 4/2004 | Schreiber et al. |
| 2004/0087631 A1 | 5/2004 | Bacopoulos et al. |
| 2004/0092598 A1 | 5/2004 | Watkins et al. |
| 2004/0127522 A1 | 7/2004 | Chiao et al. |
| 2004/0138153 A1 | 7/2004 | Ramesh et al. |
| 2005/0014839 A1 | 1/2005 | Kozikowski et al. |
| 2005/0267037 A1 | 12/2005 | Anderson et al. |
| 2005/0287629 A1 | 12/2005 | Grozinger et al. |
| 2006/0020131 A1 | 1/2006 | Raeppel et al. |
| 2006/0079528 A1 | 4/2006 | Finn et al. |
| 2006/0239909 A1 | 10/2006 | Anderson et al. |
| 2007/0093413 A1 | 4/2007 | Schreiber et al. |
| 2008/0269245 A1 | 10/2008 | Schreiber et al. |
| 2008/0300205 A1 | 12/2008 | Tsai et al. |
| 2009/0036318 A1 | 2/2009 | Grozinger et al. |
| 2009/0221474 A1 | 9/2009 | Schreiber et al. |
| 2009/0305384 A1 | 12/2009 | Grozinger et al. |
| 2009/0312363 A1 | 12/2009 | Bradner et al. |
| 2010/0056588 A1 | 3/2010 | Bradner et al. |
| 2010/0137196 A1 | 6/2010 | Schreiber et al. |
| 2011/0172303 A1 | 7/2011 | Tang et al. |
| 2011/0218154 A1 | 9/2011 | Schreiber et al. |

FOREIGN PATENT DOCUMENTS

| | | |
|---|---|---|
| EP | 0 259 149 A2 | 3/1988 |
| EP | 0 322 335 A1 | 6/1989 |
| EP | 0 323 590 A2 | 7/1989 |
| EP | 0 331 524 A2 | 9/1989 |
| EP | 0 458 131 A1 | 11/1991 |
| EP | 0 708 112 A1 | 4/1996 |
| GB | 2 169 599 A | 7/1986 |
| JP | 8-311321 A | 11/1996 |
| JP | 9-124918 A | 5/1997 |
| JP | 2004-043446 A | 2/2004 |
| WO | WO 90/02909 A1 | 3/1990 |
| WO | WO 91/00257 A1 | 1/1991 |
| WO | WO 91/07087 A1 | 5/1991 |
| WO | WO 92/09690 A2 | 6/1992 |
| WO | WO 92/10092 A1 | 6/1992 |
| WO | WO 92/15694 A1 | 9/1992 |
| WO | WO 93/05807 A2 | 4/1993 |
| WO | WO 93/07867 A1 | 4/1993 |
| WO | WO 93/09668 A1 | 5/1993 |
| WO | WO 93/19778 A1 | 10/1993 |
| WO | WO 93/20242 A1 | 10/1993 |
| WO | WO 94/08051 A1 | 4/1994 |
| WO | WO 94/10300 A1 | 5/1994 |
| WO | WO 97/11366 A1 | 3/1997 |
| WO | WO 97/35990 A2 | 10/1997 |
| WO | WO 98/16830 A2 | 4/1998 |
| WO | WO 98/47869 A1 | 10/1998 |
| WO | WO 98/55449 A1 | 12/1998 |
| WO | WO 00/20415 A1 | 4/2000 |
| WO | WO 00/34313 A1 | 6/2000 |
| WO | WO 00/35911 A1 | 6/2000 |
| WO | WO 00/36132 A1 | 6/2000 |
| WO | WO 00/44709 A2 | 8/2000 |
| WO | WO 02/089782 A2 | 11/2002 |
| WO | WO 04/000105 A2 | 12/2003 |
| WO | WO 04/001059 A2 | 12/2003 |
| WO | WO 2004/046104 A2 | 6/2004 |
| WO | WO 2004/062601 A2 | 7/2004 |
| WO | WO 2004/103369 A1 | 12/2004 |
| WO | WO 2005/007091 A2 | 1/2005 |
| WO | WO 2005/012247 A1 | 2/2005 |
| WO | WO 2005/018578 A2 | 3/2005 |
| WO | WO 2005/066151 A2 | 7/2005 |
| WO | WO 2005/080335 A1 | 9/2005 |
| WO | WO 2006/006080 A2 | 6/2006 |
| WO | WO 2006/060676 A1 | 6/2006 |
| WO | WO 2006/060809 A2 | 6/2006 |
| WO | WO2007/111948 * | 10/2007 |
| WO | WO 2008/040934 A1 | 4/2008 |
| WO | WO2008/091349 * | 7/2008 |
| WO | WO 2009/063054 A1 | 5/2009 |
| WO | WO 2011/019393 A2 | 2/2011 |

OTHER PUBLICATIONS

Extended European Search Report for EP 07757000.0 mailed May 3, 2011.

Office Communication, mailed Jun. 20, 2011, for U.S. Appl. No. 12/279,440.

Notice of Allowance, mailed Jun. 8, 2011, for U.S. Appl. No. 12/196,878.

Advisory Action, mailed Apr. 14, 2011, for U.S. Appl. No. 12/196,946.

Office Communication, mailed Apr. 28, 2011, for U.S. Appl. No. 12/370,390.

Notice of Allowance, mailed Aug. 17, 2011, for U.S. Appl. No. 12/370,390.

Andrews et al., Anti-malarial effect of histone deacetylation inhibitors and mammalian tumour cytodifferentiating agents. Int J Parasitol. May 2000;30(6):761-8.

Baldwin et al., Total Synthesis of Antitumor Agent At-125-(Aphas, 5S)-Alpha-Amino-3-Chloro-4,5-Isoxazoleacetic Acid. Tetrahedron. 1985;41(22):5241-60.

Bradner et al., Chemical phylogenetics of histone deacetylases. Nat Chem Biol. Mar. 2010;6(3):238-243. Epub Feb. 7, 2010.

Breslow et al., Potent cytodifferentiating agents related to hexamethylenebisacetamide. Proc Natl Acad Sci U S A. Jul. 1, 1991;88(13):5542-6.

Dankwardt et al., Solid-phase synthesis of di- and tripeptidic hydroxamic acids as inhibitors of procollagen C-proteinase. Bioorg Med Chem Lett. Nov. 20, 2000;10(22):2513-6.

Farkas et al., A comparison between the chelating properties of some dihydroxamic acids, desferrrioxamine B and acetohydroxamic acid. Polyhedron. 1999;18(1999):2391-98.

Giacomelli et al., Simple one-flask method for the preparation of hydroxamic acids. Org Lett. Jul. 24, 2003;5(15):2715-7.

Guo et al., Protein tolerance to random amino acid change. Proc Natl Acad Sci U S A. Jun. 22, 2004;101(25):9205-10. Epub Jun. 14, 2004.

Hynes, Hydroxylamine derivatives as potential antimalarial agents. 1. Hydroxamic acids. J Med Chem. Nov. 1970;13(6):1235-7.

Khomutov et al., Directed synthesis of inhibitors of enzymic changes of glutamic acid. Doklady Akademii Nauk SSSR. 1965;161(5):1227-30. Russian.

Mahboobi et al., Design of chimeric histone deacetylase- and tyrosine kinase-inhibitors: a series of imatinib hybrides as potent inhibitors of wild-type and mutant BCR-ABL, PDGF-Rbeta, and histone deacetylases. J Med Chem. Apr. 23, 2009;52(8):2265-79.

Menger et al., Chemical Reaction between Colliding Vesicles. Angew Chem Int Ed Engl. Oct. 15, 2001;40(20):3905-3907.

Munegumi et al., Amidation of carboxyl group involved in N-protected amino acids using O-benzylhydroxylamine. Peptide Chemistry. 1993;31:49-52.

Patani et al., Bioisosterism: A Rational Approach in Drug Design. Chem Rev. Dec. 19, 1996;96(8):3147-3176.

Singh et al., Chemistry and structure-activity relationship of HIV-1 integrase inhibitor integracide B and related natural products. J Nat Prod. Oct. 2003;66(10):1338-44.

Stowell et al., The synthesis of N-hydroxy-N'-phenyloctanediamide and its inhibitory effect on proliferation of AXC rat prostate cancer cells. J Med Chem. Apr. 14, 1995;38(8):1411-3.
U.S. Appl. No. 60/289,850, Schreiber et al., filed May 9, 2001.
U.S. Appl. No. 60/664,470, Bradner et al., filed Mar. 22, 2005.
U.S. Appl. No. 60/773,172, Bradner et al., filed Feb. 14, 2006.
U.S. Appl. No. 60/773,510, Bradner et al., filed Feb. 14, 2006.
International Search Report and Written Opinion for PCT/US2007/062145 mailed Jun. 24, 2008.
International Preliminary Report on Patentability for PCT/US2007/062145 mailed Aug. 28, 2008.
International Search Report and Written Opinion for PCT/US2007/062152 mailed Oct. 7, 2008.
International Search Report and Written Opinion for PCT/US2007/062152 mailed Oct. 14, 2008.
International Preliminary Report on Patentability for PCT/US2007/062152 mailed Mar. 19, 2009.
International Search Report and Written Opinion for PCT/US2006/010676 mailed Jul. 14, 2008.
International Preliminary Report on Patentability for PCT/US2006/010676 mailed Mar. 19, 2009.
Supplementary European Search Report for 06748614.2 mailed Oct. 16, 2009.
International Search Report and Written Opinion for PCT/US2007/010587 mailed Jan. 29, 2008.
International Preliminary Report on Patentability for PCT/US2007/010587 mailed Nov. 13, 2008.
International Search Report for PCT/US2002/014835 mailed Dec. 20, 2002.
Written Opinion for PCT/US2002/014835 mailed Aug. 8, 2003.
International Preliminary Exam Report for PCT/US2002/014835 mailed Jun. 4, 2004.
[No Author Listed] Targeting the aggresome with an HDAC6 inhibitor in combination with velcade for myeloma therapy. Cancer Biology and Therapy. 2005;4(7):i-iv.
Adams, The proteasome: a suitable antineoplastic target. Nat Rev Cancer. May 2004;4(5):349-60.
Aggarwal et al., Trifluoromethanesulfonic Acid, an Efficient Catalyst for the Hetero Diels-Alder Reaction and an Improved Synthesis of Mefrosol. Tetrahedron Letters. 1997;38:2569-72.
Anderson et al., Analytical Techniques in Combinatorial Chemistry: MAS CH Correlation in Solvent-Swollen Resin. J Org Chem. 1995;60:2650-51.
Antón et al., Intracellular localization of proteasomal degradation of a viral antigen. J Cell Biol. Jul. 12, 1999;146(1):113-24.
Antonjuk et al., Asymmetric Induction in the Additions of Anions of Allylic Sulfoxides to Benzaldehyde. Aust J Chem. 1980;33:2635-51.
Berge et al., Pharmaceutical salts. J Pharm Sci. Jan. 1977;66(1):1-19.
Blackwell et al., A one-bead, one-stock solution approach to chemical genetics: part 1. Chem Biol. Dec. 2001;8(12):1167-82.
Bolden et al., Anticancer activities of histone deacetylase inhibitorsNat Rev Drug Discov. Sep. 2006;5(9):769-84.
Bolger et al., Intracellular trafficking of histone deacetylase 4 regulates neuronal cell death. J Neurosci. Oct. 12, 2005;25(41):9544-53.
Bottomley et al., Structural and functional analysis of the human HDAC4 catalytic domain reveals a regulatory structural zinc-binding domain. J Biol Chem. Sep. 26, 2008;283(39):26694-704. Epub Jul. 8, 2008.
Bowers et al., Synthesis and Conformation-Activity Relationships of the Peptide Isosteres of FK228 and Largazole. J Am Chem Soc. 2009;131:2900-05.
Bowers et al., Total synthesis and biological mode of action of largazole: a potent class I histone deacetylase inhibitor. J Am Chem Soc. Aug. 20, 2008;130(33):11219-22. Epub Jul. 19, 2008.
Brummel et al., A mass spectrometric solution to the address problem of combinatorial libraries. Science. Apr. 15, 1994;264(5157):399-402.
Catley et al., NVP-LAQ824 is a potent novel histone deacetylase inhibitor with significant activity against multiple myeloma. Blood. Oct. 1, 2003;102(7):2615-22. Epub Jun, 19, 2003.
Chauhan et al., Blockade of Hsp27 overcomes Bortezomib/proteasome inhibitor PS-341 resistance in lymphoma cells. Cancer Res. Oct. 1, 2003;63(19):6174-7.

Chauhan et al., Hsp27 inhibits release of mitochondrial protein Smac in multiple myeloma cells and confers dexamethasone resistance. Blood. Nov. 1, 2003;102(9):3379-86. Epub Jul. 10, 2003.
Chu et al., Free Solution Identification of Candidate Peptides from Combinatorial Libraries by Affinity Capillary Electrophoresis/Mass Spectrometry. J Am Chem Soc. 1995;117:5419-20.
Clemons et al., A one-bead, one-stock solution approach to chemical genetics: part 2. Chem Biol. Dec. 2001;8(12):1183-95.
Cohen et al., The histone deacetylase HDAC4 connects neural activity to muscle transcriptional reprogramming. J Biol Chem. Nov. 16, 2007;282(46):33752-9. Epub Sep. 16, 2007.
Corcoran et al., A novel action of histone deacetylase inhibitors in a protein aggresome disease model. Curr Biol. Mar. 23, 2004;14(6):488-92.
Cress et al., Histone deacetylases, transcriptional control, and cancer. J Cell Physiol. Jul. 2000;184(1):1-16.
De Ruijter et al., Histone deacetylases (HDACs): characterization of the classical HDAC family. Biochem J. Mar. 15, 2003;370(Pt 3):737-49.
Denlinger et al., Proteasome inhibition sensitizes non-small cell lung cancer to histone deacetylase inhibitor-induced apoptosis through the generation of reactive oxygen species. J Thorac Cardiovasc Surg. Nov. 2004;128(5):740-8.
Dul et al., Hsp70 and antifibrillogenic peptides promote degradation and inhibit intracellular aggregation of amyloidogenic light chains. J Cell Biol. Feb. 19, 2001;152(4):705-15.
Egner et al., Solid Phase Chemistry: Direct Monitoring by Matrix-Assisted Laser Desorption/Ionization Time of Flight Mass Spectrometry. A Tool for Combinatorial Chemistry. J Org Chem. 1995;60:2652-53.
Fabian et al., A small molecule-kinase interaction map for clinical kinase inhibitors. Nat Biotechnol. Mar. 2005;23(3):329-36. Epub Feb. 13, 2005.
Fabunmi et al., Activity and regulation of the centrosome-associated proteasome. J Biol Chem. Jan. 7, 2000;275(1):409-13.
Feling et al., Salinosporamide A: a highly cytotoxic proteasome inhibitor from a novel microbial source, a marine bacterium of the new genus *Salinospora*. Angew Chem Int Ed Engl. Jan. 20, 2003;42(3):355-7.
Fitch et al., High-Resolution $^1$H NMR in Solid-Phase Organic Synthesis. J Org Chem. 1994;59:7955-56.
García-Mata et al., Characterization and dynamics of aggresome formation by a cytosolic GFP-chimera. J Cell Biol. Sep. 20, 1999;146(6):1239-54.
Garcia-Mata et al., Hassles with taking out the garbage: aggravating aggresomes. Traffic. Jun. 2002;3(6):388-96.
Gregoretti et al., Molecular evolution of the histone deacetylase family: functional implications of phylogenetic analysisJ Mol Biol. Apr. 16, 2004;338(1):17-31.
Gregory et al., Combination chemotherapy versus melphalan and prednisolone in the treatment of multiple myeloma: an overview of published trials. J Clin Oncol. Feb. 1992;10(2):334-42.
Grozinger et al., Deacetylase enzymes: biological functions and the use of small-molecule inhibitors. Chem Biol. Jan. 2002;9(1):3-16.
Grozinger et al., Three proteins define a class of human histone deacetylases related to yeast Had1p. Proc Natl Acad Sci U S A. Apr. 27, 1999;96(9):4868-73.
Haggarty et al., Domain-selective small-molecule inhibitor of histone deacetylase 6 (HDAC6)-mediated tubulin deacetylation. Proc Natl Acad Sci U S A. Apr. 15, 2003;100(8):4389-94. Epub Apr. 3, 2003.
Haggarty et al., Mapping chemical space using molecular descriptors and chemical genetics: deacetylase inhibitors. Comb Chem High Throughput Screen. Nov. 2004;7(7):669-76.
Haggarty et al., Multidimensional chemical genetic analysis of diversity-oriented synthesis-derived deacetylase inhibitors using cell-based assays. Chem Biol. May 2003;10(5):383-96.
Hassig et al., Nuclear histone acetylases and deacetylases and transcriptional regulation: HATs off to HDACs. Curr Opin Chem Biol. Oct. 1997;1(3):300-8.
Hathaway et al., Dissecting cell biology with chemical scalpels. Curr Opin Cell Biol. Feb. 2005;17(1):12-9.

Hideshima et al., Antitumor activity of lysophosphatidic acid acyltransferase-beta inhibitors, a novel class of agents, in multiple myeloma. Cancer Res. Dec. 1, 2003;63(23):8428-36.

Hideshima et al., Molecular mechanisms mediating antimyeloma activity of proteasome inhibitor PS-341. Blood. Feb. 15, 2003;101(4):1530-4. Epub Sep. 26, 2002.

Hideshima et al., Molecular mechanisms of novel therapeutic approaches for multiple myeloma. Nat Rev Cancer. Dec. 2002;2(12):927-37.

Hideshima et al., NF-κB as a therapeutic target in multiple myeloma. J Biol Chem. May 10, 2002;277(19):16639-47. Epub Feb. 28, 2002.

Hideshima et al., Novel therapeutic approaches for multiple myeloma. Immunol Rev. Aug. 2003;194:164-76.

Hideshima et al., p38 MAPK inhibition enhances PS-341 (bortezomib)-induced cytotoxicity against multiple myeloma cells. Oncogene. Nov. 18, 2004;23(54):8766-76.

Hideshima et al., Proteasome inhibitor PS-341 abrogates IL-6 triggered signaling cascades via caspase-dependent downregulation of gp130 in multiple myeloma. Oncogene. Nov. 20, 2003;22(52):8386-93.

Hideshima et al., Small-molecule inhibition of proteasome and aggresome function induces synergistic antitumor activity in multiple myeloma. Proc Natl Acad Sci U S A. Jun. 14, 2005;102(24):8567-72. Epub Jun. 3, 2005.

Hideshima et al., The proteasome inhibitor PS-341 inhibits growth, induces apoptosis, and overcomes drug resistance in human multiple myeloma cells. Cancer Res. Apr. 1, 2001;61(7):3071-6.

Hideshima et al., The role of tumor necrosis factor alpha in the pathophysiology of human multiple myeloma: therapeutic applications. Oncogene. Jul. 27, 2001;20(33):4519-27.

Hu et al., Cloning and characterization of a novel human class I histone deacetylase that functions as a transcription repressor. J Biol Chem. May 19, 2000;275(20):15254-64.

Hubbert et al., HDAC6 is a microtubule-associated deacetylase. Nature. May 23, 2002;417(6887):455-8.

Hunter et al., An Enantioselective Synthesis of Benzylidene-Protected syn-3,5-Dihydroxy Carboxylate Esters via Osmium, Palladium, and Base Catalysis. Org Letter. 2001;3(7):1049-52.

Imamoto et al., Preparation and Synthetic Use of Trimethylsilyl Polyphosphate. A New Stereoselective Aldol-Type Reaction in the Presence of Trimethylsilyl Polyphosphate. J Org Chem. 1984;49:1105-10.

Imamoto et al., The Reaction of Aryl Methyl Ketones with Aromatic Aldehydes in Trimethylsilyl Polyphosphate (PPSE). Formation of MESO-2,4,6-Trisubstituted-5-ACYL-1,3-Dioxl. Tetrahedron Letters. 1982;23(14):1467-70.

Johnston et al., Aggresomes: a cellular response to misfolded proteins. J Cell Biol. Dec. 28, 1998;143(7):1883-98.

Johnstone, Histone-deacetylase inhibitors: novel drugs for the treatment of cancer. Nat Rev Drug Discov. Apr. 2002;1(4):287-99.

Jones et al., Probing the elusive catalytic activity of vertebrate class IIa histone deacetylases. Bioorg Med Chem Lett. Mar. 15, 2008;18(6):1814-9. Epub Feb. 14, 2008.

Junn et al., Parkin accumulation in aggresomes due to proteasome impairment. J Biol Chem. Dec. 6, 2002;277(49):47870-7. Epub Oct. 2, 2002.

Kao et al., Isolation of a novel histone deacetylase reveals that class I and class II deacetylases promote SMRT-mediated repression. Genes Dev. Jan. 1, 2000;14(1):55-66.

Katoh et al., MAFFT: a novel method for rapid multiple sequence alignment based on fast Fourier transform. Nucleic Acids Res. Jul. 15, 2002;30(14):3059-66.

Kawaguchi et al., The deacetylase HDAC6 regulates aggresome formation and cell viability in response to misfolded protein stress. Cell. Dec. 12, 2003;115(6):727-38.

Kopito et al., Aggresomes and Russell bodies. Symptoms of cellular indigestion? EMBO Rep. Sep. 2000;1(3):225-31.

Kopito, Aggresomes, inclusion bodies and protein aggregation. Trends Cell Biol. Dec. 2000;10(12):524-30.

Kumar et al., MEGA: a biologist-centric software for evolutionary analysis of DNA and protein sequences. Brief Bioinform. Jul. 2008;9(4):299-306. Epub Apr. 16, 2008.

Kuruvilla et al., Dissecting glucose signaling with diversity-oriented synthesis and small-molecule microarrays. Nature. Apr. 11, 2002;416(6881):653-7.

Lahm et al., Unraveling the hidden catalytic activity of vertebrate class IIa histone deacetylases. Proc Natl Acad Sci U S A. Oct. 30, 2007;104(44):17335-40. Epub Oct. 23, 2007.

Lam et al., The "One-Bead-One-Compound" Combinatorial Library Method. Chem Rev. Apr. 1, 1997;97(2):411-448.

Lee et al., Histone acetyltransferase complexes: one size doesn't fit all. Nat Rev Mol Cell Biol. Apr. 2007;8(4):284-95.

Lee et al., Proteasome inhibitors disrupt the unfolded protein response in myeloma cells. Proc Natl Acad Sci U S A. Aug. 19, 2003;100(17):9946-51. Epub Aug. 5, 2003.

Lin et al., Generation and Aldol Reaction of Endlate Anion Adjacnet to a η3-Allyl-Mo(Co)$^2$Cp Moiety. A New Approach to the Stereoselctive Synthesis of 1,3,5-Triol and 2-Vinyl-3-Hydroxyl-Tetrahydrofuran. Tetrahedron Letters. 1990;31(52):7645-48.

Lin et al., Role of the histone deacetylase complex in acute promyelocytic leukaemia. Nature. Feb. 19, 1998;391(6669):811-4.

Look et al., Methods for Combinatorial Organic Synthesis: The Use of Fast $^{13}$C NMR Analysis for Gel Phase Reaction Monitoring. J Org Chem. 1994;59:7588-90.

Macherla et al., Structure-activity relationship studies of salinosporamide A (NPI-0052), a novel marine derived proteasome inhibitor. J Med Chem. Jun. 2, 2005;48(11):3684-7.

Maddry et al., Inhibition of the Her2 Tyrosine Kinase and Characterization of a Hydrophobic Site Near the Nucleotide Binding Domain. Bioorganic Med Chem Letter. 1997;7(16):2109-14.

Magnaghi-Jaulin et al., Retinoblastoma protein represses transcription by recruiting a histone deacetylase. Nature. Feb. 5, 1998;391(6667):601-4.

Manetto et al., Selective presence of ubiquitin in intracellular inclusions. Am J Pathol. Mar. 1989;134(3):505-13.

Marks et al., Histone deacetylases and cancer: causes and therapies. Nat Rev Cancer. Dec. 2001;1(3):194-202.

Marks et al., Histone deacetylases. Curr Opin Pharmacol. Aug. 2003;3(4):344-51.

Marmuse et al., "Click chemistry"en route to pseudo-starch. Org Biomol Chem. Jun. 21, 2005;3(12):2225-7. Epub May 11, 2005.

Marx et al., Bench to bedside: the development of rapamycin and its application to stent restenosis. Circulation. Aug. 21, 2001;104(8):852-5.

Meinke et al., Histone deacetylase: a target for antiproliferative and antiprotozoal agents. Curr Med Chem. Feb. 2001;8(2):211-35.

Meinke et al., Synthesis of apicidin-derived quinolone derivatives: parasite-selective histone deacetylase inhibitors and antiproliferative agents. J Med Chem. Dec. 14, 2000;43(25):4919-22.

Metzger et al., Ion-Spray Mass Spectrometry and High-Performance Liquid Chromatography-Mass Spectrometry of Synthetic Peptide Libraries. Angew Chem Int Ed Engl. 1993;32:894-96.

Miano et al., HDAC7 supports vascular integrity. Nat Med. Sep. 2006;12(9):997-8.

Minucci et al., Histone deacetylase inhibitors and the promise of epigenetic (and more) treatments for cancer. Nat Rev Cancer. Jan. 2006;6(1):38-51.

Mitchison, Towards a pharmacological genetics. Chem Biol. Sep. 1994;1(1):3-6.

Mitsiades et al., Inhibition of the insulin-like growth factor receptor-1 tyrosine kinase activity as a therapeutic strategy for multiple myeloma, other hematologic malignancies, and solid tumors. Cancer Cell. Mar. 2004;5(3):221-30.

Mitsiades et al., Molecular sequelae of histone deacetylase inhibition in human malignant B cells. Blood. May 15, 2003;101(10):4055-62. Epub Jan. 16, 2003.

Mitsiades et al., Molecular sequelae of proteasome inhibition in human multiple myeloma cells. Proc Natl Acad Sci U S A. Oct. 29, 2002;99(22):14374-9. Epub Oct. 21, 2002.

Mitsiades et al., Novel biologically based therapies for Waldenstrom's macroglobulinemia. Semin Oncol. Apr. 2003;30(2):309-12.

Mitsiades et al., The proteasome inhibitor PS-341 potentiates sensitivity of multiple myeloma cells to conventional chemotherapeutic agents: therapeutic applications. Blood. Mar. 15, 2003;101(6):2377-80. Epub Nov. 7, 2002.

Mitsiades et al., Transcriptional signature of histone deacetylase inhibition in multiple myeloma: biological and clinical implications. Proc Natl Acad Sci U S A. Jan. 13, 2004;101(2):540-5. Epub Dec. 26, 2003.

Mottet et al., Histone deacetylase 7 silencing alters endothelial cell migration, a key step in angiogenesis. Circ Res. Dec. 7, 2007;101(12):1237-46. Epub Oct. 18, 2007.

Myers et al., Preparation of the Chiral, C-Protected α-Amino Aldehydes of High Optical Purity and Their Use as Condensation Components in a Linear Synthesis Strategy. J Am Chem Soc. 1999;121:8401-02.

Nakatsuka et al., Total Synthesis of FK506 and an FKBP Probe Reagent, ($C_8$, $C_9$-$^{13}C_2$)-FK506. J. Am. Chem. Soc. 1990; 112: 5583-5601.

Nefzi et al., The Current Status of Heterocyclic Combinatorial Libraries. Chem Rev. Apr. 1, 1997;97(2):449-472.

Newman et al., The influence of natural products upon drug discovery. Nat Prod Rep. Jun. 2000;17(3):215-34.

Nielsen et al., Crystal structure of a bacterial class 2 histone deacetylase homologue. J Mol Biol. Nov. 18, 2005;354(1):107-20. Epub Oct. 7, 2005.

Notterpek et al., PMP22 accumulation in aggresomes: implications for CMT1A pathology. Neurobiol Dis. Oct. 1999;6(5):450-60.

O'Connor et al., Developing new drugs for the treatment of lymphoma. European Journal of Haematology. 2005;75:150-58.

Ohlmeyer et al., Complex synthetic chemical libraries indexed with molecular tags. Proc Natl Acad Sci U S A. Dec. 1, 1993;90(23):10922-6.

Parra et al., Protein kinase D1 phosphorylates HDAC7 and induces its nuclear export after T-cell receptor activation J Biol Chem. Apr. 8, 2005;280(14):13762-70. Epub Dec. 28, 2004.

Patel et al., Identification and characterization of small molecule inhibitors of a class I histone deacetylase from *Plasmodium falciparum*. J Med Chem. Apr. 23, 2009;52(8):2185-7.

Pei et al., Synergistic induction of oxidative injury and apoptosis in human multiple myeloma cells by the proteasome inhibitor bortezomib and histone deacetylase inhibitors. Clin Cancer Res. Jun. 1, 2004;10(11):3839-52.

Presbitero et al., Drug-eluting stents do they make the difference? Minerva Cardioangiol. Oct. 2002;50(5):431-42. Italian.

Pyne et al., Reactions of Lithiated N-Tosyl S-Phenyl S-2-Propenyl Sulfoximine with Aldehydes. Sulfur Letters. 1997;20(6):255-60.

Raje et al., Combination of the mTOR inhibitor rapamycin and CC-5013 has synergistic activity in multiple myeloma. Blood. Dec. 15, 2004;104(13):4188-93. Epub Aug. 19, 2004.

Renthal et al., Histone deacetylase 5 epigenetically controls behavioral adaptations to chronic emotional stimuli. Neuron. Nov. 8, 2007;56(3):517-29.

Richardson et al., A phase 2 study of bortezomib in relapsed, refractory myeloma. N Engl J Med. Jun. 26, 2003;348(26):2609-17.

Riester et al., Members of the histone deacetylase superfamily differ in substrate specificity towards small synthetic substrates. Biochem Biophys Res Commun. Nov. 19, 2004;324(3):1116-23.

Rosato et al., Histone deacetylase inhibitors in clinical development. Expert Opin Investig Drugs. Jan. 2004;13(1):21-38.

Ruygrok et al., Rapamycin in cardiovascular medicine. Intern Med J. Mar. 2003;33(3):103-9.

Saitou et al., The neighbor-joining method: a new method for reconstructing phylogenetic trees. Mol Biol Evol. Jul. 1987;4(4):406-25.

Schreiber, Chemical genetics resulting from a passion for synthetic organic chemistry. Bioorg Med Chem. Aug. 1998;6(8):1127-52.

Schreiber, Target-oriented and diversity-oriented organic synthesis in drug discovery. Science. Mar. 17, 2000;287(5460):1964-9.

Schreiber, Using the Principles of Organic Chemistry to Explore Cell Biology. Chem and Eng News. 1992; 70(43): 22-32.

Schuetz et al., Human HDAC7 harbors a class IIa histone deacetylase-specific zinc binding motif and cryptic deacetylase activity. J Biol Chem. Apr. 25, 2008;283(17):11355-63. Epub Feb. 19, 2008.

Secrist et al., HDAC inhibitors for the treatment of cancer. Curr Opin Investig Drugs. Dec. 2003;4(12):1422-7.

Serrador et al., HDAC6 deacetylase activity links the tubulin cytoskeleton with immune synapse organization. Immunity. Apr. 2004;20(4):417-28.

Smith et al., Mechanisms and molecular probes of sirtuins. Chem Biol. Oct. 20, 2008;15(10):1002-13.

Somoza et al., Structural snapshots of human HDAC8 provide insights into the class I histone deacetylases. Structure. Jul. 2004;12(7):1325-34.

Stamatakis et al., A rapid bootstrap algorithm for the RAxML Web servers. Syst Biol. Oct. 2008;57(5):758-71.

Sternson et al., Split—pool synthesis of 1,3-dioxanes leading to arrayed stock solutions of single compounds sufficient for multiple phenotypic and protein-binding assays. J Am Chem Soc. Feb. 28, 2001;123(8):1740-7.

Sternson et al., Synthesis of 7200 small molecules based on a substructural analysis of the histone deacetylase inhibitors trichostatin and trapoxin. Org Lett. Dec. 27, 2001;3(26):4239-42.

Stevanovic et al., Natural and Synthetic Peptide Pools: Characterization by Sequencing and Electrospray Mass Spectrometry. Bioorg Med Chem Lett. 1993;3(3):431-36.

Sullivan et al., Localization of the BiP molecular chaperone with respect to endoplasmic reticulum foci containing the cystic fibrosis transmembrane conductance regulator in yeast. J Histochem Cytochem. Apr. 2003;51(4):545-8.

Tallarico et al., An alkylsilyl-tethered, high-capacity solid support amenable to diversity-oriented synthesis for one-bead, one-stock solution chemical genetics. J Comb Chem. May-Jun. 2001;3(3):312-8.

Tan et al., Stereoselective Synthesis of over Two Million Compounds Having Structural Features Both Reminiscent of Natural Products and Compatible with Miniaturized Cell-Based Assays. J. Am. Chem. Soc. 1998; 120: 8565-66.

Tao et al., Deacetylase inhibition promotes the generation and function of regulatory T cells. Nat Med. Nov. 2007;13(11):1299-307. Epub Oct. 7, 2007.

Taunton et al., A mammalian histone deacetylase related to the yeast transcriptional regulator Rpd3p. Science. Apr. 19, 1996;272(5260):408-11.

Taunton et al., Synthesis of Natural and Modified Trapoxins, Useful Reagents for Exploring Histone Deacetylase Function. J Am Chem Soc. 1996;118:10412-22.

Tong et al., Chromatin deacetylation by an ATP-dependent nucleosome remodeling complex. Nature. 1997;395:917-21.

Tsankova et al., Sustained hippocampal chromatin regulation in a mouse model of depression and antidepressant action. Nat Neurosci. Apr. 2006;9(4):519-25. Epub Feb. 26, 2006.

Uchiyama et al., Adhesion of human myeloma-derived cell lines to bone marrow stromal cells stimulates interleukin-6 secretion. Blood. Dec. 15, 1993;82(12):3712-20.

Uong et al., Stereocontrolled Functionalization of Acyclic Molybdenum-$\eta^3$-Allyl Complexes: A New Approach to the Stereoselective Synthesis of 1,3-Diols. J Chem Soc Chem Commun. 1990:1285-87.

Urnov et al., Targeting of N-CoR and histone deacetylase 3 by the oncoprotein v-erbA yields a chromatin infrastructure-dependent transcriptional repression pathway. EMBO J. Aug. 1, 2000;19(15):4074-90.

Vannini et al., Crystal structure of a eukaryotic zinc-dependent histone deacetylase, human HDAC8, complexed with a hydroxamic acid inhibitor. Proc Natl Acad Sci U S A. Oct. 19, 2004;101(42):15064-9. Epub Oct. 11, 2004.

Vegas et al., Fluorous-based small-molecule microarrays for the discovery of histone deacetylase inhibitors. Angew Chem Int Ed Engl. 2007;46(42):7960-4.

Venter et al., The sequence of the human genome. Science. Feb. 16, 2001;291(5507):1304-51.

Vong et al., Regio- and Stereocontrolled Functionalization of Acyclic Molybdenum-$\eta^3$-Allyl Complexes. J Am Chem Soc. 1991;113:573-82.

Wang et al., Zinc binding in HDAC inhibitors: a DFT study. J Org Chem. Jul. 6, 2007;72(14):54469. Epub Jun. 19, 2007.

Warrell et al., Therapeutic targeting of transcription in acute promyelocytic leukemia by use of an inhibitor of histone deacetylase. J Natl Cancer Inst. Nov. 4, 1998;90(21):1621-5.

Wegener et al., A fluorogenic histone deacetylase assay well suited for high-throughput activity screening. Chem Biol. Jan. 2003;10(1):61-8.

Whelan et al., A general empirical model of protein evolution derived from multiple protein families using a maximum-likelihood approach. Mol Biol Evol. May 2001;18(5):691-9.

Wilen et al., Strategies in Optical Resolution. Tetrahedron. 1977;33:2725-36.

Wong et al., Modular synthesis and preliminary biological evaluation of stereochemically diverse 1,3-dioxanes. Chem Biol. Sep. 2004;11(9):1279-91.

Wong et al., Structural biasing elements for in-cell histone deacetylase paralog selectivity. J Am Chem Soc. May 14, 2003;125(19):5586-7.

Yang et al., Isolation and characterization of cDNAs corresponding to an additional member of the human histone deacetylase gene family. J Biol Chem. Oct. 31, 1997;272(44):28001-7.

Youngquist et al., Matrix-assisted laser desorption ionization for rapid determination of the sequences of biologically active peptides isolated from support-bound combinatorial peptide libraries. Rapid Commun Mass Spectrom. Jan. 1994;8(1):77-81.

Yu et al., The proteasome inhibitor bortezomib interacts synergistically with histone deacetylase inhibitors to induce apoptosis in Bcr/Abl+ cells sensitive and resistant to STI571. Blood. Nov. 15, 2003;102(10):3765-74. Epub Jul. 31, 2003.

Zhou et al., Cloning and characterization of a histone deacetylase, HDAC9. Proc Natl Acad Sci U S A. Sep. 11, 2001;98(19):10572-7. Epub Sep. 4, 2001.

Zhou et al., Identification of a transcriptional repressor related to the noncatalytic domain of histone deacetylases 4 and 5. Proc Natl Acad Sci U S A. Feb. 1, 2000;97(3):1056-61.

Office Communication, mailed Sep. 29, 2011, for U.S. Appl. No. 12/279,440.

Office Communication, mailed Sep. 23, 2011, for U.S. Appl. No. 13/030,086.

Tanaka et al., Syntheses and anti-inflammatory and analgesic activities of hydroxamic acids and acid hydrazides. Chem Pharm Bull (Tokyo). Aug. 1983;31(8):2810-9.

Invitation to Pay Additional Fees for PCT/US2007/062145 mailed Oct. 29, 2007.

Invitation to Pay Additional Fees for PCT/US2007/062152 mailed Dec. 7, 2007.

International Preliminary Report on Patentability for PCT/US2009/004235 mailed Feb. 3, 2011.

Invitation to Pay Additional Fees for PCT/US1997/005275 mailed Nov. 21, 1997.

International Search Report for PCT/US1997/005275 mailed Feb. 16, 1998.

Written Opinion for PCT/US1997/005275 mailed Mar. 5, 1998.

International Preliminary Examination Report for PCT/US1997/005275 mailed Jul. 3, 1998.

Office Communication, mailed Oct. 15, 2008, for U.S. Appl. No. 11/386,959.

Office Communication, mailed Jul. 21, 2009, for U.S. Appl. No. 11/386,959.

Office Communication, mailed Nov. 17, 2009, for U.S. Appl. No. 11/386,959.

Office Communication, mailed Nov. 28, 2005, for U.S. Appl. No. 10/621,276.

Office Communication, mailed Aug. 8, 2006, for U.S. Appl. No. 10/621,276.

Notice of Allowance, mailed Mar. 6, 2007, for U.S. Appl. No. 10/621,276.

Office Communication, mailed Sep. 16, 2009, for U.S. Appl. No. 11/879,466.

Notice of Allowance, mailed Feb. 4, 2010, for U.S. Appl. No. 11/879,466.

Office Communication, mailed Jan. 21, 1998, for U.S. Appl. No. 08/624,735.

Office Communication, mailed Jan. 17, 2001, for U.S. Appl. No. 08/624,735.

Office Communication, mailed Oct. 10, 2001, for U.S. Appl. No. 08/624,735.

Office Communication, mailed Oct. 16, 2002, for U.S. Appl. No. 08/624,735.

Office Communication, mailed Aug. 12, 2003, for U.S. Appl. No. 08/624,735.

Notice of Allowance, mailed Apr. 13, 2004, for U.S. Appl. No. 08/624,735.

Office Communication, mailed May 6, 2009, for U.S. Appl. No. 10/919,217.

Office Communication, mailed Mar. 4, 2010, for U.S. Appl. No. 10/919,217.

Office Communication, mailed Oct. 14, 2010, for U.S. Appl. No. 10/919,217.

Office Communication, mailed Apr. 8, 2010, for U.S. Appl. No. 12/196,878.

Office Communication, mailed Aug. 10, 2010, for U.S. Appl. No. 12/196,878.

Office Communication, mailed Jan. 18, 2011, for U.S. Appl. No. 12/196,878.

Office Communication, mailed Aug. 5, 2010, for U.S. Appl. No. 12/196,946.

Office Communication, mailed Dec. 28, 2010, for U.S. Appl. No. 12/196,946.

Office Communication, mailed Jun. 30, 2003, for U.S. Appl. No. 09/800,187.

Office Communication, mailed Apr. 13, 2004, for U.S. Appl. No. 09/800,187.

Notice of Allowance, mailed Apr. 13, 2007, for U.S. Appl. No. 10/964,313.

Office Communication, mailed Sep. 17, 2009, for U.S. Appl. No. 11/831,303.

Office Communication, mailed Apr. 2, 2010, for U.S. Appl. No. 12/370,390.

Office Communication, mailed Oct. 8, 2010, for U.S. Appl. No. 12/370,390.

Genbank Submission: NIH/NCBI, Accession No. AAA68286; GI: 348052, Henkin et al., Jun. 14, 1995.

Genbank Submission: NIH/NCBI, Accession No. AAF73428, Buggy et al.; Jun. 1, 2000.

Genbank Submission: NIH/NCBI, Accession No. AAP63491; Kieliszewski; Jun. 12, 2003.

Genbank Submission; NIH/NCBI, Accession No. AB006626; GI:6635126, Ohara et al.; Dec. 25, 1999.

Genbank Submission; NIH/NCBI, Accession No. AB006626; GI:2564323, Ohara et al.; Mar. 18, 1998.

Genbank Submission; NIH/NCBI, Accession No. AF039241, Swensen.; Mar. 11, 2009.

Genbank Submission; NIH/NCBI, Accession No. AF132607, Grozinger et al.; May 6, 1999.

Genbank Submission; NIH/NCBI, Accession No. AF230097, Hu et al., May 31, 2000.

Genbank Submission; NIH/NCBI, Accession No. AF245664, Buggy et al.; Jun. 1, 2000.

Genbank Submission; NIH/NCBI, Accession No. AJ011972, Strom et al.; Oct. 19, 1998.

Genbank Submission: NIH/NCBI, Accession No. BAA25526; GI: 3043724, Ohara et al., Apr. 10, 1998.

Genbank Submission: NIH/NCBI, Accession No. BC009676, Strausberg et al.; Jul. 15, 2006.

Genbank Submission: NIH/NCBI, Accession No. BC111735, Strausberg et al.; Jan. 17, 2006.

Genbank Submission; NIH/NCBI, Accession No. CAA09893.1, Strom et al.; Oct. 7, 2008.

Genbank Submission; NIH/NCBI, Accession No. NM_006044.2, Dhakal et al.; Mar. 15, 2009.

Genbank Submission; NIH/NCBI, Accession No. NM_001015053.1, Seo et al.; Mar. 15, 2009.

Genbank Submission; NIH/NCBI, Accession No. NM_006037.3, Chabane et al.; Mar. 29, 2009.

Genbank Submission; NIH/NCBI, Accession No. NM_014707, Muralidhar et al.; Mar. 11, 2011.
Genbank Submission; NIH/NCBI, Accession No. NM_018486, Bailey et al.; Mar. 11, 2011.
Genbank Submission; NIH/NCBI, Accession No. NM_032019, Bailey et al.; Mar. 12, 2011.
Genbank Submission; NIH/NCBI, Accession No. NM_058176, Muralidhar et al.; Feb. 27, 2011.
Genbank Submission; NIH/NCBI, Accession No. NM_058177, Tam et al.; May 7, 2010.
Genbank Submission; NIH/NCBI, Accession No. NM_178423, Muralidhar et al.; Mar. 13, 2011.
Genbank Submission; NIH/NCBI, Accession No. NM_178425, Muralidhar et al.; Feb. 27, 2011.
Genbank Submission; NIH/NCBI, Accession No. NP_001518, Campos et al.; Mar. 13, 2011.
Genbank Submission; NIH/NCBI, Accession No. NP_004955, Dong et al; Mar. 27, 2011.
Genbank Submission; NIH/NCBI, Accession No. NP_005465, Huynh; Mar. 11, 2011.
Genbank Submission; NIH/NCBI, Accession No. NP_006035; Aldana-Masangkay et al.; Mar. 13, 2011.
Genbank Submission; NIH/NCBI, Accession No. O15739, Loomis et al.; Oct. 31, 2006.
Genbank Submission: NIH/NCBI, Accession No. P56524; GI: 3024889, Ohara et al., Dec. 15, 1998.
Genbank Submission: NIH/NCBI, Accession No. Q48935; GI: 3023317, Sakurada et al., Apr. 20, 2010.
Genbank Submission; NIH/NCBI, Accession No. Q9Z2V5, Verdel et al.; Mar. 2, 2010.
Genbank Submission; NIH/NCBI, Accession No. Q9Z2V6, Verdel et al.; Mar. 2, 2010.
Genbank Submission; NIH/NCBI, Accession No. R64669, Wilson; May 26, 1995.
Genbank Submission; NIH/NCBI, Accession No. U31814, Yang et al.; Nov. 13, 1996.
Genbank Submission; NIH/NCBI, Accession No. U31814, Yang et al.; Nov. 14, 1996.
NCBI annotation project, GenBank Accession Number, XM_002252, Oct. 16, 2001.
NCBI annotation project, GenBank Accession Number, XM_004963, Feb. 9, 2001.
NCBI annotation project, GenBank Accession Number, XM_004963.2, Oct. 16, 2001.
NCBI annotation project, GenBank Accession Number, XM_007047, Nov. 16, 2000.
NCBI annotation project, GenBank Accession Number, XM_008359, Oct. 16, 2001.
NCBI annotation project, GenBank Accession Number, XP_002252, Oct. 16, 2001.
NCBI annotation project, GenBank Accession Number, XP_008359.2, Feb. 10, 2001.
Abremski et al., Bacteriophage P1 site-specific recombination. Purification and properties of the Cre recombinase protein. J Biol Chem. Feb. 10, 1984;259(3):1509-14.
Adams et al., Initial assessment of human gene diversity and expression patterns based upon 83 million nucleotides of cDNA sequence. Nature. Sep. 28, 1995;377(6547 Suppl):3-174.
Afshar et al., Characterization of a human gene with sequence homology to *Saccharomyces cerevisiae* SIR2. Gene. Jun. 24, 1999;234(1):161-8.
Ahringer, NuRD and SIN3 histone deacetylase complexes in development. Trends Genet. Aug. 2000;16(8):351-6.
Alonso et al., A novel yeast histone deacetylase: partial characterization and development of an activity assay. Biochim Biophys Acta. Mar. 26, 1986;866(2-3):161-9.
Anklesaria et al., Engraftment of a clonal bone marrow stromal cell line in vivo stimulates hematopoietic recovery from total body irradiation. Proc Natl Acad Sci U S A. Nov. 1987;84(21):7681-5.
Aparicio et al., Modifiers of position effect are shared between telomeric and silent mating-type loci in *S. cerevisiae*. Cell. Sep. 20, 1991;66(6):1279-87.
Arkin et al., An algorithm for protein engineering: simulations of recursive ensemble mutagenesis. Proc Natl Acad Sci U S A. Aug. 15, 1992;89(16):7811-5.
Auffray et al., [IMAGE: molecular integration of the analysis of the human genome and its expression.] C R Acad Sci III. Feb. 1995;318(2):263-72. French.
Baer et al., Eukaryotic RNA polymerase II binds to nucleosome cores from transcribed genes. Nature. Feb. 10, 1983;301(5900):482-8.
Ballestar et al., Methyl-CpG-binding proteins. Targeting specific gene repression. Eur J Biochem. Jan. 2001;268(1):1-6.
Barbas et al., Semisynthetic combinatorial antibody libraries: a chemical solution to the diversity problem. Proc Natl Acad Sci U S A. May 15, 1992;89(10):4457-61.
Bartel et al., Elimination of false positives that arise in using the two-hybrid system. Biotechniques. Jun. 1993;14(6):920-4.
Beck-Sickinger et al., Neuropeptide Y: identification of the binding site. Int J Pept Protein Res. Dec. 1990;36(6):522-30.
Beck-Sickinger et al., Semiautomated T-bag peptide synthesis using 9-fluorenyl-methoxycarbonyl strategy and benzotriazol-1-yl-tetramethyl-uronium tetrafluoroborate activation. Pept'Res. Mar.-Apr. 1991;4(2):88-94.
Beck-Sickinger et al., Structure/activity relationships of C-terminal neuropeptide Y peptide segments and analogues composed of sequence 1-4 linked to 25-36. Eur J Biochem. Dec. 12, 1990;194(2):449-56.
Ben-Bassat et al., Processing of the initiation methionine from proteins: properties of the *Escherichia coli* methionine aminopeptidase and its gene structure. J Bacteriol. Feb. 1987; 169(2):751-7.
Berg et al., Long-Chain Polystyrene-Grafted Polyethylene Film Matrix: A New Support for Solid-Phase Peptide Synthesis. J Am Chem Soc. 1989;111:8024-26.
Bernstein et al., Genomewide studies of histone deacetylase function in yeast. Proc Natl Acad Sci U S A. Dec. 5, 2000;97(25):13708-13.
Blankemeyer-Menge et al., Simultaneous Multiple Synthesis of Protected Peptide Fragments on "Allyl"—Functionalized Cellulose Disc Supports. Tetrahedron Lett. 1988;29:5871-74.
Blondelle et al., Soluble combinatorial libraries of organic, peptidomimetic and peptide diversities. Trends Anal Chem. 1995;14:83-92.
Borchardt et al., Synthetic Receptor Binding Elucidated with an Encoded Combinatorial Library. J Am Chem Soc. 1994;116:373-74.
Bowdish et al., Analysis of RIM11, a yeast protein kinase that phosphorylates the meiotic activator IME1. Mol Cell Biol. Dec. 1994;14(12):7909-19.
Bowdish et al., Bipartite structure of an early meiotic upstream activation sequence from *Saccharomyces cerevisiae*. Mol Cell Biol. Apr. 1993;13(4):2172-81.
Brachman et al., The SIR2 gene family, conserved from bacteria to humans, functions in silencing, cell cycle progression, and chromosome stability. Genes Dev. Dec. 1, 1995;9(23):2888-902.
Branden et al., Chapter 16. Prediction, Engineering, and Design of Protein Structures. In: Introduction to Protein Structure. Garland Publishing Inc., New York. 1991:247.
Braunstein et al., Efficient transcriptional silencing in *Saccharomyces cerevisiae* requires a heterochromatin histone acetylation pattern. Mol Cell Biol. Aug. 1996;16(8):4349-56.
Braunstein et al., Transcriptional silencing in yeast is associated with reduced nucleosome acetylation. Genes Dev. Apr. 1993;7(4):592-604.
Bray et al., Gas Phase Cleavage of Peptides from a Solid Support with Ammonia Vapour. Application in Simultaneous Multiple Peptide Synthesis. Tetrahedron Lett. 1991;32:6163-66.
Bray et al., The Simultaneous Multiple Production of Solution Phase Peptides; Assessment of the Geysen Method of Simultaneous Peptide Synthesis. Tetrahedron Lett. 1990;31:5811-14.
Brenner et al., Encoded combinatorial chemistry. Proc Natl Acad Sci U S A. Jun. 15, 1992;89(12):5381-3.
Brinster et al., Factors affecting the efficiency of introducing foreign DNA into mice by microinjecting eggs. Proc Natl Acad Sci U S A. Jul. 1985;82(13):4438-42.
Brownell et al., Tetrahymena histone acetyltransferase A: a homolog to yeast Gcn5p linking histone acetylation to gene activation. Cell. Mar. 22, 1996;84(6):843-51.

Brunet et al., Nuclear translocation of p42/p44 mitogen-activated protein kinase is required for growth factor-induced gene expression and cell cycle entry. EMBO J. Feb. 1, 1999;18(3):664-74.

Buiting et al., Detection of aberrant DNA methylation in unique Prader-Willi syndrome patients and its diagnostic implications. Hum Mol Genet. Jun. 1994;3(6):893-5.

Burbaum et al., A paradigm for drug discovery employing encoded combinatorial libraries. Proc Natl Acad Sci U S A. Jun. 20, 1995;92(13):6027-31.

Burbelo et al., 14-3-3 proteins. Hot Numbers in signal transduction. Curr Biol. Feb. 1, 1995;5(2):95-6.

Byrd et al., Depsipeptide (FR901228): a novel therapeutic agent with selective, in vitro activity against human B-cell chronic lymphocytic leukemia cells. Blood. Aug. 15, 1999;94(4):1401-8.

Calí et al., Nucleotide sequence of a cDNA encoding the human muscle-specific enolase (MSE). Nucleic Acids Res. Apr. 11, 1990;18(7):1893.

Cameron, Recent advances in transgenic technology. Mol Biotechnol. Jun. 1997;7(3):253-65.

Carmen et al., HDA1 and HDA3 are components of a yeast histone deacetylase (HDA) complex. J Biol Chem. Jun. 28, 1996;271(26):15837-44.

Cavenee et al., Expression of recessive alleles by chromosomal mechanisms in retinoblastoma. Nature. Oct. 27-Nov. 2, 1983;305(5937):779-84.

Chen et al., "Analogous" Organic Synthesis of Small-Compound Libraries: Validation of Combinatorial Chemistry in Small-Molecule Synthesis. JACS. 1994;116:2661-62.

Chen et al., Gene therapy for brain tumors: regression of experimental gliomas by adenovirus-mediated gene transfer in vivo. Proc Natl Acad Sci U S A. Apr. 12, 1994;91(8):3054-7.

Clackson et al., Making antibody fragments using phage display libraries. Nature. Aug. 15, 1991;352(6336):624-8.

Clipstone et al., Identification of calcineurin as a key signalling enzyme in T-lymphocyte activation. Nature. Jun. 25, 1991;357(6380):695-7.

Cockell et al., Nuclear compartments and gene regulation. Curr Opin Genet Dev. Apr. 1999;9(2):199-205.

Csordas, On the biological role of histone acetylation. Biochem J. Jan. 1, 1990;265(1):23-38.

Cuperus et al., Locus specificity determinants in the multifunctional yeast silencing protein Sir2. EMBO J. Jun. 1, 2000;19(11):2641-51.

Curtin et al., Succinimide hydroxamic acids as potent inhibitors of histone deacetylase (HDAC). Bioorg Med Chem Lett. Oct. 21, 2002;12(20):2919-23.

Cwirla et al., Peptides on phage: a vast library of peptides for identifying ligands. Proc Natl Acad Sci U S A. Aug. 1990;87(16):6378-82.

Dangond et al., Differential display cloning of a novel human histone deacetylase (HDAC3) cDNA from PHA-activated immune cells. Biochem Biophys Res Commun. Jan. 26, 1998;242(3):648-52.

Dann et al., Human renin: A new class of inhibitors. Biochem Biophys Res Commun. Jan. 14, 1986;134(1):71-7.

David et al., Histone deacetylase associated with mSin3A mediates repression by the acute promyelocytic leukemia-associated PLZF protein. Oncogene. May 14, 1998;16(19):2549-56.

Davie et al., Multiple functions of dynamic histone acetylation. J Cell Biochem. May 1994;55(1):98-105.

Delgrave et al., Recursive ensemble mutagenesis. Protein Engineer. 1993;6(3):327-31.

Dev et al., Electrochemotherapy—a novel method of cancer treatment. Cancer Treat Rev. Jan. 1994;20(1):105-15.

Devlin et al., Random peptide libraries: a source of specific protein binding molecules. Science. Jul. 27, 1990;249(4967):404-6.

Dower et al., Chapter 28. The Search for Molecular Diversity (II): Recombinant and Synthetic Randomized Peptide Libraries. Annu Rep Med Chem. 1991;26:271-80.

Eichler et al., Application of Cellulose Paper as Support Material in Simultaneous Solid Phase Peptide Synthesis. Collect Czech Chem Commun 1989;54:1746-52.

Eichler et al., Evaluation of cotton as a carrier for solid-phase peptide synthesis. Pept Res. Sep.-Oct. 1991;4(5):296-307.

Ellison et al., Epitope-tagged ubiquitin. A new probe for analyzing ubiquitin function. J Biol Chem. Nov. 5, 1991;266(30:21150-7.

Emiliani et al., Characterization of a human RPD3 ortholog, HDAC3. Proc Natl Acad Sci U S A. Mar. 17, 1998;95(6):2795-800.

Evans et al., An engineered poliovirus chimaera elicits broadly reactive HIV-1 neutralizing antibodies. Nature. Jun. 1, 1989;339(6223):385-8.

Evans et al., Establishment in culture of pluripotential cells from mouse embryos. Nature. Jul. 9, 1981;292(5819):154-6.

Ewenson et al., Ketomethylene pseudopeptide analogues of substance P: synthesis and biological activity. J Med Chem. Feb. 1986;29(2):295-9.

Felsenfeld, Chromatin as an essential part of the transcriptional mechanism. Nature. Jan. 16, 1992;355(6357):219-24.

Feng et al., Progressive sequence alignment as a prerequisite to correct phylogenetic trees. J Mol Evol. 1987;25(4):351-60.

Finnin et al., Structures of a histone deacetylase homologue bound to the TSA and SAHA inhibitors. Nature. Sep. 9, 1999;401(6749):188-93.

Fischle et al., A new family of human histone deacetylases related to *Saccharomyces cerevisiae* HDA1p. J Biol Chem. Apr. 23, 1999;274(17):11713-20.

Fitch, Distinguishing Homologous from Analogous Proteins. Syst Zool. 1970;19:99-113.

Fleming et al., The total synthesis of ( )-trichostatin A: Some observations on the acylation and alkylation of silyl enol ethers, silyl dienol ethers and a silyl trienol ether. Tetrahedron. 1983;39:841-46.

Fodor et al., Light-directed, spatially addressable parallel chemical synthesis. Science. Feb. 15, 1991;251(4995):767-73.

Frank et al., Simultaneous Multiple Peptide Synthesis Under Continuous Flow Conditions on Cellulose Paper Discs as Segmental Solid Supports. Tetrahedron. 1988;44:6031-40.

Frank et al., Spot-Synthesis: An Easy Technique for the Positionally Addressable, Parallel Chemical Synthesis on a Membrane Support. Tetrahedron. 1992;48:9217-32.

Frank et al., Strategies and Techniques in Simultaneous Solid Phase Synthesis Based on the Segmentation of Membrane Type Supports. Bioorg Med Chem Lett. 1993;3:425-30.

Friend et al., Deletions of a DNA sequence in retinoblastomas and mesenchymal tumors: organization of the sequence and its encoded protein. Proc Natl Acad Sci U S A. Dec. 1987;84(24):9059-63.

Frye et al., Characterization of Five Human cDNAs with Homology to the Yeast SIR2 Gene: Sir2-like Proteins (Sirtuins) Metabolize NAD and May Have Protein ADP-Ribosyltransferase Activity. Biochem Biophys Res Commun. 1999;260:273-79.

Frye, Phylogenetic classification of prokaryotic and eukaryotic Sir2-like proteins. Biochem Biophys Res Commun. Jul. 5, 2000;273(2):793-8.

Furukawa et al., Isolation and mapping of a human gene (RPD3L1) that is homologous to RPD3, a transcription factor in *Saccharomyces cerevisiae*. Cytogenet Cell Genet. 1996;73(1-2):130-3.

Furumai et al., Potent histone deacetylase inhibitors built from trichostatin A and cyclic tetrapeptide antibiotics including trapoxin. Proc Natl Acad Sci U S A. Jan. 2, 2001;98(1):87-92.

Gallop et al., Applications of combinatorial technologies to drug discovery. 1. Background and peptide combinatorial libraries. J Med Chem. Apr. 29, 1994;37(9):1233-51.

Gammon et al., T cell determinant structure: cores and determinant envelopes in three mouse major histocompatibility complex haplotypes. J Exp Med. Mar. 1, 1991;173(3):609-17.

Garcia-Ramirez et al., Role of the histone "tails" in the folding of oligonucleosomes depleted of histone H1. J Biol Chem. Sep. 25, 1992;267(27):19587-95.

Gardlik et al., Vectors and delivery systems in gene therapy. Med Sci Monit. Apr. 2005;11(4):RA110-21. Epub Mar. 24, 2005.

Gartenberg, The Sir proteins of *Saccharomyces cerevisiae*: mediators of transcriptional silencing and much more. Curr Opin Microbiol. Apr. 2000;3(2):132-7.

Gelmetti et al., Aberrant recruitment of the nuclear receptor corepressor-histone deacetylase complex by the acute myeloid leukemia fusion partner ETO. Mol Cell Biol. Dec. 1998;18(12):7185-91.

Geysen et al., Use of peptide synthesis to probe viral antigens for epitopes to a resolution of a single amino acid. Proc Natl Acad Sci U S A. Jul. 1984;81(13):3998-4002.

Gordon et al., Applications of combinatorial technologies to drug discovery. 2. Combinatorial organic synthesis, library screening strategies, and future directions. J Med Chem. May 13, 1994;37(10):1385-401.

Gordon et al., Design of peptide derived amino alcohols as transition-state analog inhibitors of angiotensin converting enzyme. Biochem Biophys Res Commun. Jan. 16, 1985;126(1):419-26.

Görlich, Nuclear protein import. Curr Opin Cell Biol. Jun. 1997;9(3):412-9.

Gossler et al., Transgenesis by means of blastocyst-derived embryonic stem cell lines. Proc Natl Acad Sci U S A. Dec. 1986;83(23):9065-9.

Gray et al., The human histone deacetylase family. Exp Cell Res. Jan. 15, 2001;262(2):75-83.

Green et al., When the products of oncogenes and anti-oncogenes meet. Cell. Jan. 13, 1989;56(1):1-3.

Griffiths et al., Human anti-self antibodies with high specificity from phage display libraries. EMBO J. Feb. 1993;12(2):725-34.

Grignani et al., Fusion proteins of the retinoic acid receptor-alpha recruit histone deacetylase in promyelocytic leukaemia. Nature. Feb. 19, 1998;391(6669):815-8.

Grozinger et al., Regulation of histone deacetylase 4 and 5 and transcriptional activity by 14-3-3-dependent cellular localization. Proc Natl Acad Sci U S A. Jul. 5, 2000;97(14):7835-40.

Grunstein, Histone acetylation in chromatin structure and transcription. Nature. Sep. 25, 1997;389(6649):349-52.

Grunstein, Molecular model for telomeric heterochromatin in yeast. Curr Opin Cell Biol. Jun. 1997;9(3):383-7.

Gu et al., Activation of p53 sequence-specific DNA binding by acetylation of the p53 C-terminal domain. Cell. Aug. 22, 1997;90(4):595-606.

Guarente, Sir2 links chromatin silencing, metabolism, and aging. Genes Dev. May 1, 2000;14(9):1021-6.

Habig et al., Glutathione S-transferases. The first enzymatic step in mercapturic acid formation. J Biol Chem. Nov. 25, 1974;249(22):7130-9.

Haggarty et al., Dissecting cellular processes using small molecules: identification of colchicine-like, taxol-like and other small molecules that perturb mitosis. Chem Biol. Apr. 2000;7(4):275-86.

Hansen et al., Retinoblastoma and the progression of tumor genetics. Trends Genet. May 1998;4(5):125-8.

Hardwick et al., Rapamycin-modulated transcription defines the subset of nutrient-sensitive signaling pathways directly controlled by the Tor proteins. Proc Natl Acad Sci U S A. Dec. 21, 1999;96(26):14866-70.

Hassig et al., A role for histone deacetylase activity in HDAC1-mediated transcriptional repression. Proc Natl Acad Sci U S A. Mar. 31, 1998;95(7):3519-24.

Hassig et al., Histone deacetylase activity is required for full transcriptional repression by mSin3A. Cell. May 2, 1997;89(3):341-7.

Hay et al., Histone deacetylase. Association with a nuclease resistant, high molecular weight fraction of HeLa cell chromatin. J Biol Chem. Mar. 25, 1983;258(6):3726-34.

Hayes et al., Histones H2A/H2B inhibit the interaction of transcription factor IIIA with the *Xenopus borealis* somatic 5S RNA gene in a nucleosome. Proc Natl Acad Sci U S A. Feb. 15, 1992;89(4):1229-33.

He et al., Distinct interactions of PML-RARalpha and PLZF-RARalpha with co-repressors determine differential responses to RA in APL. Nat Genet. Feb. 1998;18(2):126-35.

Hecht et al., Histone H3 and H4 N-termini interact with SIR3 and SIR4 proteins: a molecular model for the formation of heterochromatin in yeast. Cell. Feb. 24, 1995;80(4):583-92.

Hicks et al., Protein import into the nucleus: an integrated view. Annu Rev Cell Dev Biol. 1995;11:155-88.

Hochuli et al., New metal chelate adsorbent selective for proteins and peptides containing neighbouring histidine residues. J Chromatogr. Dec. 18, 1987;411:177-84.

Houdebine, The methods to generate transgenic animals and to control transgene expression. J Biotechnol. Sep. 25, 2002;98(2-3):145-60.

Houghten et al., Simplified procedure for carrying out simultaneous multiple hydrogen fluoride cleavages of protected peptide resins. Int J Pept Protein Res. Jun. 1986;27(6):673-8.

Houghten, General method for the rapid solid-phase synthesis of large numbers of peptides: specificity of antigen-antibody interaction at the level of individual amino acids. Proc Natl Acad Sci U S A. Aug. 1985;82(15):5131-5.

Huang et al., Nuclear receptor corepressors partner with class II histone deacetylases in a Sin3-independent repression pathway. Genes Dev. Jan. 1, 2000;14(1):45-54.

Huang et al., *Vaccinia virus* recombinants expressing an 11-kilodalton beta-galactosidase fusion protein incorporate active beta-galactosidase in virus particles. J Virol. Oct. 1988;62(10):3855-61.

Ike et al., Solid phase synthesis of polynucleotides. VIII. Synthesis of mixed oligodeoxyribonucleotides by the phosphotriester solid phase method. Nucleic Acids Res. Jan. 25, 1983;11(2):477-88.

Imai et al., Transcriptional silencing and longevity protein Sir2 is an NAD-dependent histone deacetylase. Nature. Feb. 17, 2000;403(6771):795-800.

Imhof et al., Acetylation of general transcription factors by histone acetyltransferases. Curr Biol. Sep. 1, 1997;7(9):689-92.

Itakura et al., Expression in *Escherichia coli* of a Chemically Synthesized Gene for the Hormone Somatostatin. Science. 1984;198:1056-63.

Itakura et al., Synthesis and use of synthetic oligonucleotides. Annu Rev Biochem. 1984;53:323-56.

Iwabuchi et al., Use of the two-hybrid system to identify the domain of p53 involved in oligomerization. Oncogene. Jun. 1993;8(6):1693-6.

Jacobs et al., Combinatorial chemistry—applications of light-directed chemical synthesis. Trends Biotechnol. Jan. 1994;12(1):19-26.

Jaenisch, Germ line integration and Mendelian transmission of the exogenous Moloney leukemia virus. Proc Natl Acad Sci U S A. Apr. 1976;73(4):1260-4.

Jaenisch, Transgenic animals. Science. Jun. 10, 1988;240(4858):1468-74.

Jähner et al., De novo methylation and expression of retroviral genomes during mouse embryogenesis. Nature. Aug. 12, 1982;298(5875):623-8.

Jähner et al., Insertion of the bacterial gpt gene into the germ line of mice by retroviral infection. Proc Natl Acad Sci U S A. Oct. 1985;82(20):6927-31.

Janknecht et al., Rapid and efficient purification of native histidine-tagged protein expressed by recombinant *Vaccinia virus*. Proc Natl Acad Sci U S A. Oct. 15, 1991;88(20):8972-6.

Jin et al., Transcriptional regulation of the MDR1 gene by histone acetyltransferase and deacetylase is mediated by NF-Y. Mol Cell Biol. Jul. 1998;18(7):4377-84.

Johnson et al., Deacetylase activity associates with topoisomerase II and is necessary for etoposide-induced apoptosis. J Biol Chem. Feb. 16, 2001;276(7):4539-42. Epub Jan. 2, 2001.

Johnson et al., Genetic evidence for an interaction between SIR3 and histone H4 in the repression of the silent mating loci in *Saccharomyces cerevisiae*. Proc Natl Acad Sci U S A. Aug. 1990;87(16):6286-90.

Johnson et al., Molecular cloning of *Drosophila melanogaster* cDNAs that encode a novel histone deacetylase dHDAC3. Gene. Oct. 9, 1998;221(1):127-34.

Jung et al., Amide analogues of trichostatin A as inhibitors of histone deacetylase and inducers of terminal cell differentiation. J Med Chem. Nov. 4, 1999;42(22):4669-79.

Kappel et al., Regulating gene expression in transgenic animals. Curr Opin Biotechnol. Oct. 1992;3(5):548-53.

Kennedy et al., Redistribution of silencing proteins from telomeres to the nucleolus is associated with extension of life span in *S. cerevisiae*. Cell. May 2, 1997;89(3):381-91.

Kerr et al., Encoded Combinatorial Peptide Libraries Containing Non-Natural Amino Acids. J Am Chem, Soc. 1993;115:2529-31.

Khockbin et al., Functional significance of histone deacetylase diversity. Curr Opin Genet Dev. Apr. 2001;11(2):162-6.

Kijima et al., Trapoxin, an antitumor cyclic tetrapeptide, is an irreversible inhibitor of mammalian histone deacetylase. J Biol Chem. Oct. 25, 1993;268(30):22429-35.

Kikuchi et al., Multiplicity of histone deacetylase from calf thymus. FEBS Lett. Feb. 1, 1973;29(3):280-282.

Kleff et al., Identification of a gene encoding a yeast histone H4 acetyltransferase. J Biol Chem. Oct. 20, 1995;270(42):24674-7.

Koeller et al., Chemical genetic modifier screens: small molecule trichostatin suppressors as probes of intracellular histone and tubulin acetylation. Chem Biol. May 2003;10(5):397-410.

Kohler et al., Continuous cultures of fused cells secreting antibody of predefined specificity. Nature. Aug. 7, 1975;256(5517):495-7.

Kouzarides, Acetylation: a regulatory modification to rival phosphorylation? EMBO J. Mar. 15, 2000;19(6)1176-9.

Kozbar et al., The production of monoclonal antibodies from human lymphocytes. Immunology Today. 1983;4:72-79.

Krieger et al., Chemical studies of histone acetylation. Substrate specificity of a histone deacetylase from calf thymus nuclei. J Biol Chem. Jan. 10, 1974;249(1):332-4.

Kwon et al., Depudecin induces morphological reversion of transformed fibroblasts via the inhibition of histone deacetylase. Proc Natl Acad Sci U S A. Mar. 31, 1998;95(7):3356-61.

Landegren et al., A ligase-mediated gene detection technique. Science. Aug. 26, 1988;241(4869):1077-80.

Landry et al., The silencing protein SIR2 and its homologs are NAD-dependent protein deacetylases. Proc Natl Acad Sci U S A. May 23, 2000;97(11):5807-11.

Lasko et al., Targeted oncogene activation by site-specific recombination in transgenic mice. Proc Natl Acad Sci U S A. Jul. 15, 1992;89(14):6232-6.

Lee et al., A positive role for histone acetylation in transcription factor access to nucleosomal DNA. Cell. Jan. 15, 1993;72(1):73-84.

Lee et al., A Strategy for Macrocyclic Ring Closure and Functionalization Aimed toward Split-Pool Syntheses. J Am Chem Soc. 1999;121(45):10648-49.

Lizcano et al., Cell type-specific roles of histone deacetylase in TR ligand-independent transcriptional repression. Mol Cell Endocrinol. Feb. 14, 2001;172(1-2):13-20.

Lopez-Girona et al., Nuclear localization of Cdc25 is regulated by DNA damage and a 14-3-3 protein. Nature. Jan. 14, 1999;397(6715):172-5.

Luger et al., Crystal structure of the nucleosome core particle at 2.8 A resolution. Nature. Sep. 18, 1997;389(6648):251-60.

Lutterbach et al., ETO, a target of t(8;21) in acute leukemia, interacts with the N-CoR and mSin3 corepressors. Mol Cell Biol. Dec. 1998;18(12):7176-84.

MacBeath et al., Printing proteins as microarrays for high-throughput function determination. Science. Sep. 8, 2000;289(5485):1760-3.

Madura et al., N-recognin/Ubc2 interactions in the N-end rule pathway. J Biol Chem. Jun. 5, 1993;268(16):12046-54.

Maeji et al., Multi-pin peptide synthesis strategy for T cell determinant analysis. J Immunol Methods. Nov. 6, 1990;134(1):23-33.

Marcand et al., Silencing of genes at nontelomeric sites in yeast is controlled by sequestration of silencing factors at telomeres by Rap 1 protein. Genes Dev. Jun. 1, 1996;10(11):1297-309.

Marks et al., Molecular evolution of proteins on filamentous phage. Mimicking the strategy of the immune system. J Biol Chem. Aug. 15, 1992;267(23):16007-10.

Martinelli et al., Molecular therapy for multiple myeloma. Haematologica. Sep. 2001;86(9):908-17.

Marushige et al., Template properties of liver chromatin. J Mol Biol. Jan. 1966;15(1):160-74.

Massa et al., Synthesis and antimicrobial and cytotoxic activities of pyrrole-containing analogues of trichostatin A. J Med Chem. Oct. 1990;33(10):2845-9.

McKenzie et al., The centromere and promoter factor, 1, CPF1, of *Saccharomyces cerevisiae* modulates gene activity through a family of factors including SPT21, RPD1 (SIN3), RPD3 and CCR4. Mol Gen Genet. Sep. 1993;240(3):374-86.

Megee et al., Genetic analysis of histone H4: essential role of lysines subject to reversible acetylation. Science. Feb. 16, 1990;247(4944):841-5.

Merrifield et al., Solid Phase Peptide Syntheses. I. The Synthesis of a Tetrapeptide. J Am Chem Soc. 1963;85:2149-54.

Miller et al., Histone deacetylase inhibitors. J Med Chem. Nov. 20, 2003;46(24):5097-116.

Miller et al., N-terminal methionine-specific peptidase in *Salmonella typhimurium*. Proc Natl Acad Sci U S A. May 1987;84(9):2718-22.

Miska et al., HDAC4 deacetylase associates with and represses the MEF2 transcription factor. EMBO J. Sep. 15, 1999;18(18):5099-107.

Moazed, Enzymatic activities of Sir2 and chromatin silencing. Curr Opin Cell Biol. Apr. 2001;13(2):232-8.

Mori et al., Synthesis of trichostatin A, a potent differentiation inducer of friend leukemic cells, and its antipode. Tetrahedron. 1988;44:6013-20.

Mowat et al., Rearrangements of the cellular p53 gene in erythroleukaemic cells transformed by Friend virus. Nature. Apr. 18-24, 1985;314(6012):633-6.

Mullins et al., Transgenesis in nonmurine species. Hypertension. Oct. 1993;22(4):630-3.

Munshi et al., Acetylation of HMG I(Y) by CBP turns off IFN beta expression by disrupting the enhanceosome. Mol Cell. Oct. 1998;2(4):457-67.

Mutch et al., Effects of end groups on the stimulatory capacity of minimal length T cell determinant peptides. Pept Res. May-Jun. 1991;4(3):132-7.

Nagai et al., Synthesis of a Bicyclic Dipeptide with the Shape of β-Turn Central Part. Tetrahedron Lett. 1985;26:647-50.

Nagy et al., Nuclear receptor repression mediated by a complex containing SMRT, mSin3A, and histone deacetylase. Cell. May 2, 1997;89(3):373-80.

Nakazawa et al., UV and skin cancer: specific p53 gene mutation in normal skin as a biologically relevant exposure measurement. Proc Natl Acad Sci U S A. Jan. 4, 1994;91(1):360-4.

Narang, DNA Synthesis. Tetrahedron. 1983;39:3-22.

Nardelii et al., A chemically defined synthetic vaccine model for HIV-1. J Immunol. Feb. 1, 1992;148(3):914-20.

Nasmyth et al., Both positive and negative regulators of HO transcription are required for mother-cell-specific mating-type switching in yeast. Cell. Feb. 27, 1987;48(4):579-87.

Needleman et al., A general method applicable to the search for similarities in the amino acid sequence of two proteins. J Mol Biol. Mar. 1970;48(3):443-53.

Needles et al., Generation and screening of an oligonucleotide-encoded synthetic peptide library. Proc Natl Acad Sci. 1993;90:10700-04.

Neer et al., The ancient regulatory-protein family of WD-repeat proteins. Nature. Sep. 22, 1994;371(6495):297-300.

Nestler et al., A General Method for Molecular Tagging of Encoded Combinatorial Chemistry Libraries. J Org Chem. 1994;59:4723-24.

Ng et al., Histone deacetylases: silencers for hire. Trends Biochem Sci. Mar. 2000;25(3):121-6.

Ngo et al., Computational complexity, protein structure prediction, and the ILeventhal paradox. In: The Protein Folding Problem and Tertiary Structure Prediction. Merz et al., eds, Birhauser, Boston, MA. 1994:433-506.

Nielsen et al., Synthetic Methods for the Implementation of Encoded Combinatorial Chemistry. J Am Chem Soc. 1993;115:9812-13.

Nielsen et al., Toward Chemical Implementation of Encoded Combinatorial Libraries. Methods Compan Methods Enzymol. 1994;6:361-71.

Nikolaiev et al., Peptide-encoding for structure determination of nonsequenceable polymers within libraries synthesized and tested on solid-phase supports. Pept Res. May-Jun. 1993;6(3):161-70.

Noll, Characterization of macromolecules by constant velocity sedimentation. Nature. Jul. 22, 1967;215(5099):360-3.

O'Gorman et al., Recombinase-mediated gene activation and site-specific integration in mammalian cells. Science. Mar. 15, 1991;251(4999):1351-5.

Oliva et al., Histone hyperacetylation can induce unfolding of the nucleosome core particle. Nucleic Acids Res. May 11, 1990;18(9):2739-47.

Orban et al., Tissue- and site-specific DNA recombination in transgenic mice. Proc Natl Acad Sci U S A. Aug. 1, 1992;89(15):6861-5.

Park et al., Point mutations in the yeast histone H4 gene prevent silencing of the silent mating type locus HML. Mol Cell Biol. Sep. 1990;10(9):4932-4.

Patek et al., Safety-catch anchoring linkage for synthesis of peptide amides by Boc/Fmoc strategu. Tetrahedron Lett. 1991;32:3891-94.

Perrod et al., A cytosolic NAD-dependent deacetylase, Hst2p, can modulate nucleolar and telomeric silencing in yeast. EMBO J. Jan. 15, 2001;20(1-2):197-209.

Peterson et al., Small molecule developmental screens reveal the logic and timing of vertebrate development. Proc Natl Acad Sci U S A. Nov. 21, 2000;97(24):12965-9.

Phillips, The challenge of gene therapy and DNA delivery. J Pharm Pharmacol. Sep. 2001;53(9):1169-74.

Posnett et al., A novel method for producing anti-peptide antibodies. Production of site-specific antibodies to the T cell antigen receptor beta-chain. J Biol Chem. Feb. 5, 1988;263(4):1719-25.

Probst et al., Human liver arylacetamide deacetylase. Molecular cloning of a novel esterase involved in the metabolic activation of arylamine carcinogens with high sequence similarity to hormone-sensitive lipase. J Biol Chem. Aug. 26, 1994;269(34):21650-6.

Qian et al., A retinoblastoma-binding protein related to a negative regulator of Ras in yeast Nature. Aug. 12, 1993;364(6438):648-52.

Remiszewski, The discovery of NVP-LAQ824: from concept to clinic. Curr Med Chem. Nov. 2003;10(22):2393-402.

Richon et al., A class of hybrid polar inducers of transformed cell differentiation inhibits histone deacetylases. Proc Natl Acad Sci U S A. Mar. 17, 1998;95(6):3003-7.

Richon et al., Histone deacetylase inhibitor selectively induces p21WAF1 expression and gene-associated histone acetylation. Proc Natl Acad Sci U S A. Aug. 29, 2000;97(18):10014-9.

Richon et al., Second generation hybrid polar compounds are potent inducers of transformed cell differentiation. Proc Natl Acad Sci U S A. Jun. 11, 1996;93(12):5705-8.

Rine et al., Four genes responsible for a position effect on expression from HML and HMR in *Saccharomyces cerevisiae*. Genetics. May 1987;116(1):9-22.

Rittinger et al., Structural analysis of 14-3-3 phosphopeptide complexes identifies a dual role for the nuclear export signal of 14-3-3 in ligand binding. Mol Cell. Aug. 1999;4(2):153-66.

Roberts et al., Directed evolution of a protein: selection of potent neutrophil elastase inhibitors displayed on M13 fusion phage. Proc Natl Acad Sci U S A. Mar. 15, 1992;89(6):2429-33.

Robertson et al., Germ-line transmission of genes introduced into cultured pluripotential cells by retroviral vector. Nature. Oct. 2-8, 1986;323(6087):445-8.

Rudinger, Characteristics of the amino acids as components of a peptide hormone sequence. In: Peptide Hormones. J.A. Parsons, ed. University Park Press, Baltimore, MD. 1976;1-7.

Rundlett et al., HDA1 and RPD3 are members of distinct yeast histone deacetylase complexes that regulate silencing and transcription. Proc Natl Acad Sci U S A. Dec. 10, 1996;93(25):14503-8.

Sanchez Del Pino et al., Properties of the yeast nuclear histone deacetylase. Biochem J. Nov. 1, 1994;303 ( Pt 3):723-9.

Sasaki et al., Ligand-induced recruitment of a histone deacetylase in the negative-feedback regulation of the thyrotropin beta gene. EMBO J. Oct. 1, 1999;18(19):5389-98.

Sato et al., Synthesis and Antibiotic Activity of a Gramicidin S Analogue containing Bicyclic β-Turn Dipeptides. J Chem Soc Perkin Trans. 1986;1:1231-34.

Sawa et al., Histone deacetylase inhibitors such as sodium butyrate and trichostatin A induce apoptosis through an increase of the bcl-2-related protein Bad. Brain Tumor Pathol. 2001;18(2):109-14.

Schena, Quantitative Monitoring of Gene Expression Patterns with a Complementary DNA Microarray. Science. 1995;270:467-70.

Schlienger et al., Human immunodeficiency virus type 1 major neutralizing determinant exposed on hepatitis B surface antigen particles is highly immunogenic in primates. J Virol. Apr. 1992;66(4):2570-6.

Schmidt et al., Rapid determination of methadone in plasma, cerebrospinal fluid, and urine by gas chromatography and its application to routine drug monitoring. Pharm Res. Mar. 1993;10(3):441-4.

Scott et al., Searching for peptide ligands with an epitope library. Science. Jul. 27, 1990;249(4967):386-90.

Seffernick et al., Melamine deaminase and atrazine chlorohydrolase: 98 percent identical but functionally different. J Bacteriol. Apr. 2001;183(8):2405-10.

Shpaer, GeneAssist. Smith-Waterman and other database similarity searches and identification of motifs. Methods Mol Biol. 1997;70:173-87.

Sikorski et al., A system of shuttle vectors and yeast host strains designed for efficient manipulation of DNA in *Saccharomyces cerevisiae*. Genetics. May 1989;122(1):19-27.

Smith et al., A phylogenetically conserved NAD+-dependent protein deacetylase activity in the Sir2 protein family. Proc Natl Acad Sci U S A. Jun. 6, 2000;97(12):6658-63.

Smith et al., Comparison of biosequences. Adv Appl Math. 1981;2:482-89.

Stewart et al., Expression of retroviral vectors in transgenic mice obtained by embryo infection. EMBO J. Feb. 1987;6(2):383-8.

Stillman et al., Epistasis analysis of suppressor mutations that allow HO expression in the absence of the yeast SW15 transcriptional activator. Genetics. Mar. 1994;136(3):781-8.

Strebhardt et al., Additional member of the protein-tyrosine kinase family: the src- and lck-related protooncogene c-tkl. Proc Natl Acad Sci U S A. Dec. 1987;84(24):8778-82.

Suzuki et al., Synthesis and histone deacetylase inhibitory activity of new benzamide derivatives. J Med Chem. Jul. 29, 1999;42(15):3001-3.

Tanner et al., Silent information regulator 2 family of NAD-dependent histone/protein deacetylases generates a unique product, 1-O-acetyl-ADP-ribose. Proc Natl Acad Sci U S A. Dec. 19, 2000;97(26):14178-82.

Tanny et al., Coupling of histone deacetylation to NAD breakdown by the yeast silencing protein Sir2: Evidence for acetyl transfer from substrate to an NAD breakdown product. Proc Natl Acad Sci U S A. Jan. 16, 2001;98(2):415-20. Epub Dec. 26, 2000.

Thornton et al., Protein Engineering: Editorial Overview. Curr Opin Biotechnol. 1995;6(4):367-69.

Tissenbaum et al., Increased dosage of a sir-2 gene extends lifespan in *Caenorhabditis elegans*. Nature. Mar. 8, 2001;410(6825):227-30.

Tsang et al., CobB, a new member of the SIR2 family of eucaryotic regulatory proteins, is required to compensate for the lack of nicotinate mononucleotide:5,6-dimethylbenzimidazole phosphoribosyltransferase activity in cobT mutants during cobalamin biosynthesis in *Salmonella typhimurium* LT2. J Biol Chem. Nov. 27, 1998;273(48):31788-94.

Turner, Decoding the nucleosome. Cell. Oct. 8, 1993;75(1):5-8.

Valerio et al., Multipin peptide synthesis at the micromole scale using 2-hydroxyethyl methacrylate grafted polyethylene supports. Int J Pept Protein Res. Jul. 1993;42(1):1-9.

Valerio et al., Synthesis of peptide analogues using the multipin peptide synthesis method. Anal Biochem. Aug. 15, 1991;197(1):168-77.

Van Der Krol et al., Modulation of eukaryotic gene expression by complementary RNA or DNA sequences. Biotechniques. Nov.-Dec. 1988;6(10):958-76.

Van Der Putten et al., Efficient insertion of genes into the mouse germ line via retroviral vectors. Proc Natl Acad Sci U S A. Sep. 1985;82(18):6148-52.

Varga-Weisz et al., Chromatin-remodeling factors: machines that regulate? Curr Opin Cell Biol. Jun. 1998;10(3):346-53.

Verdel et al., Identification of a new family of higher eukaryotic histone deacetylases. Coordinate expression of differentiation-dependent chromatin modifiers. J Biol Chem. Jan. 22, 1999;274(4):2440-5.

Vidal et al., RPD3 encodes a second factor required to achieve maximum positive and negative transcriptional states in *Saccharomyces cerevisiae*. Mol Cell Biol. Dec. 1991;11(12):6317-27.

Walker et al., Affinity chromatography of mammalian and yeast nucleosomes. Two modes of binding of transcriptionally active mammalian nucleosomes to organomercurial-agarose columns, and contrasting behavior of the active nucleosomes of yeast. J Biol Chem. Apr. 5, 1990;265(10):5736-46.

Wallace et al., Understanding cytochrome c function: engineering protein structure by semisynthesis. FASEB J. Apr. 1, 1990;7(6):505-15.

Wang et al., ETO, fusion partner in t(8;21) acute myeloid leukemia, represses transcription by interaction with the human N-CoR/mSin3/HDAC1 complex. Proc Natl Acad Sci U S A. Sep. 1, 1998;95(18):10860-5.

Wang et al., HDAC4, a human histone deacetylase related to yeast HDA1, is a transcriptional corepressor. Mol Cell Biol. Nov. 1999;19(11):7816-27.

Wang et al., Isolation of high-affinity peptide antagonists of 14-3-3 proteins by phage display. Biochemistry. Sep. 21, 1999;38(38):12499-504.

Weinberg, Finding the anti-oncogene. Sci Am. Sep. 1988;259(3):44-51.

Wennemers et al., Cyclooligomeric Receptors Based on Trimesic Acid and 1,2-Diamines. Minimal Structure for Sequence-Selective Peptide Binding. J Org Chem. 1995;60:1108-09.

Witkowski et al., Conversion of a beta-ketoacyl synthase to a malonyl decarboxylase by replacement of the active-site cysteine with glutamine. Biochemistry. Sep. 7, 1999;38(36):11643-50.

Workman et al., Alteration of nucleosome structure as a mechanism of transcriptional regulation. Annu Rev Biochem. 1998;67:545-79.

Xie et al., Sum1 and Hst1 repress middle sporulation-specific gene expression during mitosis in *Saccharomyces cerevisiae*. EMBO J. Nov. 15, 1999;18(22):6448-54.

Xu et al., Coactivator and corepressor complexes in nuclear receptor function. Curr Opin Genet Dev. Apr. 1999;9(2):140-7.

Xue et al., NURD, a novel complex with both ATP-dependent chromatin-remodeling and histone deacetylase activities. Mol Cell. Dec. 1998;2(6):851-61.

Yaffe et al., The structural basis for 14-3-3:phosphopeptide binding specificity. Cell. Dec. 26, 1997;91(7):961-71.

Yang et al., Cloning and characterization of two mouse genes with homology to the yeast Sir2 gene. Genomics. Nov. 1, 2000;69(3):355-69.

Yang et al., Maintenance of G2 arrest in the *Xenopus oocyte*: a role for 14-3-3-mediated inhibition of Cdc25 nuclear import. EMBO J. Apr. 15, 1999;18(8):2174-83.

Yang et al., Transcriptional repression by YY1 is mediated by interaction with a mammalian homolog of the yeast global regulator RPD3. Proc Natl Acad Sci U S A. Nov. 12, 1996;93(23):12845-50.

Yoon et al., Cyclooligomeric Receptors for the Sequence Selective Binding of Peptides. A Tetrahedral Receptor from the Trimesic Acid and 1,2-Diamines. Tetrahedron Lett. 1994;35:8557-60.

Yoshida et al., A novel tetracyclic peptide, trapoxin, induces phenotypic change from transformed to normal in sis-oncogene-transformed NIH3T3 cells. Jpn J Cancer Res. Apr. 1992;83(4):324-8.

Yoshida et al., Potent and specific inhibition of mammalian histone deacetylase both in vivo and in vitro by trichostatin A. J Biol Chem. Oct. 5, 1990;265(28):17174-9.

Yoshida et al., Trichostatin A and tra oxin: novel chemical probes for the role of histone 18 is acetylation in chromatin structure and function. Bioessays. May 1995;17(5):423-28.

Zervos et al., Mxil, a protein that specifically interacts with Max to bind Myc-Max recognition sites. Cell. Jan. 29, 1993;72(2):223-32.

Zhang et al., The dermatomyositis-specific autoantigen Mi2 is a component of a complex containing histone deacetylase and nucleosome remodeling activities. Cell. Oct. 16, 1998;95(2):279-89.

Zimmermann et al., Conformational and epitope mapping of herpes-simplex-virus type-1 thymidine kinase using synthetic peptide segments. Eur J Biochem. Sep. 1, 1991;200(2):519-28.

Goy et al., Phase II study of proteasome inhibitor bortezomib in relapsed or refractory B-cell non-Hodgkin's lymphoma. J. Clin. Oncol. Feb. 1, 2005;23(4):667-75. Epub Dec. 21, 2004.

CAS Registry File RN 505-22-6, STN Entry Date: Nov. 16, 1984.

Extended European Search Report for EP 07776589.9, mailed Jun. 1, 2012.

Eliel et al., Conformational analysis. XX. Stereochemistry of reaction of Grignard reagents with ortho esters. Synthesis of 1,3-dioxanes with axial substituents at C-2. J Am Chem Soc. 1970;92(3):584-590.

Mai et al., Class II (IIa)-selective histone deacetylase inhibitors. 1. Synthesis and biological evaluation of novel (aryloxopropenyl)pyrrolyl hydroxyamides. J Med Chem. May 5, 2005;48(9):3344-53.

Powell et al., Anti-1,3-diols by Addition of Dialkylzinc Reagents to 4-Acetoxy-1,3-dioxanes. J Org Chem. Mar. 19, 1999;64(6):2026-2037.

Sarraf et al., Rhodium-catalyzed formylation of organomercurials: application to efficient polyol synthesis. Org Lett. Oct. 5, 2000;2(20):3205-8.

* cited by examiner

Medicinal Chemistry: Development of HT/IF Quantitative Assay

| | HDAC Inhibition | TDAC Inhibition |
|---|---|---|
| Tubacin | 7.2 uM | 0.9 uM |
| DHM-Tubacin | 25 uM | 1.5 uM |
| NKI-59-1 | 11 uM | 1.5 uM |
| NKI-60-1 | 3 uM | 0.9 uM |
| NKI-82-1 | 1.5 uM | 0.45 uM |
| NKI-84-1 | 1.5 uM | 160 nM |
| NKI-94-1 | 1.6 uM | 0.5 uM |
| NKI-81-1 | 13 uM | 3.8 uM |
| Isotubacin | >40 uM | 4 uM |

|  | Average KD (uM) | Average KD (M) | Percent Bound |
| --- | --- | --- | --- |
| DHM Tubacin | 96.85 | 9.69E-05 | 87.5% |
| Tubacin | 5.53 | 5.53E-06 | 99.2% |
| 59 | 100.8 | 1.01E-04 | 87.1% |
| 60 | 67.3 | 6.73E-05 | 91.0% |
| 81 | 244.25 | 2.44E-04 | 73.6% |
| 84 | 80.85 | 8.09E-05 | 89.4% |
| 93 | 152 | 1.52E-04 | 81.7% |
| 94 | 95.8 | 9.58E-05 | 87.7% |
| 165 | 476 | 4.76E-04 | 58.8% |
| 201 | 73.7 | 7.37E-05 | 90.2% |
| 207 | 202.75 | 2.03E-04 | 77.0% |
| 208 | 184.75 | 1.85E-04 | 78.6% |
| 233 | 99.8 | 9.98E-05 | 87.2% |
| 234 | 563.5 | 5.64E-04 | 54.7% |
| 235 | 676 | 6.76E-04 | 50.1% |
| 236 | 108 | 1.08E-04 | 86.3% |
| 1428 | 557 | 5.57E-04 | 55.0% |
| SAHA | 333 | 3.33E-04 | 67.1% |

HSA Binding by SPR

Fig. 14-1

HISTONE DEACETYLASE AND TUBULIN DEACETYLASE INHIBITORS

RELATED APPLICATIONS

The present application is a U.S. national phase application under 35 U.S.C. §371 of international PCT application number PCT/US2007/010587, filed May 2, 2007, which claims priority under 35 U.S.C. §119(e) to U.S. provisional patent application, U.S. Ser. No. 60/797,211, filed May 3, 2006; each of which is incorporated herein by reference.

GOVERNMENT SUPPORT

The work described herein was supported, in part, by grants from the National Institutes of Health (370 31215 017490 614101 0001 00000; 370 31215 133800 341450 0402 44046). The United States government may have certain rights in the invention.

BACKGROUND OF THE INVENTION

The identification of small organic molecules that affect specific biological functions is an endeavor that impacts both biology and medicine. Such molecules are useful as therapeutic agents and as probes of biological function. In but one example from the emerging field of chemical genetics, in which small molecules can be used to alter the function of biological molecules to which they bind, these molecules have been useful at elucidating signal transduction pathways by acting as chemical protein knockouts, thereby causing a loss of protein function. (Schreiber et al., *J. Am. Chem. Soc.*, 1990, 112, 5583; Mitchison, *Chem. and Biol.*, 1994, 1, 3) Additionally, due to the interaction of these small molecules with particular biological targets and their ability to affect specific biological function (e.g. gene transcription), they may also serve as candidates for the development of new therapeutics. One important class of small molecules, natural products, which are small molecules obtained from nature, clearly have played an important role in the development of biology and medicine, serving as pharmaceutical leads, drugs (Newman et al., *Nat. Prod. Rep.* 2000, 17, 215-234), and powerful reagents for studying cell biology (Schreiber, S. L. *Chem. and Eng. News* 1992 (October 26), 22-32).

One biological target of recent interest is histone deacetylase (see, for example, a discussion of the use of inhibitors of histone deacetylases for the treatment of cancer: Marks et al. *Nature Reviews Cancer* 2001, 1, 194; Johnstone et al. *Nature Reviews Drug Discovery* 2002, 1, 287). Post-translational modification of proteins through acetylation and deacetylation of lysine residues plays a critical role in regulating their cellular functions. HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300-308). HDACs participate in cellular pathways that control cell shape and differentiation, and an HDAC inhibitor has been shown effective in treating an otherwise recalcitrant cancer (Warrell et al. *J. Natl. Cancer Inst.* 1998, 90, 1621-1625). At this time, eleven human HDACs, which use Zn as a cofactor, have been identified (Taunton et al. *Science* 1996, 272, 408-411; Yang et al. *J. Biol. Chem.* 1997, 272, 28001-28007. Grozinger et al. *Proc. Natl. Acad. Sci. U.S.A.* 1999, 96, 4868-4873; Kao et al. *Genes Dev.* 2000, 14, 55-66. Hu et al. *J. Biol. Chem.* 2000, 275, 15254-15264; Zhou et al. *Proc. Natl. Acad. Sci. U.S.A.* 2001, 98, 10572-10577; Venter et al. *Science* 2001, 291, 1304-1351) these members fall into three classes (class I, II, and IV). An additional seven HDACs have been identified which use NAD as a cofactor. To date, no small molecules are known that selectively target any particular class or individual members of this family ((for example ortholog-selective HDAC inhibitors have been reported: (a) Meinke et al. *J. Med. Chem.* 2000, 14, 4919-4922; (b) Meinke, et al. *Curr. Med. Chem.* 2001, 8, 211-235). There remains a need for preparing structurally diverse HDAC and tubulin deacetylase (TDAC) inhibitors particularly ones that are potent and/or selective inhibitors of particular classes of HDACs or TDACs and individual HDACs and TDACs.

SUMMARY OF THE INVENTION

The present invention provides novel histone deacetylase and tubulin deacetylase inhibitors and methods of preparing and using these compounds. These compounds are particularly useful in the treatment of proliferative diseases such as cancer, inflammatory diseases, infectious diseases, protein degradation disorders, and protein deposition disorders such as Alzheimer's Disease. Certain compounds are particularly useful in specifically inhibiting one class or member of HDACs. Other compounds are particularly useful in specifically inhibiting one class or member of tubulin deacetylases (TDAC). Yet other compounds are useful in inhibiting degradation of proteins by the aggresome.

The present invention provides novel inhibitors of HDACs and TDACs with a 1,3-dioxane core structure. Compounds of the invention basically fall into two classes, wherein the 1,3-dioxane core of the compound is oriented differently in each class. That is, the 1,3-dioxane core is rotated 120° in each class as compared to tubacin derivatives and as shown in the structures below (see, also, FIG. 1). The inventive compounds are of the formulae:

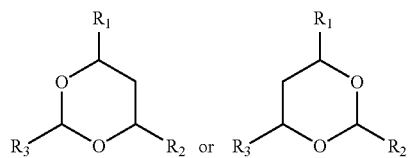

wherein
$R_1$ is cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —$SR_A$; —$SOR_A$; —$SO_2R_A$; —$N(R_A)_2$; —$NHC(O)R_A$; or —$C(R_A)_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —$C(=O)R_B$; —$CO_2R_B$; —CN; —SCN; —$SR_B$; —$SOR_B$; —$SO_2R_B$; —$NO_2$;

—N($R_B$)$_2$; —NHC(O)$R_B$; or —C($R_B$)$_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_C$; —C(=O)$R_C$; —CO$_2R_C$; —CN; —SCN; —S$R_C$; —SO$R_C$; —SO$_2R_C$; —NO$_2$; —N($R_C$)$_2$; —NHC(O)$R_C$; or —C($R_C$)$_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and pharmaceutically acceptable salts and derivatives thereof. In general, $R_1$ comprises a metal chelating functional group (e.g., hydroxyamic acids, thiols, carboxic acids, ortho-aminoanilides, etc.). The metal chelating group is thought to bind the active site $Zn^{+2}$ ion of deacetylase enzymes. In certain embodiments, $R_2$ is a substituted or unsubstituted heteroaliphatic moiety (e.g., a heteroaliphatic moiety substituted with a heteroaryl ring, which may be optionally substituted). In certain embodiments, $R_3$ is a substituted or unsubstituted aromatic ring system (e.g., a substituted or unsubstituted phenyl).

Compounds of formula:

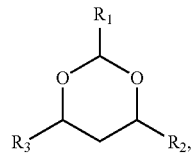

that is, tubacin derivatives, have been described in U.S. patent applications, U.S. Ser. No. 11/386,959, filed Mar. 22, 2006; U.S. Ser. No. 60/664,470, filed Mar. 22, 2005; U.S. Ser. No. 60/289,850, filed May 9, 2001; U.S. Ser. No. 10/144,316, filed May 9, 2002; and U.S. Ser. No. 10/621,276, filed Jul. 17, 2003; each of which is incorporated herein by reference. These compounds have been found to be particularly useful in inhibiting HDACs such as HDAC6 and also in the treatment of multiple myeloma by inhibiting HDAC6 known to play a role in the degradation of proteins by the aggresome.

Inventive compounds of the class of formula:

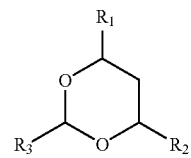

are compounds of the "isotubacin" class. The 1,3-dioxane core of these compounds has been rotated 120° counterclockwise as compared to compounds of the "tubacin" class. The compounds of this class are also useful in treating cancer (e.g., multiple myeloma, breast cancer, non-Hodgkin's lymphoma, ovarian cancer, acute myelogenous leukemia), protein degradation disorders (e.g., multiple myeloma, neurodegenerative disorders), protein deposition disorders (e.g., neurogenerative disorders), infectious diseases, and proliferative disorders (e.g., diabetic retinopathy, inflammatory diseases, angiogenesis). Pharmaceutical compositions and kits comprising these compounds are also provided by the present invention. In certain particular embodiments, compounds of this class are useful in the treatment of multiple myeloma, leukemia, lymphoma, breast cancer, and prostate cancer. Pharmaceutical composition of the inventive compounds may also comprises other chemotherapeutic agents or other pharmaceutical agents typically administered during the treatment of cancer (e.g., anti-nausea medications, analgesics, nutritional supplements, etc.). The present invention also provides synthetic method for preparing compounds of the "isotubacin" class.

Inventive compounds of the class of formula:

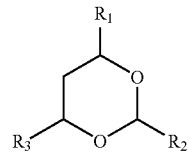

are compounds of the "isoisotubacin" class. The 1,3-dioxane core of the compounds of this class has been rotated 120° clockwise as compared to compounds of the "tubacin" class. The compounds of this class are also useful in treating cancer (e.g., multiple myeloma, breast cancer, non-Hodgkin's lymphoma, ovarian cancer, acute myelogenous leukemia), protein degradation disorders (e.g., neurodegenerative disorders, multiple myeloma), protein deposition disorders (e.g., neurodegenerative disorders), infectious diseases, and proliferative disorders (e.g., diabetic retinopathy, inflammatory diseases, angiogenesis). Pharmaceutical compositions and kits comprising these compounds are also included. In certain particular embodiments, compounds of this class are useful in the treatment of multiple myeloma, leukemia, lymphoma, breast cancer, and prostate cancer. Pharmaceutical composition of the inventive compounds may also comprises other chemotherapeutic agents or other pharmaceutical agents typically administered during the treatment of cancer (e.g., anti-nausea medications, analgesics, nutritional supplements, etc.). The present invention also provides synthetic method for preparing compounds of the "isoisotubacin" class.

The inventive compounds are also useful as tools to probe biological function (e.g., the degradation of proteins by the aggresome; inhibition of histone deacetylases, inhibition of tubulin deacetylases). For example, the compounds may be administered to wild type cells or altered cells to understand protein degradation pathways or the effect of acetylation on a protein's function. In certain embodiments, the compound inhibits a specific histone or tubulin deacetylase. The compounds may also be used to elucidate the cell cycle.

In another aspect, the present invention provides methods for inhibiting histone deacetylase activity, tubulin deacetylase activity, or aggresome activity in a patient or a biological sample, comprising administering to the patient, or contacting the biological sample with an effective amount of an inventive compound or a pharmaceutical composition thereof.

DEFINITIONS

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "acyl", as used herein, refers to a carbonyl-containing functionality, e.g., —C(=O)R', wherein R' is an aliphatic, alycyclic, heteroaliphatic, heterocyclic, aryl, heteroaryl, (aliphatic)aryl, (heteroaliphatic)aryl, heteroaliphatic(aryl) or heteroaliphatic(heteroaryl) moiety, whereby each of the aliphatic, heteroaliphatic, aryl, or heteroaryl moieties is substituted or unsubstituted, or is a substituted (e.g., hydrogen or aliphatic, heteroaliphatic, aryl, or heteroaryl moieties) oxygen or nitrogen containing functionality (e.g., forming a carboxylic acid, ester, or amide functionality).

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norbornyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the term "aryl", as used herein, refers to a stable mono- or polycyclic, unsaturated moiety having preferably 3-14 carbon atoms, each of which may be substituted or unsubstituted. In certain embodiments, the term "aryl" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaryl", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaryl" refers to a planar ring comprising at least one heteroatom, having p-orbitals perpendicular to the plane of the ring at each ring atom, and satisfying the Huckel rule where the number of pi electrons in the ring is (4n+2) wherein n is an integer.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl) aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein. The terms "halo" and "halogen" as used herein refer to an atom selected from fluorine, chlorine, bromine and iodine.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NH$_x$), tertiary (—NR$_x$R$_y$) or quaternary (—N$^+$R$_x$R$_y$R$_z$) amine, where R$_x$, R$_y$ and R$_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "alkylidene", as used herein, refers to a substituted or unsubstituted, linear or branched saturated divalent radical consisting solely of carbon and hydrogen atoms, having from one to n carbon atoms, having a free valence "-" at both ends of the radical. In certain embodiments, the alkylidene moiety has 1 to 6 carbon atoms.

The term "alkenylidene", as used herein, refers to a substituted or unsubstituted, linear or branched unsaturated divalent radical consisting solely of carbon and hydrogen atoms, having from two to n carbon atoms, having a free valence "-" at both ends of the radical, and wherein the unsaturation is present only as double bonds and wherein a double bond can exist between the first carbon of the chain and the rest of the molecule. In certain embodiments, the alkenylidene moiety has 2 to 6 carbon atoms.

The term "alkynylidene", as used herein, refers to a substituted or unsubstituted, linear or branched unsaturated divalent radical consisting solely of carbon and hydrogen atoms, having from two to n carbon atoms, having a free valence "-" at both ends of the radical, and wherein the unsaturation is present only as triple or double bonds and wherein a triple or double bond can exist between the first carbon of the chain and the rest of the molecule. In certain embodiments, the alkynylidene moiety has 2 to 6 carbon atoms.

Unless otherwise indicated, as used herein, the terms "alkyl", "alkenyl", "alkynyl", "heteroalkyl", "heteroalkenyl", "heteroalkynyl", "alkylidene", "alkenylidene", -(alkyl)aryl, -(heteroalkyl)aryl, -(heteroalkyl)aryl, -(heteroalkyl)heteroaryl, and the like encompass substituted and unsubstituted, and linear and branched groups. Similarly, the terms "aliphatic", "heteroaliphatic", and the like encompass substituted and unsubstituted, saturated and unsaturated, and linear and branched groups. Similarly, the terms "cycloalkyl", "heterocycle", "heterocyclic", and the like encompass substituted and unsubstituted, and saturated and unsaturated groups. Additionally, the terms "cycloalkenyl", "cycloalkynyl", "heterocycloalkenyl", "heterocycloalkynyl", "aromatic", "heteroaromatic", "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Pharmaceutically acceptable derivatives also include "reverse pro-drugs." Reverse pro-drugs, rather than being activated, are inactivated upon absorption. For example, as discussed herein, many of the ester-containing compounds of the invention are biologically active but are inactivated upon exposure to certain physiological environments such as a blood, lymph, serum, extracellular fluid, etc. which contain esterase activity. The biological activity of reverse pro-drugs and pro-drugs may also be altered by appending a functionality onto the compound, which may be catalyzed by an enzyme. Also, included are oxidation and reduction reactions, including enzyme-catalyzed oxidation and reduction reactions. Certain exemplary pharmaceutical compositions and pharmaceutically acceptable derivatives will be discussed in more detail herein below.

By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent-protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

The term "solid support", as used herein, refers to a material having a rigid or semi-rigid surface. Such materials will preferably take the form of small beads, pellets, disks, chips, dishes, multi-well plates, glass slides, wafers, or the like, although other forms may be used. In some embodiments, at least one surface of the substrate will be substantially flat. The term "surface" refers to any generally two-dimensional structure on a solid substrate and may have steps, ridges, kinks, terraces, and the like without ceasing to be a surface.

The term "polymeric support", as used herein, refers to a soluble or insoluble polymer to which an amino acid or other chemical moeity can be covalently bonded by reaction with a functional group of the polymeric support. Many suitable polymeric supports are known, and include soluble polymers such as polyethylene glycols or polyvinyl alcohols, as well as insoluble polymers such as polystyrene resins. A suitable polymeric support includes functional groups such as those described below. A polymeric support is termed "soluble" if a polymer, or a polymer-supported compound, is soluble under the conditions employed. However, in general, a soluble polymer can be rendered insoluble under defined conditions. Accordingly, a polymeric support can be soluble under certain conditions and insoluble under other conditions.

The term "linker," as used herein, refers to a chemical moiety utilized to attach a compound of interest to a solid support to facilitate synthesis of inventive compounds or a linker may attach one portion of a compound to another portion of a compound. Preferably, the linker comprises covalent bonds. Exemplary linkers are described herein. It will be appreciated that other linkers that are known in the art can also be employed for the synthesis of the compounds of the invention.

"Compound": The term "compound" or "chemical compound" as used herein can include organometallic compounds, organic compounds, metals, transitional metal complexes, and small molecules. In certain preferred embodiments, polynucleotides are excluded from the definition of compounds. In other preferred embodiments, polynucleotides and peptides are excluded from the definition of compounds. In a particularly preferred embodiment, the term compounds refers to small molecules (e.g., preferably, non-peptidic and non-oligomeric) and excludes peptides, polynucleotides, transition metal complexes, metals, and organometallic compounds.

"Small Molecule": As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized. Cell-Based Assays" *J. Am. Chem. Soc.* 120:8565, 1998; incorporated herein by reference). In certain other preferred embodiments, natural-product-like small molecules are utilized.

"Natural Product-Like Compound": As used herein, the term "natural product-like compound" refers to compounds that are similar to complex natural products which nature has selected through evolution. Typically, these compounds contain one or more stereocenters, a high density and diversity of functionality, and a diverse selection of atoms within one structure. In this context, diversity of functionality can be defined as varying the topology, charge, size, hydrophilicity, hydrophobicity, and reactivity to name a few, of the functional groups present in the compounds. The term, "high density of functionality", as used herein, can preferably be used to define any molecule that contains preferably three or more latent or active diversifiable functional moieties. These structural characteristics may additionally render the inventive compounds functionally reminiscent of complex natural products, in that they may interact specifically with a particular biological receptor, and thus may also be functionally natural product-like.

"Metal chelator": As used herein, the term "metal chelator" refers to any molecule or moiety that is capable of forming a complex (i.e., "chelates") with a metal ion. In certain exemplary embodiments, a metal chelator refers to any molecule or moiety that "binds" to a metal ion, in solution, making it unavailable for use in chemical/enzymatic reactions. In certain embodiments, the solution comprises aqueous environments under physiological conditions. Examples of metal ions include, but are not limited to, $Ca^{2+}$, $Fe^{3+}$, $Zn^{2+}$, $Na^+$, etc. In certain embodiments, the metal chelator bind $Zn^{2+}$, which is found at the active site of HDACs. In certain embodiments, molecules of moieties that precipitate metal ions are not considered to be metal chelators.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

DETAILED DESCRIPTION OF THE INVENTION

Figure 1:
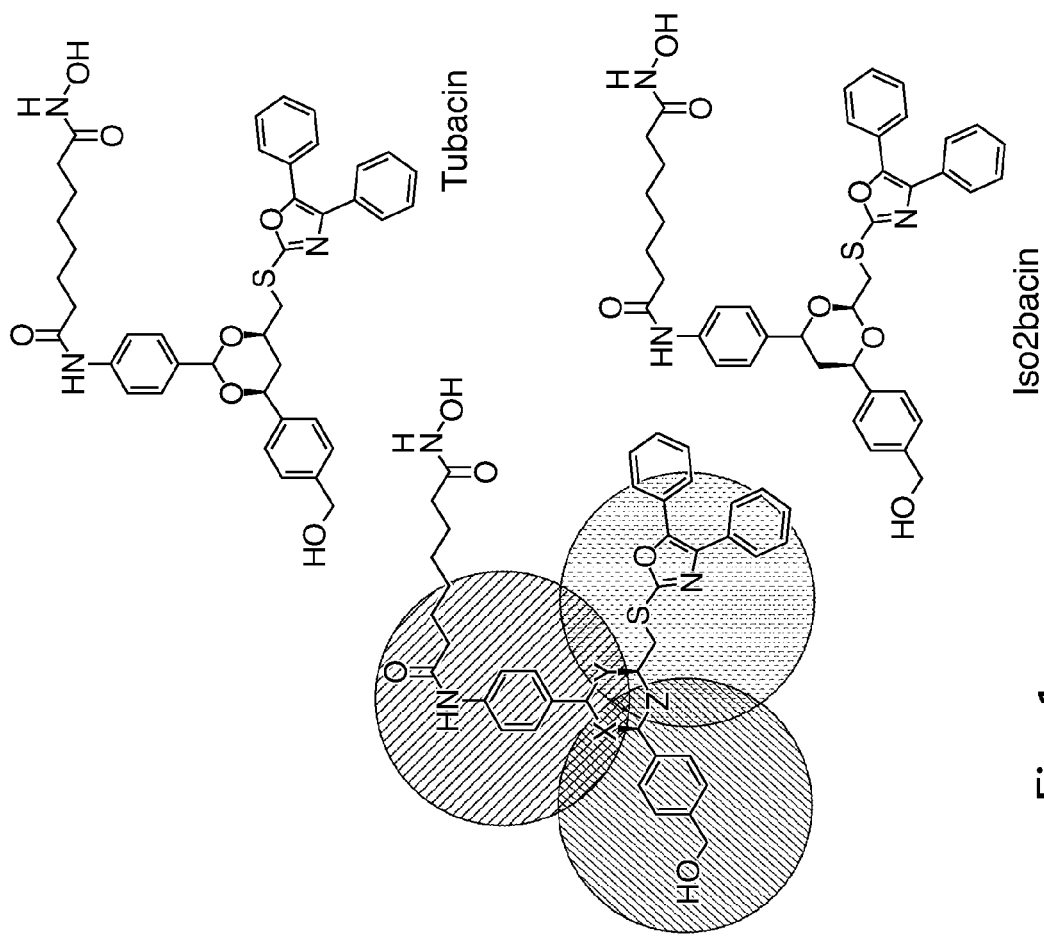
FIG. 1 shows examples from the three classes of inventive compounds—tubacin, isotubacin, and isoisotubacin.
Figure 1:
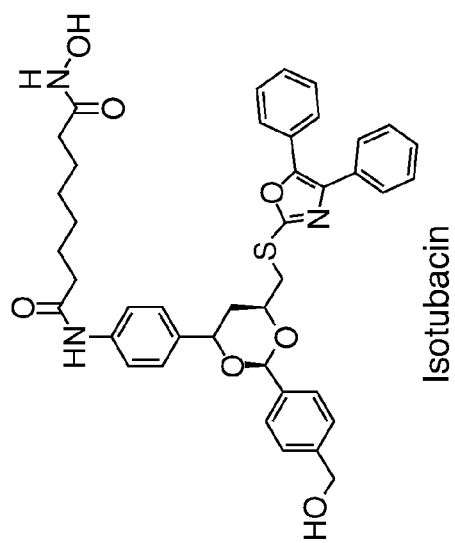

As discussed above, there remains a need for the development of novel inhibitors of histone deacetylases, tubulin histone deacetylases, and the aggresome. In particular, inhibitors that are more potent and/or more specific for their particular target than known HDAC and TDAC inhibitors. HDAC inhibitors specific for a certain class or member of the HDAC family would be particularly useful both in the treatment of proliferative diseases and protein deposition disorders and in the study of HDACs. Inhibitors that are specific for HDAC versus TDAC and vice versa are also useful in treating disease and probing biological pathways. The present invention provides novel compounds, methods for the synthesis thereof, pharmaceutical compositions thereof, and methods of using these compounds to treat cancer, proliferative diseases, protein degradation disorders, and protein deposition disorders.

Compounds of the Invention

As discussed above, the present invention provides compounds useful for the treatment of various diseases. In certain embodiments, the compounds of the present invention are useful as inhibitors of histone or tubulin deacetylases and thus are useful as anti-cancer agents, and thus may be useful in the treatment of cancer, by effecting tumor cell death or inhibiting the growth of tumor cells. In certain exemplary embodiments, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In certain embodiments, the compounds are useful in the treatment of multiple myeloma. Additionally, the inventive compounds may also be useful in the treatment of protozoal infections. The inventive compounds are also useful in the treatment of diseases associated with aberrant protein catabolism, for example, protein degradation disorders, disorders associated with misfolded proteins, and protein deposition disorders. In certain embodiments, the compound are useful in the treatment of the protein deposition disorders, Wilson's disease, spinocerebellar ataxia, prion disease, Parkinson's disease, Huntington's disease, familian amyotrophic lateral sclerosis, amyloidosis, Alzheimer's disease, Alexander's diseases, alcoholic liver disease, cystic fibrosis, Pick's disease, and Lewy body dementia. In certain exemplary embodiments, the compounds of the invention are useful for disorders associated with histone deacetylation activity. In certain exemplary embodiments, the compounds of the invention are useful for disorders associated with tubulin deacetylation activity. In other exemplary embodiments, the compounds of the invention are useful for disorders associated with aggresome activity. In certain embodiments, the compounds, particularly compounds with an ester moiety, are useful in treating skin disorders. Exemplary skin disorders that may be treated using certain of the inventive compounds include cutaneous T-cell lymphoma (CTCL), psoriasis, hair loss, dermatitis, etc.

Compounds of this invention comprise those, as set forth above and described herein, and are illustrated in part by the various classes, subclasses, subgenera, and species disclosed herein. The invention provides compounds, e.g., compounds useful in the methods, pharmaceutical compositions, kits, and packaged compositions of the invention. The inventive compounds are inhibitors of histone deacetylases, tubulin deacetylases, or the aggresome. The compounds of the invention are typically based on a 1,3-dioxane core structure.

Exemplary classes of compounds of the invention include compounds of the formula:

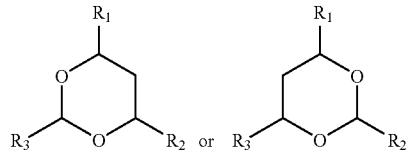

wherein

R₁ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; —C(=O)R$_B$; —CO$_2$R$_B$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and pharmaceutically acceptable salts and derivatives thereof. In certain embodiments, $R_1$ comprises a metal chelating functional group (e.g., hydroxyamic acids, thiols, carboxylic acids, ortho-aminoanilides, etc.).

As will be appreciated by one of skill in this art, the 1,3-dioxane core has been rotated 120° in each of the two classes of compounds as compared to the 1,3-dioxane core of tubacin and its derivatives.

The invention also provides compounds of the isotubacin class. These compounds are of the formula:

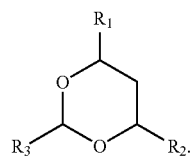

Figure 2:
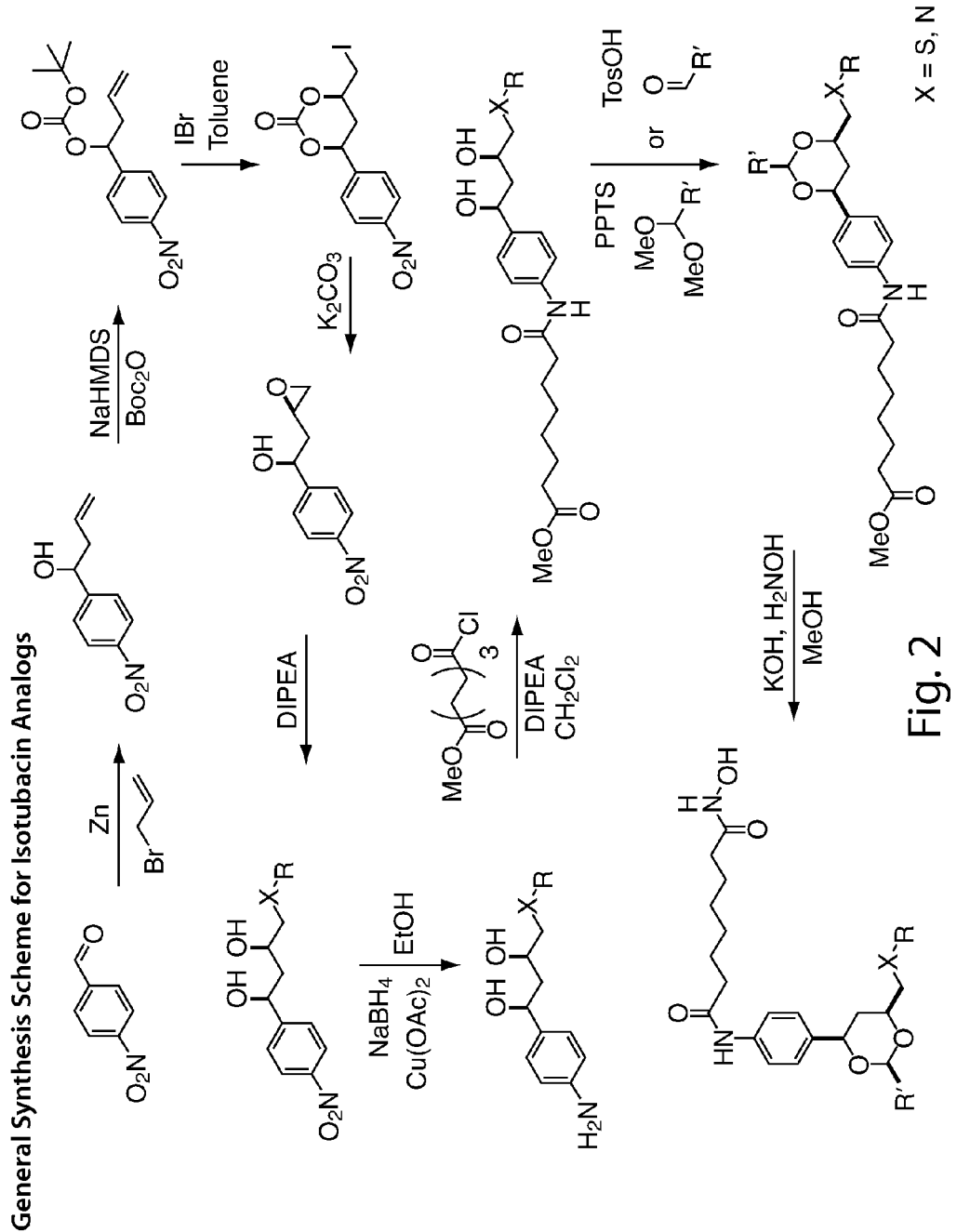
FIG. 2 shows a general synthetic scheme for compounds of the "isotubacin" class.
Figure 3:
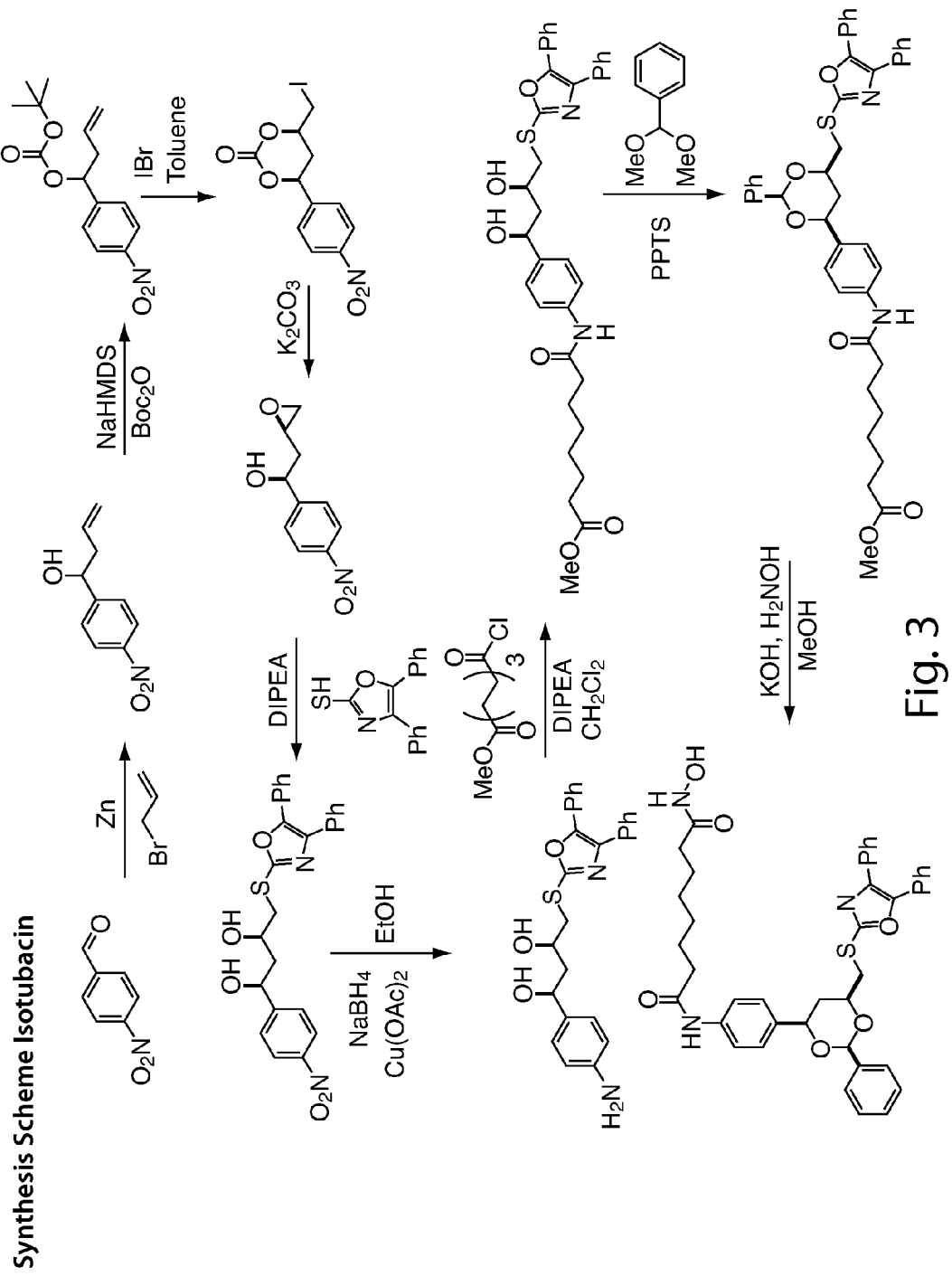
FIG. 3 shows an exemplary synthesis of isotubacin.

A general synthetic scheme for preparing compounds of this class is shown in FIG. 2. FIG. 3 is a synthetic scheme showing the synthesis of isotubacin.

In certain embodiments, the compounds of this second class are one of the formulae below with the stereochemistry as shown:

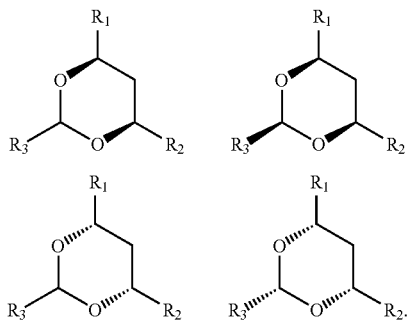

In certain embodiments, $R_1$ is a substituted phenyl ring. In certain particular embodiments, $R_1$ is of the formula:

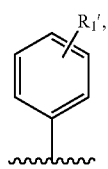

wherein $R_1'$ is

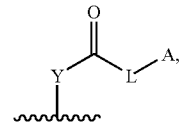

wherein Y is NH or O; L is a linker moiety; and A comprises a functional group that inhibits histone or tubulin deacetylase.

In certain embodiments, $R_1$ is of the formula:

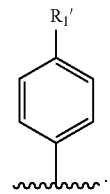

In other embodiments, $R_1$ is of the formula:

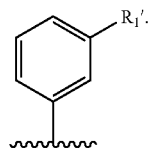

In certain embodiments, Y is NH. In other embodiments, Y is O. In certain embodiments, L is a substituted or unsubstituted, cyclic or acyclic, branched or unbranched aliphatic moiety; a substituted or unsubstituted, cyclic or acyclic, branched or unbranched heteroaliphatic moiety; a substituted or unsubstituted aryl moiety; a substituted or unsubstituted heteroaryl moiety. In certain embodiments, L is a substituted or unsubstituted, cyclic or acyclic, branched or unbranched aliphatic moiety. In certain embodiments, L is $C_1$-$C_{20}$ alkylidene, preferably $C_1$ to $C_{12}$ alkylidene, more preferably $C_4$-$C_7$ alkylidene. In certain embodiments, L is $C_1$-$C_{20}$ alkenylidene, preferably $C_1$ to $C_{12}$ alkenylidene, more preferably $C_4$-$C_7$ alkenylidene. In certain embodiments, L is $C_1$-$C_{20}$ alkynylidene, preferably $C_1$ to $C_{12}$ alkynylidene, more preferably $C_4$-$C_7$ alkynylidene. In certain embodiments, L is a substituted or unsubstituted, cyclic or acyclic, branched or unbranched heteroaliphatic moiety. In certain embodiments, L comprises a cyclic ring system, wherein the rings may be aryl, heteroaryl, non-aromatic carbocyclic, or non-aromatic heterocyclic. In still other embodiments, L comprises a substituted or unsubstituted heteroaryl moiety. In certain particular embodiments, L comprises a phenyl ring. In certain embodiments, L comprises multiple phenyl rings (e.g., one, two, three, or four phenyl rings).

In certain embodiments, L is

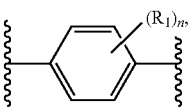

wherein n is an integer between 1 and 4, inclusive; preferably, between 1 and 3, inclusive; more preferably, 1 or 2; and $R_1$ is is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N(R_A)_2$; —$NHR_A$; —$NHC(O)R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, L is

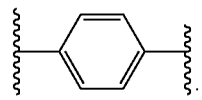

In certain embodiments, L is

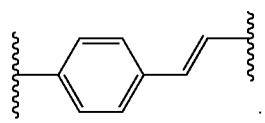

In certain embodiments, L is an unbranched, unsubstituted, acyclic alkyl chain. In certain embodiments, L is

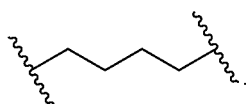

In other embodiments, L is

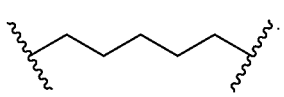

In certain other embodiments, L is

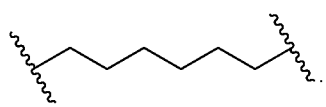

In other embodiments, L is

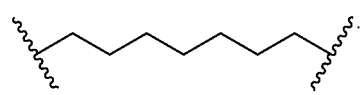

In yet other embodiments, L is

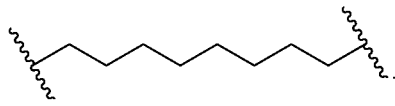

In certain embodiments, L is a substituted, acyclic aliphatic chain. In certain embodiments, L is

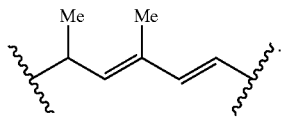

In certain embodiments, L is an unbranched, unsubstituted, acyclic heteroaliphatic chain. In certain particular embodiments, L is

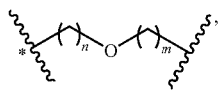

wherein n is an integer between 0 and 10, inclusive; preferably, between 0 and 5, inclusive; and m is an integer between 0 and 10, inclusive; preferably, between 0 and 5, inclusive. In certain particular embodiments, L is

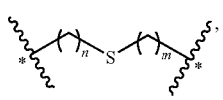

wherein n is an integer between 0 and 10, inclusive; preferably, between 0 and 5, inclusive; and m is an integer between 0 and 10, inclusive; preferably, between 0 and 5, inclusive. In certain particular embodiments, L is

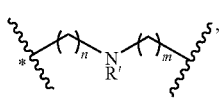

wherein n is an integer between 0 and 10, inclusive; preferably, between 0 and 5, inclusive; m is an integer between 0 and 10, inclusive; preferably, between 0 and 5, inclusive; and R' is hydrogen, $C_1$-$C_6$ aliphatic, heteroaliphatic, aryl, heteroaryl, or acyl. In certain particular embodiments, L is

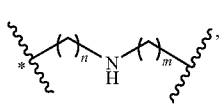

wherein n is an integer between 0 and 10, inclusive; preferably, between 0 and 5, inclusive; and m is an integer between 0 and 10, inclusive; preferably, between 0 and 5, inclusive. In certain embodiments, A comprises a metal chelating functional group. For example, A comprises a $Zn^{2+}$ chelating group. In certain embodiments, A comprises a functional group selected group consisting of:

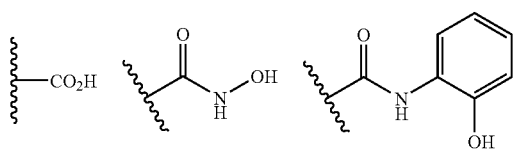 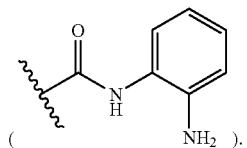

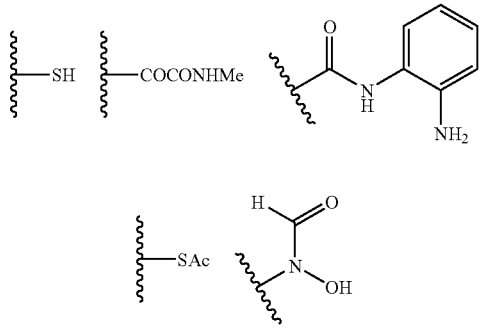

In other embodiments, A comprises an o-hydroxyanilide

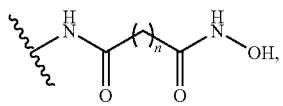

In yet other embodiments, A comprises a thiol (—SH). In certain embodiments, $R_1'$ is

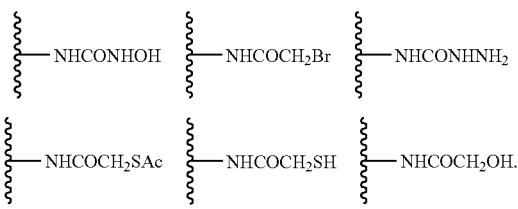

In certain embodiments, A comprises hydroxamic acid

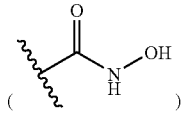

or a salt thereof. In other embodiments, A comprises the formula:

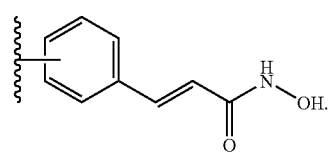

In certain particular embodiments, A comprises the formula:

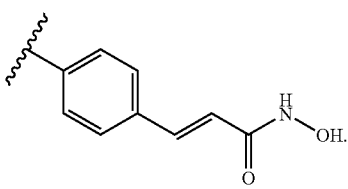

In other embodiments, A comprises a carboxylic acid (—CO$_2$H). In other embodiments, A comprises an o-aminoanilide

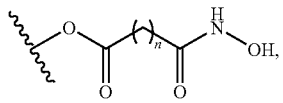

wherein n is an integer between 0 and 15, inclusive; preferably, between 0 and 10, inclusive; more preferably, between 1 and 8, inclusive; even more preferably, 4, 5, 6, 7, or 8. In certain embodiments, $R_1'$ is

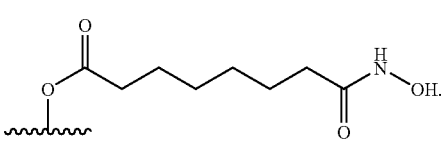

wherein n is an integer between 0 and 15, inclusive; preferably, between 0 and 10, inclusive; more preferably, between 1 and 8, inclusive; even more preferably, 4, 5, 6, 7, or 8. In certain embodiments, $R_1'$ is

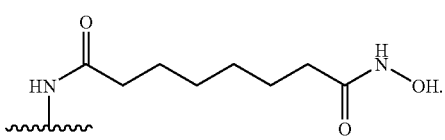

In other particular embodiments, $R_1'$ is

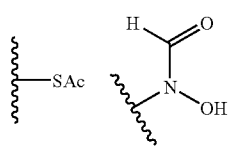

In certain embodiments, $R_2$ is hydrogen. In other embodiments, $R_2$ is hydroxyl or a protected hydroxyl group. In certain embodiments, $R_2$ is alkoxy. In yet other embodiments, $R_2$ is a lower alkyl, alkenyl, or alkynyl group. In certain embodiments, $R_2$ is —(CH$_2$)$_m$—X(R$_B$)$_n$, wherein X is O, S, N, or C, preferably O, S, or N; n is 1, 2, or 3; and m is an integer between 1 and 6, inclusive. In certain embodiments, $R_2$ is —CH$_2$—X(R$_B$)$_n$, wherein X is O, S, N, or C, preferably O, S, or N; and n is 1, 2, or 3. In certain embodiments, R$_2$ is —CH$_2$—OR$_B$. In other embodiments, R$_2$ is —CH$_2$—SR$_B$. In yet other embodiments, R$_2$ is —CH$_2$—R$_B$. In other embodiments, R$_2$ is —CH$_2$—N(R$_B$)$_2$. In still other embodiments, R$_2$ is —CH$_2$—NHR$_B$. In certain embodiments of the invention, R$_B$ is one of:

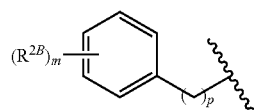
a

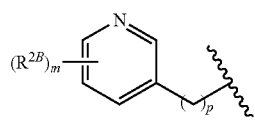
b

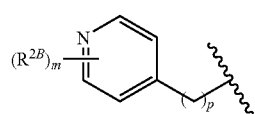
c

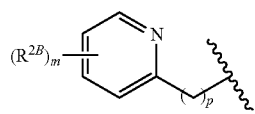
d

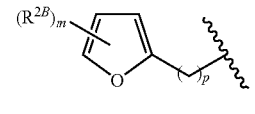
e

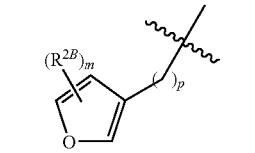
f

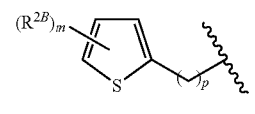
g

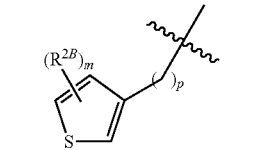
h

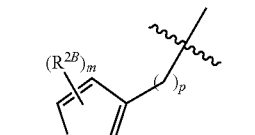
i

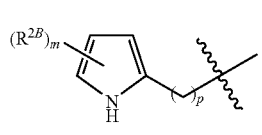
j

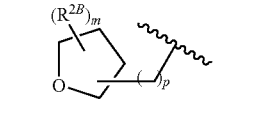
k

-continued

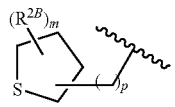
l

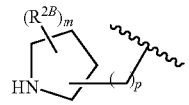
m

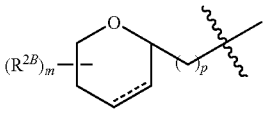
n

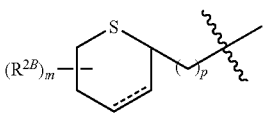
o

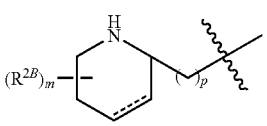
p

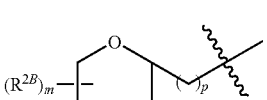
q

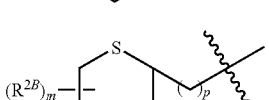
r

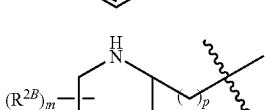
s

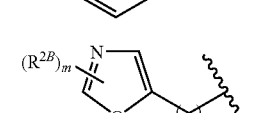
t

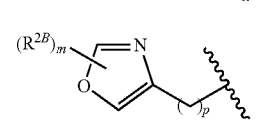
u

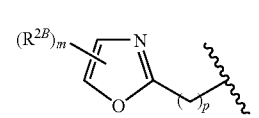
v

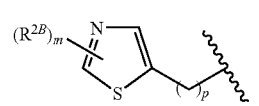
w

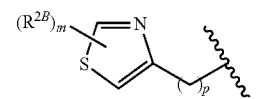
x

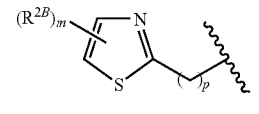
y

-continued

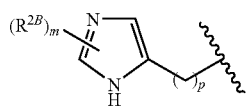 z

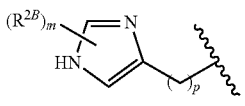 aa

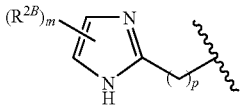 bb

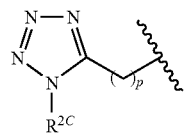 cc

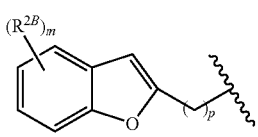 dd

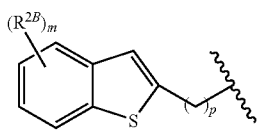 ee

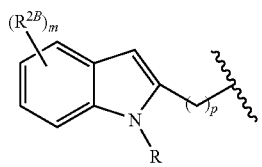 ff

R = H, Alkyl

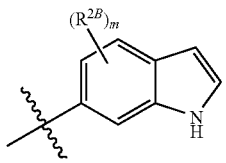 gg

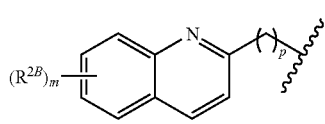 hh

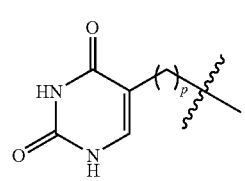 ii

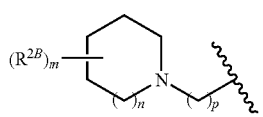 jj n = 0 or 1

-continued

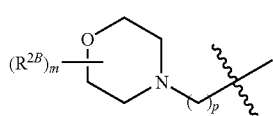 kk

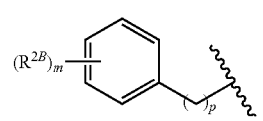 ll

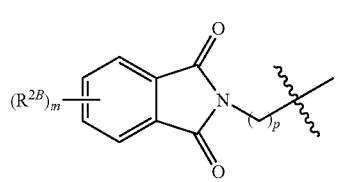 mm

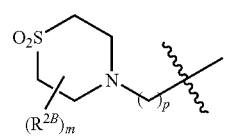 nn

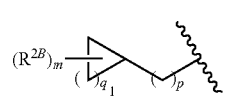 oo wherein m and p are each independently integers from 0 to 3; $q_1$ is an integer from 1 to 6; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —SO$_2$, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety. In certain embodiments of the invention, $R_B$ is one of the structures:

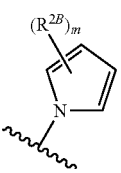 pp

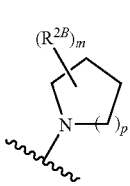 qq

-continued

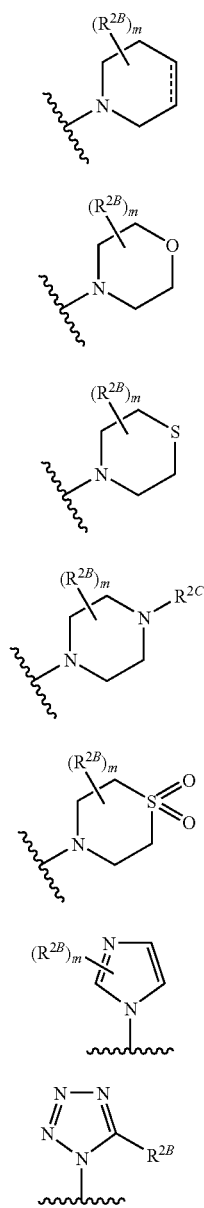

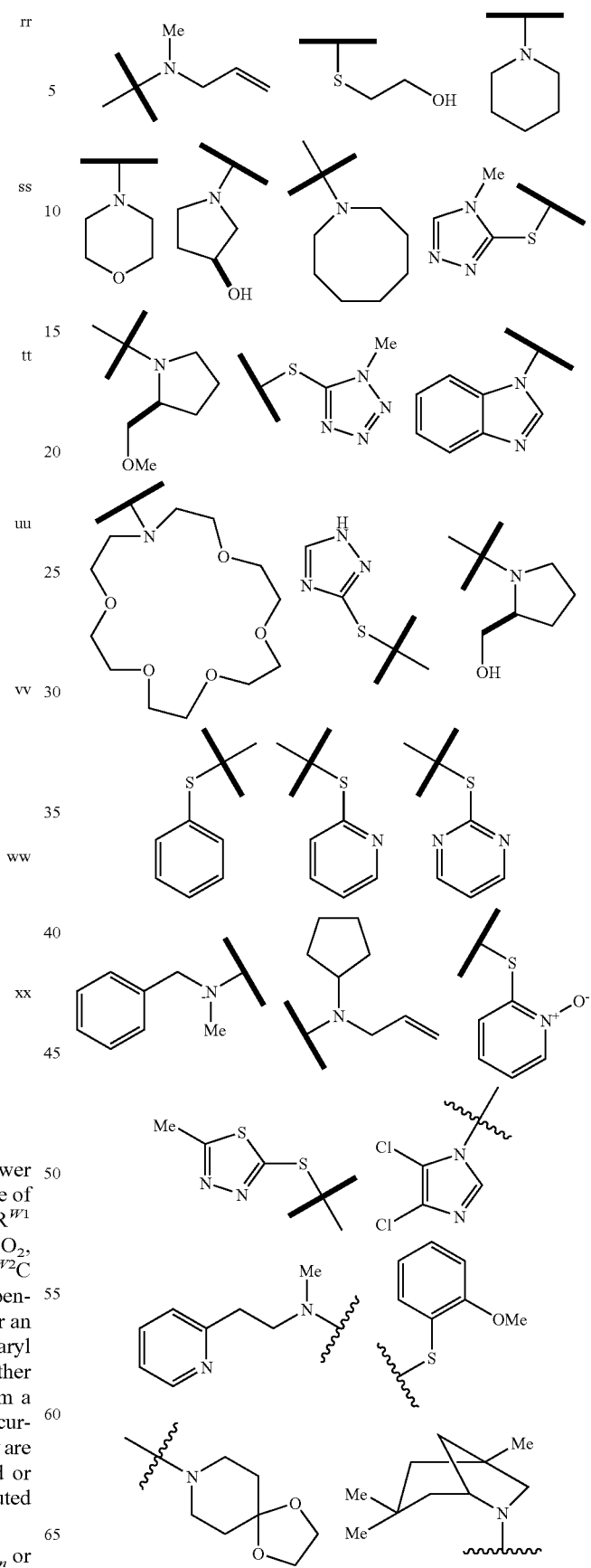

wherein m is an integer from 1 to 4; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O—O), —S(=O), —SO$_2$, —C(=O)O—, —OC(=O), —C(=O)$NR^{W2}$, —$NR^{W2}$C (=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety.

In certain embodiments, —X(R$_B$)$_n$ of —CH$_2$—X(R$_B$)$_n$ or —(CH$_2$)$_m$—X(R$_B$)$_n$ has one of the structures:

-continued
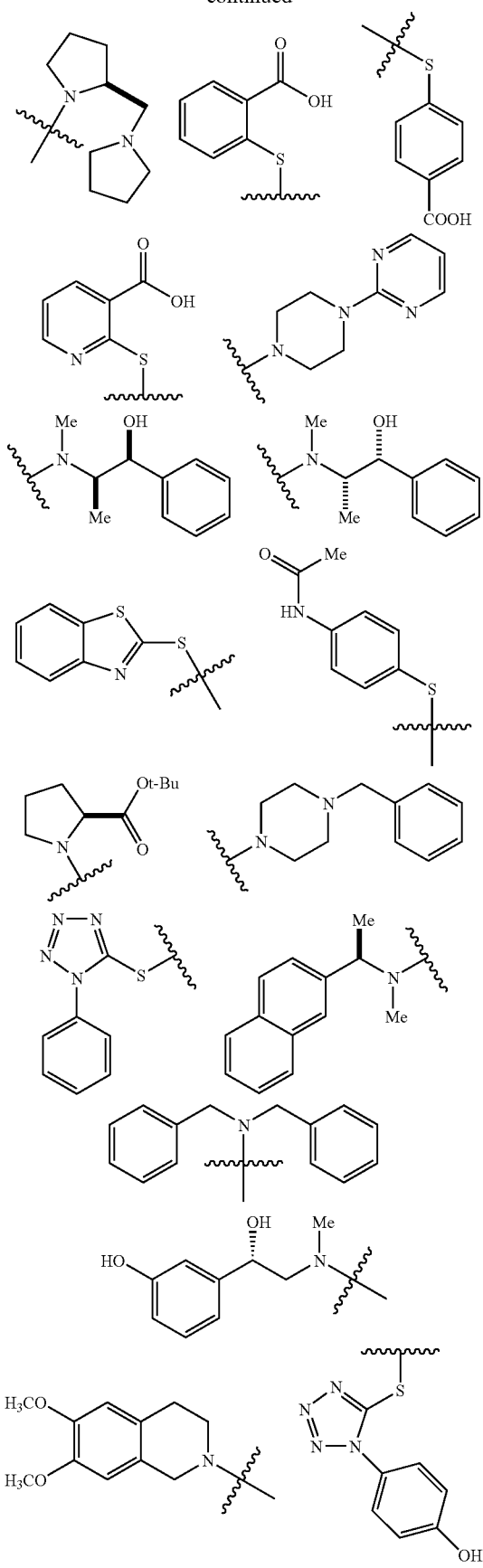
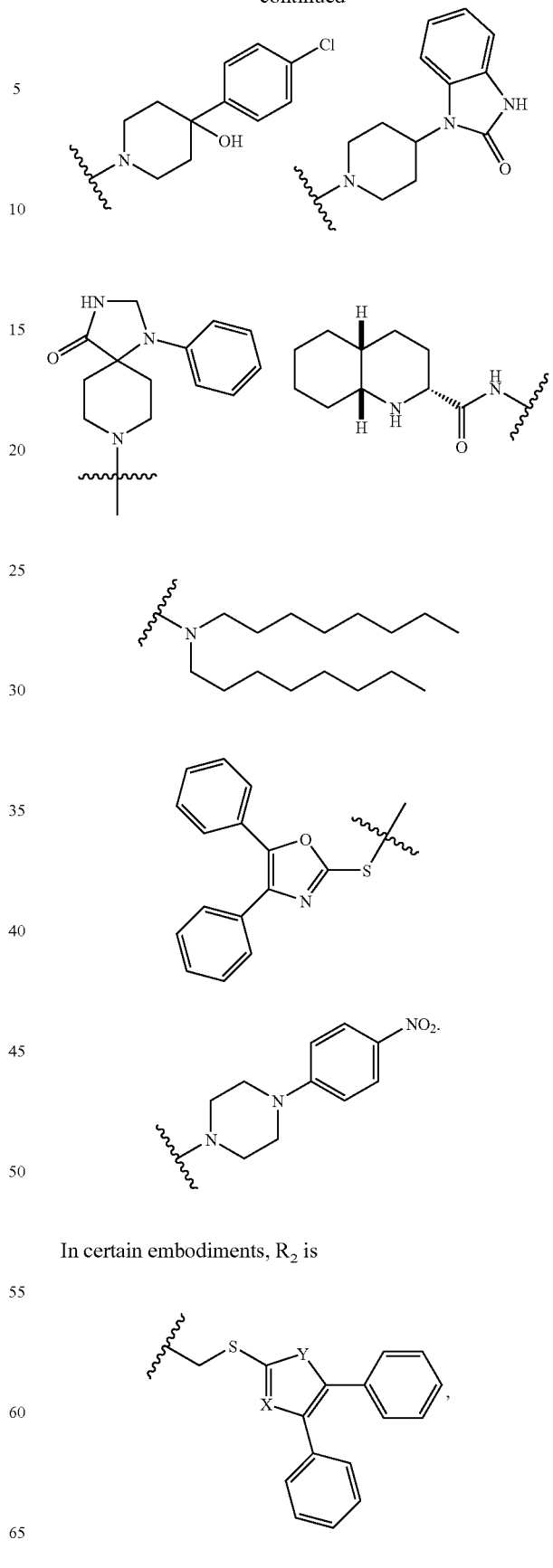
In certain embodiments, $R_2$ is
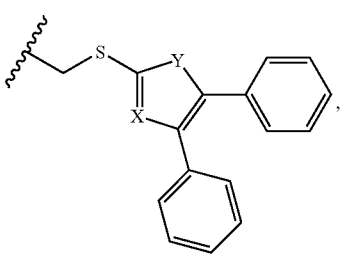

wherein X is N and Y is NH, S, or O. In other embodiments, R₂ is

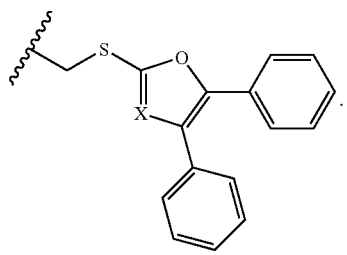

In certain embodiments, R₂ is selected from one of the following:

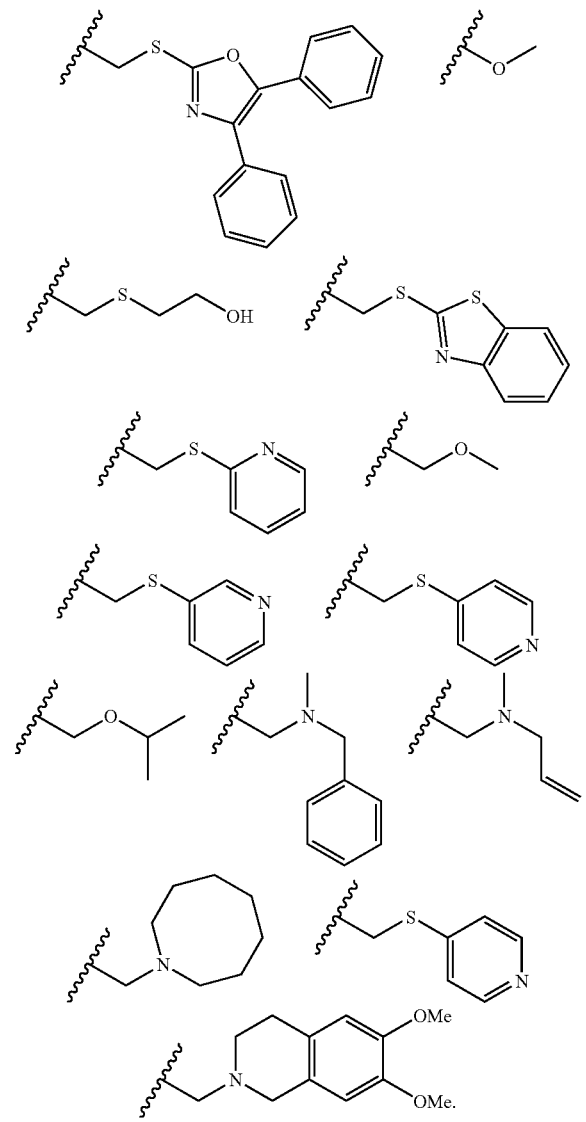

In certain embodiments, R₃ is aliphatic. In other embodiments, R₃ is heteroaliphatic. In certain embodiments, R₃ is a substituted or unsubstituted aryl moiety. In certain embodiments, R₃ is a substituted or unsubstituted heteroaromatic moiety. In certain embodiments, R₃ is a monocyclic moiety. In other embodiments, R₃ is a bicyclic moiety. In yet other embodiments, R₃ is a tricyclic moiety. In yet other embodiments, R₃ is a polycyclic moiety. In certain embodiments, R₃ is a substituted or unsubstituted five- or six-membered aromatic or heteroaromatic moiety. In certain embodiments, R₃ is a substituted or unsubstituted six-membered aromatic or heteroaromatic moiety. In certain embodiments, R₃ is a substituted or unsubstituted six-membered aromatic moiety. In certain embodiments, R₃ is a substituted or unsubstituted six-membered heteroaromatic moiety. In certain embodiments, R₃ is a substituted or unsubstituted non-aromatic carbocyclic or heterocyclic moiety. In certain embodiments, R₃ is substituted or unsubstituted aryl. In certain embodiments, R₃ is substituted or unsubstituted phenyl. In certain embodiments, R₃ is

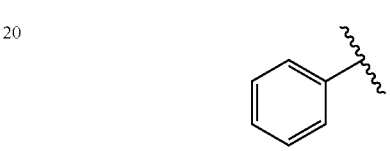

In certain particular embodiments, R₃ is monosubstituted phenyl. In certain embodiments, R₃ is para-substituted phenyl. In certain embodiments, R₃ is

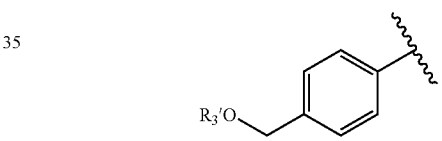

wherein R₃' is hydrogen, a protecting group, a solid support unit, an alkyl, acyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety. In certain embodiments, R₃ is

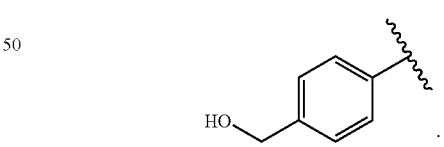

In certain embodiments, R₃ is not

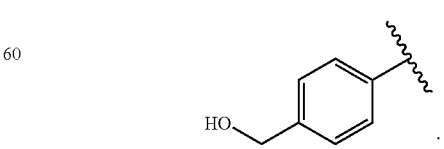

In other embodiments, R₃ is substituted or unsubstituted heteroaryl.

In certain embodiments, the invention provides compounds of the formula:

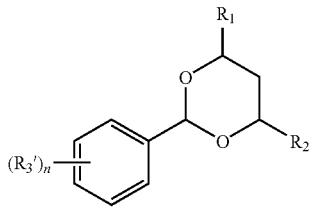

wherein $R_1$ and $R_2$ are defined as above;
n is an integer between 1 and 5, inclusive; and
each occurrence of $R_3'$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In certain embodiments, n is 0, and the phenyl ring is unsubstituted.

In other embodiments, n is 1, and the compounds are one of the formulae:

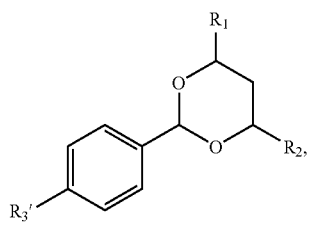

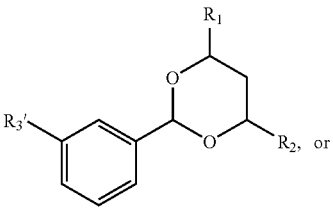

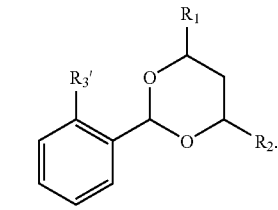

In certain embodiments, the para-substitution pattern is preferred. In other embodiments, the meta-substitution pattern is preferred. And in yet other embodiments, the ortho-substitution pattern is preferred.

In other embodiments, n is 2. Compounds of the invention include compounds of one of the formulae:

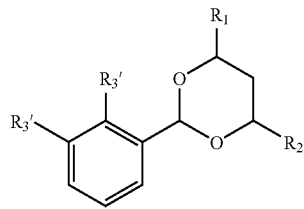

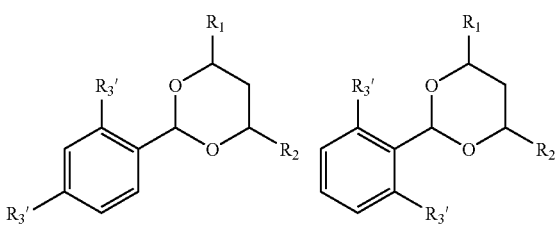

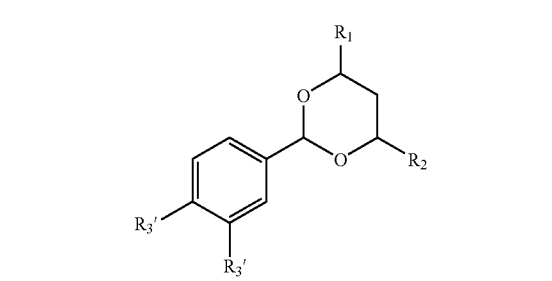

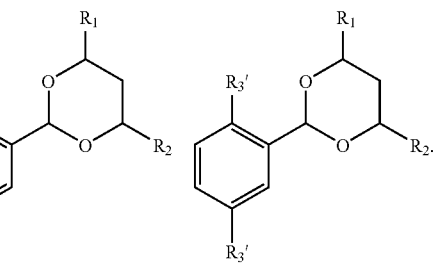

In other embodiments, n is 3. In still other embodiments, n is 4, and in other embodiments, n is 5.

In certain embodiments, $R_3'$ is halogen, hydroxyl, protected hydroxyl, alkoxy, amino, alkylamino, dialkylamino, —$NO_2$, $C_1$-$C_6$ alkyl, $C_1$-$C_6$ alkenyl, $C_1$-$C_6$ alkynyl, or acyl. In certain embodiments, $R_3'$ is —$NO_2$. In certain embodiments, $R_3'$ is —$CH_2OH$. In certain embodiments, $R_3'$ is —$NH_2$. In certain embodiments, $R_3'$ is —H. In other embodiments, $R_3'$ is —OH. In other embodiments, $R_3'$ is —CN. In yet other embodiments, $R_3'$ is —SCN. In still other embodiments, $R_3'$ is acyl. In certain embodiments, $R_3'$ is acetyl. In other embodiments, $R_3'$ is —F. In other embodiments, $R_3'$ is Cl. In other embodiments, $R_3'$ is —Br. In other embodiments, $R_3'$ is —I. In other embodiments, $R_3'$ is methyl, ethyl, n-propyl, iso-propyl, n-butyl, tert-butyl, or iso-butyl. In certain embodiments, $R_3'$ is vinyl. In certain embodiments, $R_3'$ is halogen-substituted alkyl (e.g., trifluoromethyl). In certain embodiments, $R_3'$ is methoxy, ethyoxy, propoxy, butoxy, or pentoxy.

Exemplary compounds of this second "isotubacin" class include compounds of the formula:

35
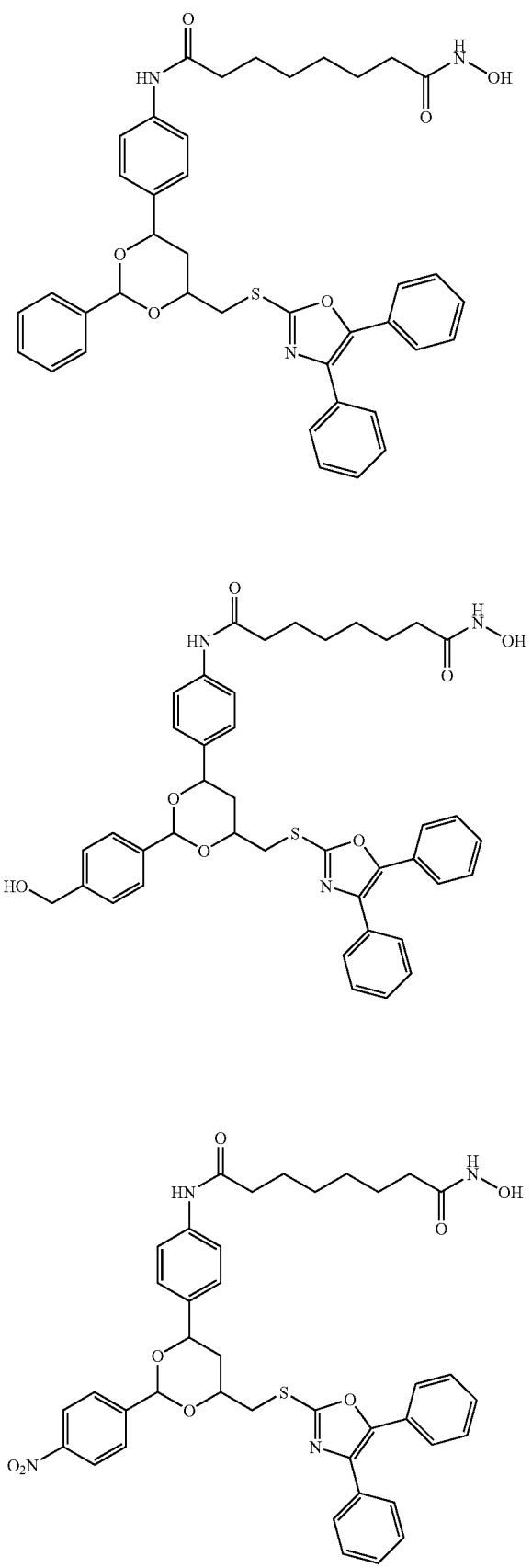
36
-continued
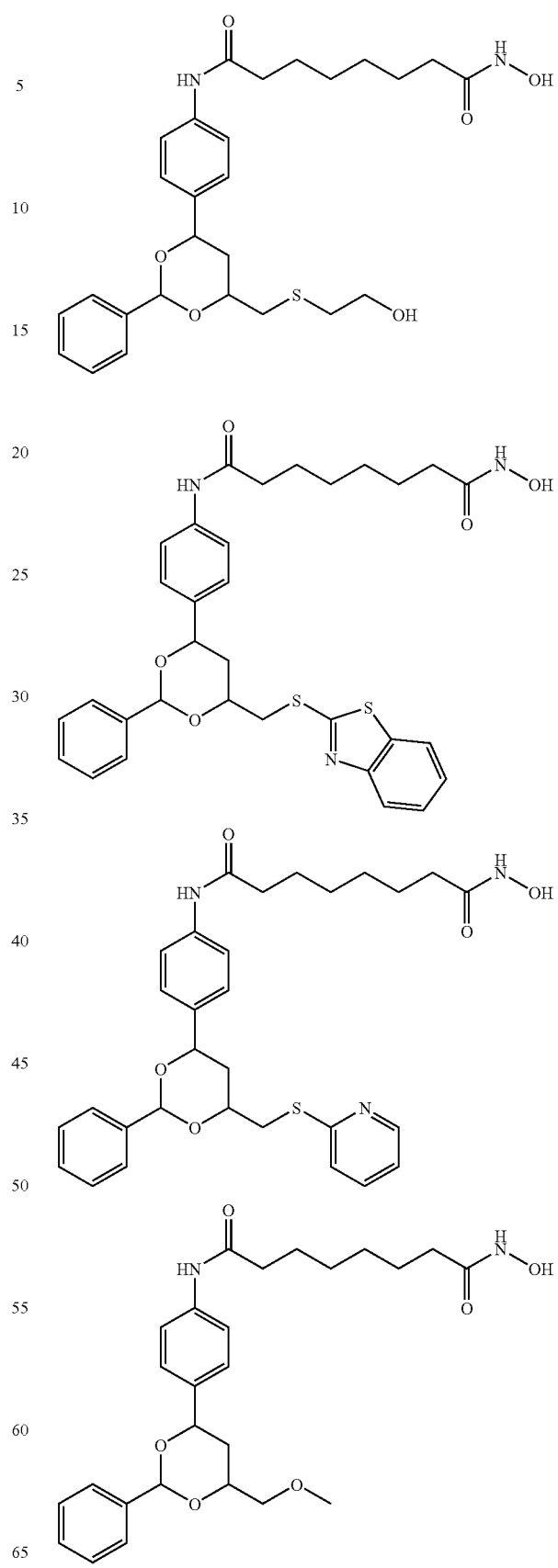

-continued

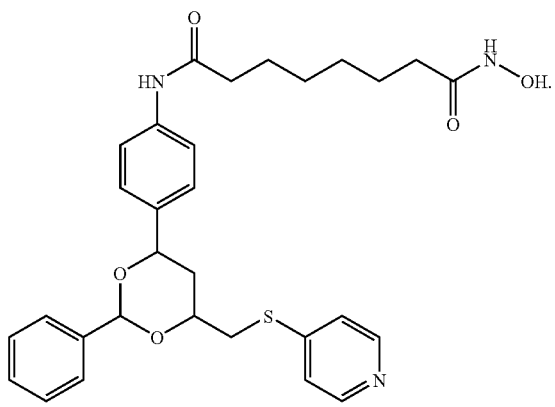

The invention also provides compounds of the isoisotubacin class. These compounds are of the formula:

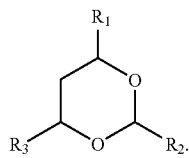

Figure 4:
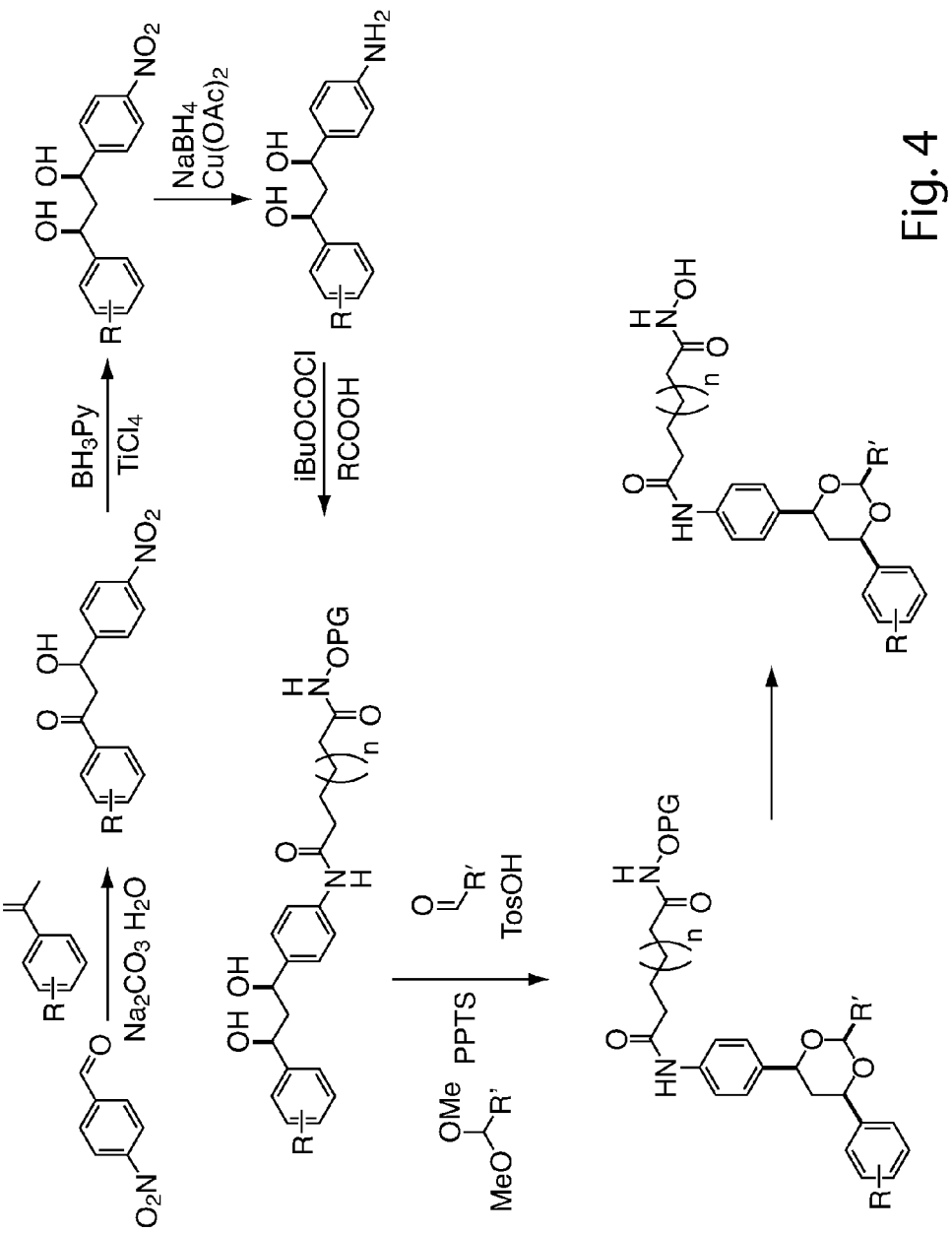
FIG. 4 shows a general synthetic scheme for compounds of the "isoisotubacin" class.
Figure 5:
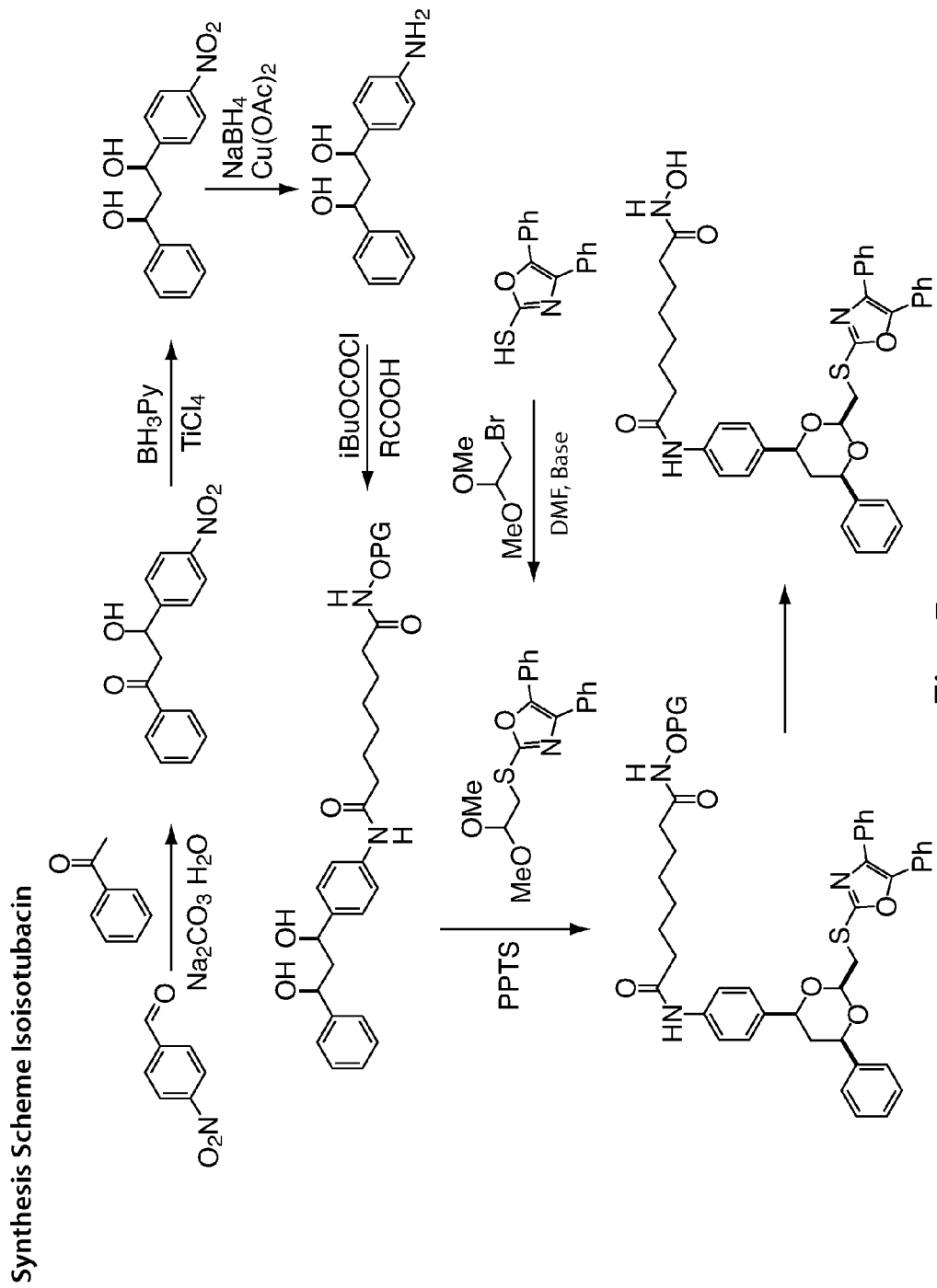
FIG. 5 shows an exemplary synthesis of isoisotubacin.

A general synthetic scheme for preparing compounds of this class is shown in FIG. 4. FIG. 5 is a synthetic scheme showing the synthesis of isoisotubacin.

In certain embodiments, the compounds of this second class are one of the formulae below with the stereochemistry as shown:

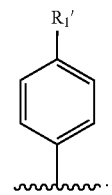

In certain embodiments, $R_1$ is a substituted phenyl ring. In certain particular embodiments, $R_1$ is of the formula:

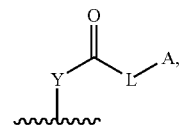

wherein $R_1'$ is

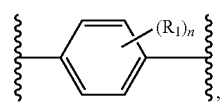

wherein Y is NH or O; L is a linker moiety; and A comprises a functional group that inhibits histone deacetylase.

In certain embodiments, $R_1$ is of the formula:

In other embodiments, $R_1$ is of the formula:

In certain embodiments, Y is NH. In other embodiments, Y is O. In certain embodiments, L is a substituted or unsubstituted, cyclic or acyclic, branched or unbranched aliphatic moiety; a substituted or unsubstituted, cyclic or acyclic, branched or unbranched heteroaliphatic moiety; a substituted or unsubstituted aryl moiety; a substituted or unsubstituted heteroaryl moiety. In certain embodiments, L is a substituted or unsubstituted, cyclic or acyclic, branched or unbranched aliphatic moiety. In certain embodiments, L is $C_1$-$C_{20}$ alkylidene, preferably $C_1$ to $C_{12}$ alkylidene, more preferably $C_4$-$C_7$ alkylidene. In certain embodiments, L is $C_1$-$C_{20}$ alkenylidene, preferably $C_1$ to $C_{12}$ alkenylidene, more preferably $C_4$-$C_7$ alkenylidene. In certain embodiments, L is $C_1$-$C_{20}$ alkynylidene, preferably $C_1$ to $C_{12}$ alkynylidene, more preferably $C_4$-$C_7$ alkynylidene. In certain embodiments, L is a substituted or unsubstituted, cyclic or acyclic, branched or unbranched heteroaliphatic moiety. In certain embodiments, L comprises a cyclic ring system, wherein the rings may be aryl, heteroaryl, non-aromatic carbocyclic, or non-aromatic heterocyclic. In still other embodiments, L comprises a substituted or unsubstituted heteroaryl moiety. In certain particular embodiments, L comprises a phenyl ring. In certain embodiments, L comprises multiple phenyl rings (e.g., one, two, three, or four phenyl rings).

In certain embodiments, L is wherein n is an integer between 1 and 4, inclusive; preferably, between 1 and 3, inclusive; more preferably, 1 or 2; and $R_1$ is is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N(R_A)_2$; —$NR_A$; —$NHC(O)R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, L is

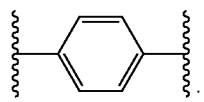

In certain embodiments, L is

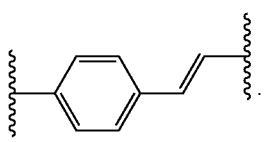

In certain embodiments, L is an unbranched, unsubstituted, acyclic alkyl chain. In certain embodiments, L is

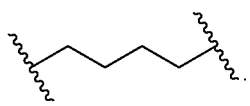

In other embodiments, L is

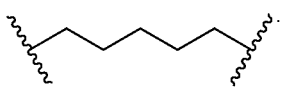

In certain other embodiments, L is

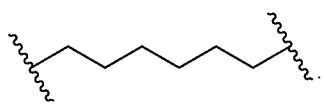

In other embodiments, L is

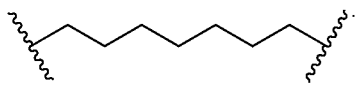

In yet other embodiments, L is

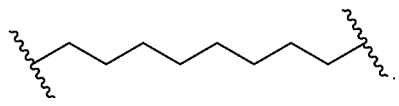

In certain embodiments, L is a substituted, acyclic aliphatic chain. In certain embodiments, L is

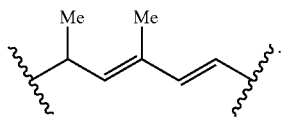

In certain embodiments, L is an unbranched, unsubstituted, acyclic heteroaliphatic chain. In certain particular embodiments, L is

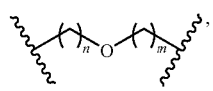

wherein n is an integer between 0 and 10, inclusive; preferably, between 0 and 5, inclusive; and m is an integer between 0 and 10, inclusive; preferably, between 0 and 5, inclusive. In certain particular embodiments, L is

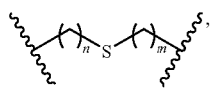

wherein n is an integer between 0 and 10, inclusive; preferably, between 0 and 5, inclusive; and m is an integer between 0 and 10, inclusive; preferably, between 0 and 5, inclusive. In certain particular embodiments, L is

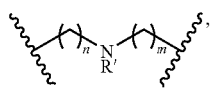

wherein n is an integer between 0 and 10, inclusive; preferably, between 0 and 5, inclusive; m is an integer between 0 and 10, inclusive; preferably, between 0 and 5, inclusive; and R' is hydrogen, $C_1$-$C_6$ aliphatic, heteroaliphatic, aryl, heteroaryl, or acyl. In certain particular embodiments, L is

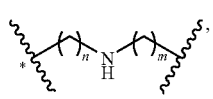

wherein n is an integer between 0 and 10, inclusive; preferably, between 0 and 5, inclusive; and in is an integer between 0 and 10, inclusive; preferably, between 0 and 5, inclusive. In certain embodiments, A comprises a metal chelating functional group. For example, A comprises a $Zn^{2+}$ chelating group. In certain embodiments, A comprises a functional group selected group consisting of:

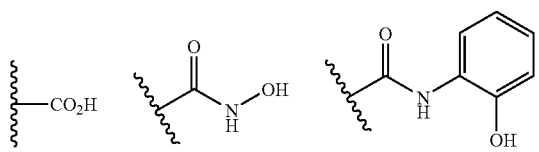
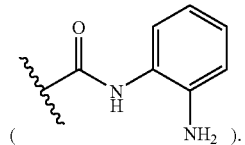
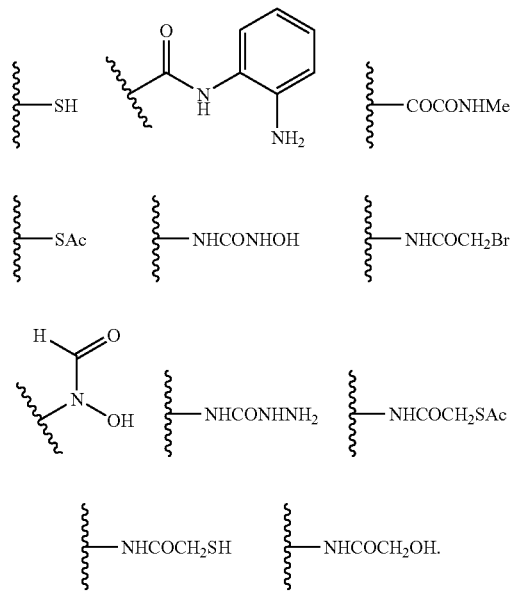

In certain embodiments, A comprises hydroxamic acid

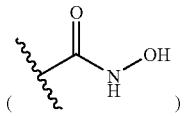

or a salt thereof. In other embodiments, A comprises the formula:

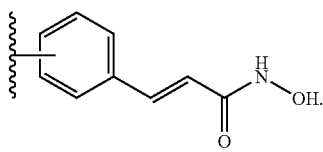

In certain particular embodiments, A comprises the formula:

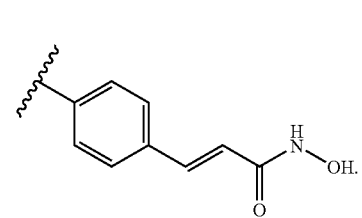

In other embodiments, A comprises a carboxylic acid (—CO$_2$H). In other embodiments, A comprises an o-aminoanilide

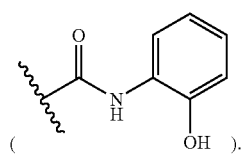

In other embodiments, A comprises an o-hydroxyanilide

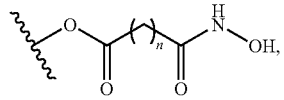

In yet other embodiments, A comprises a thiol (—SH). In certain embodiments, $R_1$' is

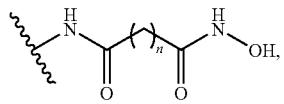

wherein n is an integer between 0 and 15, inclusive; preferably, between 0 and 10, inclusive; more preferably, between 1 and 8, inclusive; even more preferably, 4, 5, 6, 7, or 8. In certain embodiments, $R_1$' is

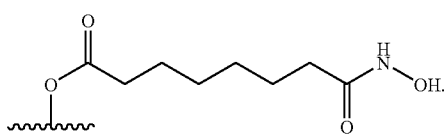

wherein n is an integer between 0 and 15, inclusive; preferably, between 0 and 10, inclusive; more preferably, between 1 and 8, inclusive; even more preferably, 4, 5, 6, 7, or 8. In certain embodiments, $R_1$' is

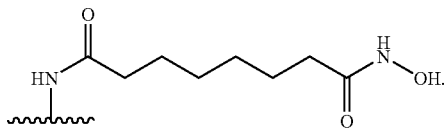

In other particular embodiments, $R_1$' is

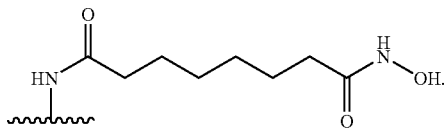

In certain embodiments, $R_2$ is hydrogen. In other embodiments, $R_2$ is hydroxyl or a protected hydroxyl group. In certain embodiments, $R_2$ is alkoxy. In yet other embodiments, $R_2$ is a lower alkyl, alkenyl, or alkynyl group. In certain embodiments, $R_2$ is —CH$_2$—X(R$_B$)$_n$, wherein X is O, S, N, or C, preferably O, S, or N; and n is 1, 2, or 3. In certain embodiments, $R_2$ is —CH$_2$—OR$_B$. In other embodiments, $R_2$ is —$CH_2$—$SR_B$. In yet other embodiments, $R_2$ is —$CH_2$—$R_B$. In other embodiments, $R_2$ is —$CH_2$—$N(R_B)_2$. In still other embodiments, $R_2$ is —$CH_2$—$NHR_B$. In certain embodiments of the invention, $R_B$ is one of:
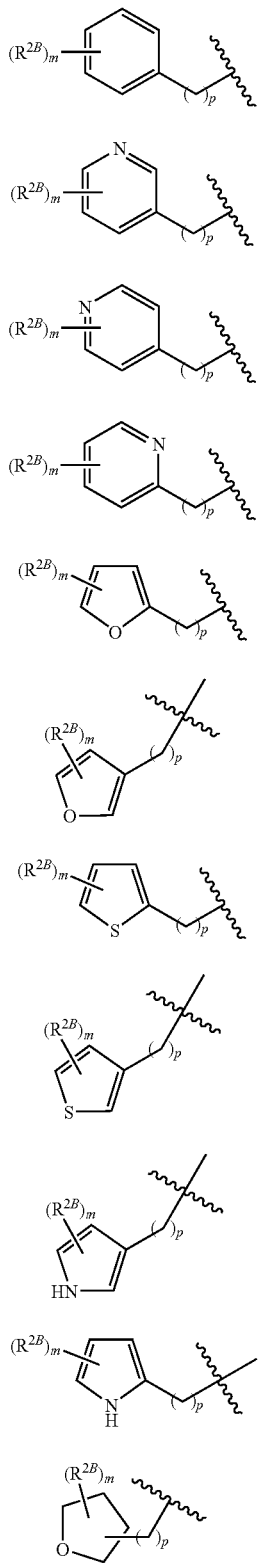
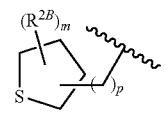
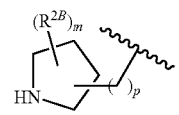
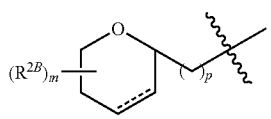
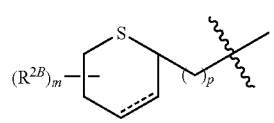
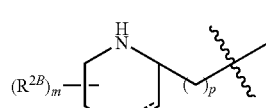
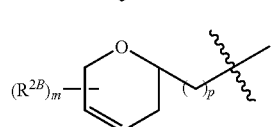
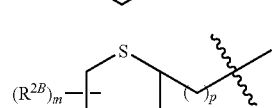
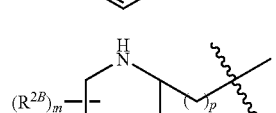
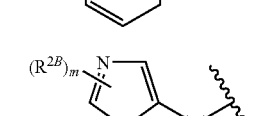
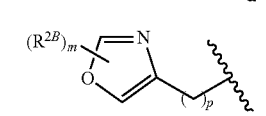
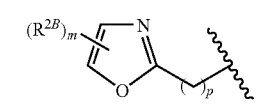
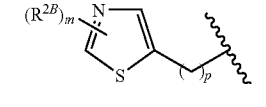
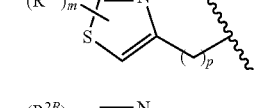

z
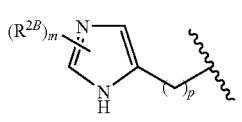

aa
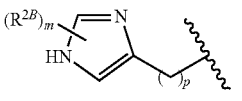

bb
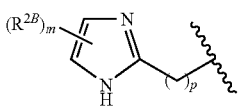

cc
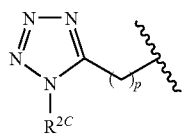

dd
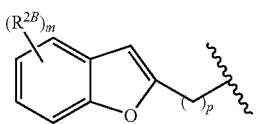

ee
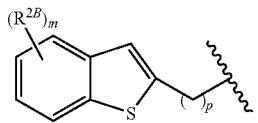

ff
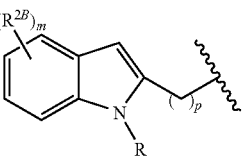

R = H, Alkyl gg
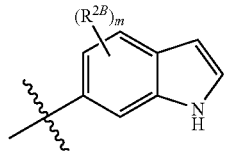

hh
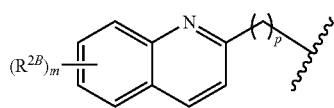

ii
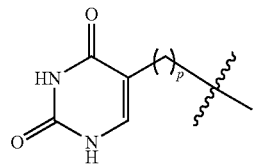

jj
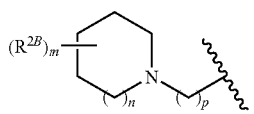

kk
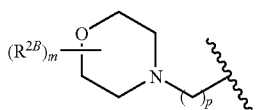

ll
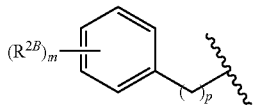

mm
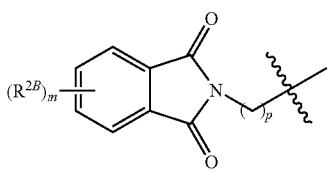

nn
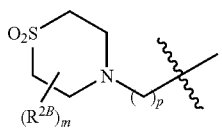

oo
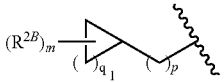

wherein m and p are each independently integers from 0 to 3; $q_1$ is an integer from 1 to 6; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —$SO_2$, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety. In certain embodiments of the invention, $R_B$ is one of the structures:

pp

qq
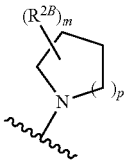

rr
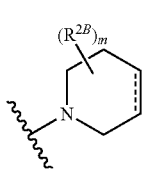

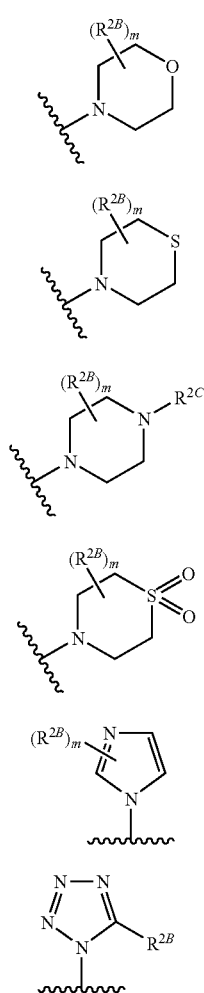
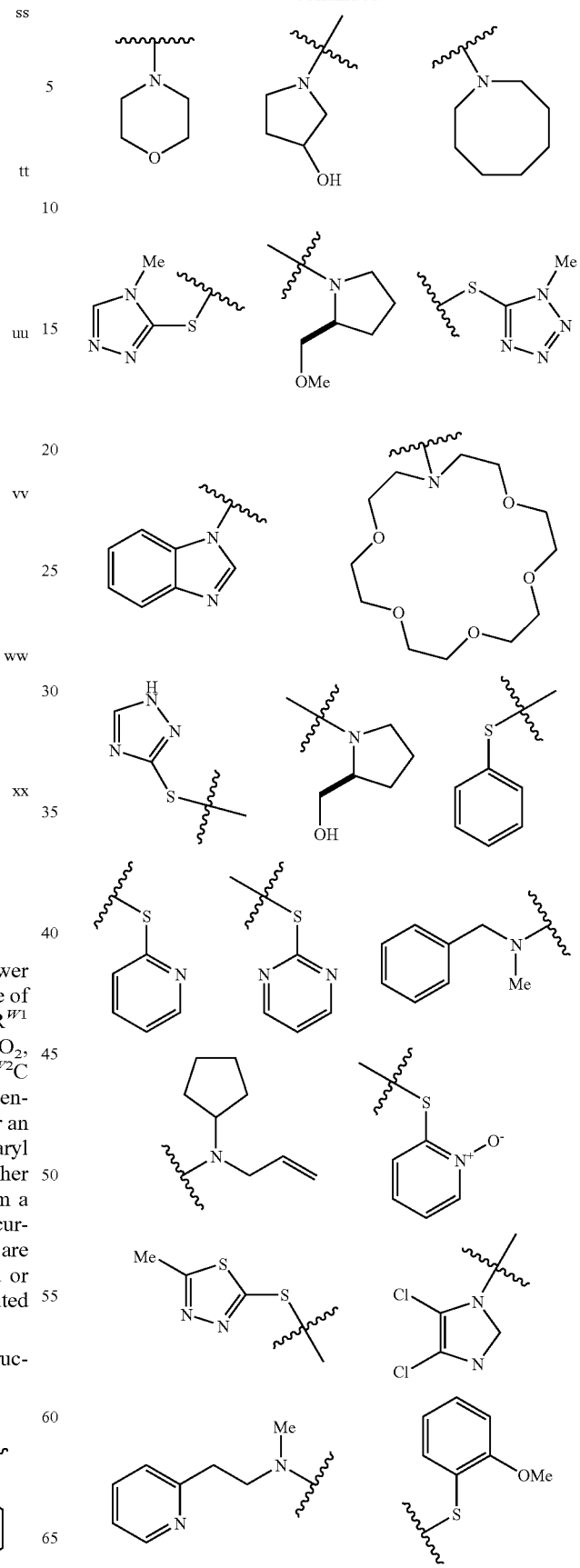

wherein m is an integer from 1 to 4; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —SO$_2$, —C(=O)O—, —OC(=O), —C(=O)$NR^{W2}$, —$NR^{W2}$C (=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety.

In certain embodiments, —X(R$_B$)$_n$ has one of the structures:

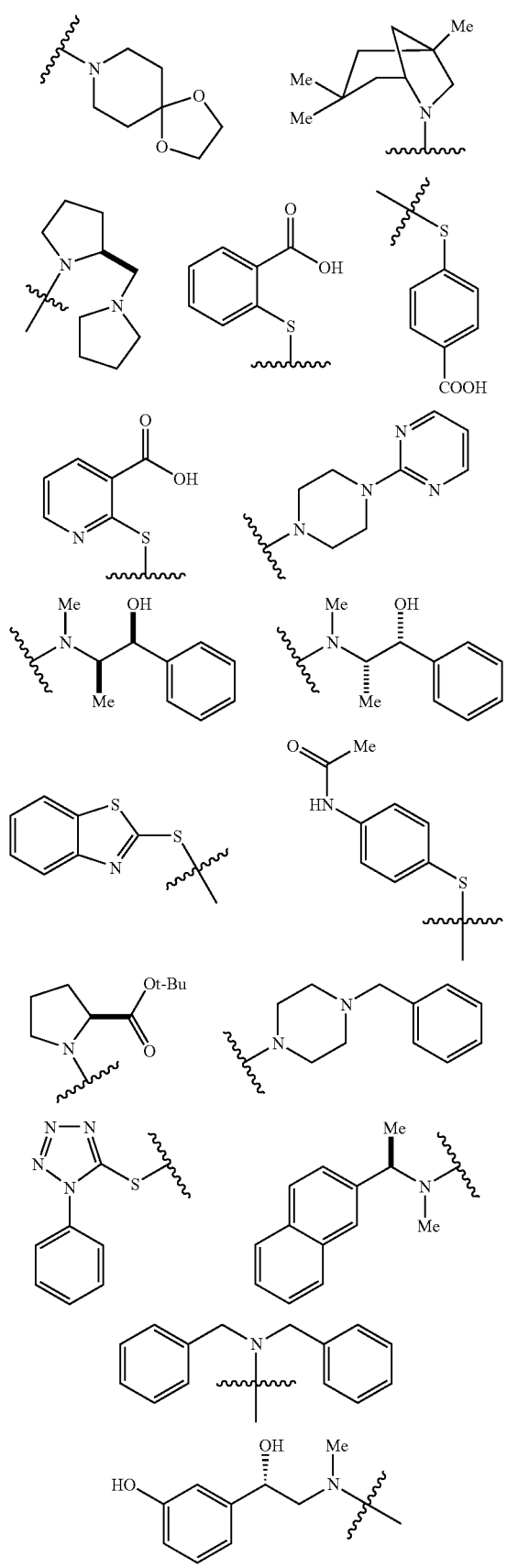
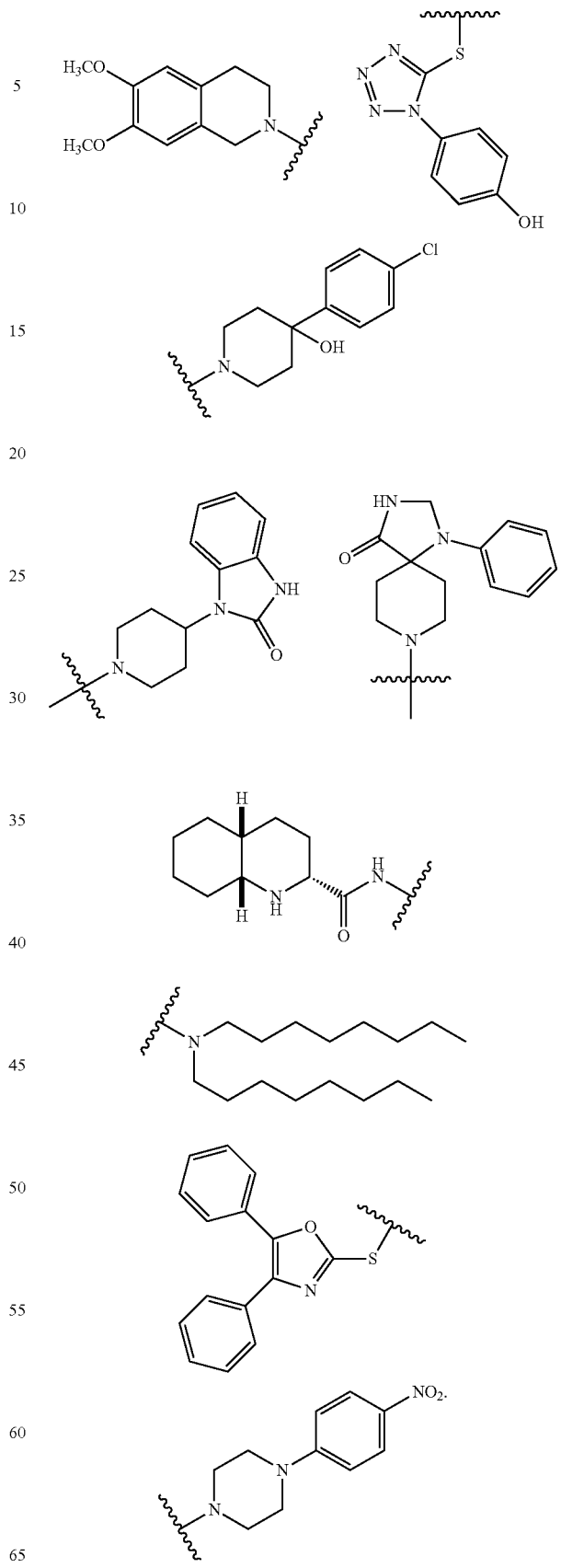

In certain embodiments, R$_2$ is

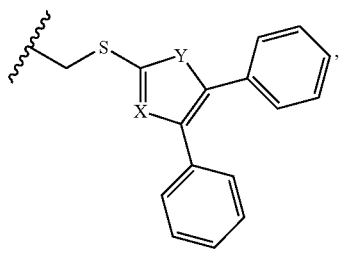

wherein X is N and Y is NH, S, or O. In other embodiments, R$_2$ is

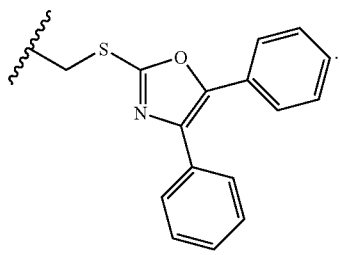

In certain embodiments, R$_2$ is selected from one of the following:

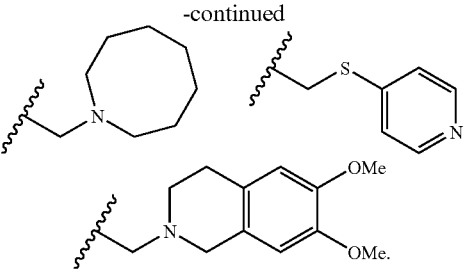

In certain embodiments, R$_2$ is a substituted or unsubstituted aryl or heteroaryl moiety. In certain embodiments, R$_2$ is a substituted or unsubstituted carbocyclic or heterocyclic moiety. The ring system of R$_2$ may be monocyclic, bicyclic, tricyclic, or polycyclic. The rings making up the ring system may be three-membered (e.g., oxiranyl, cyclopropyl, aziridinyl); four-membered; five-membered; six-membered; seven-membered; eight-membered; or n-membered. In bicyclic, tricyclic, or polycyclic ring systems, the rings may be fused, spiro-linked, or linked via a covalent bond. In certain embodiments, R$_2$ is a substituted or unsubstituted, monocyclic aryl moiety. In certain embodiments, R$_2$ is a substituted or unsubstituted, monocyclic phenyl moiety. In certain embodiments, R$_2$ is a substituted, monocyclic phenyl moiety. In certain embodiments, R$_2$ is unsubstituted phenyl. In certain embodiments, R$_2$ is a monosubstituted phenyl moiety. In other embodiments, R$_2$ is a disubstituted phenyl moiety. In yet other embodiments, R$_2$ is a trisubstituted phenyl moiety. In other embodiments, R$_2$ is a substituted or unsubstituted, monocyclic heteroaryl moiety. In certain embodiments, R$_2$ is a substituted or unsubstituted pyridinyl moiety. In certain embodiments, R$_2$ is a substituted or unsubstituted pyrrolyl moiety. In certain embodiments, R$_2$ is a substituted or unsubstituted imidazolyl moiety. In certain embodiments, R$_2$ is a substituted or unsubstituted thiazolyl moiety. In certain embodiments, R$_2$ is a substituted or unsubstituted oxazolyl moiety. In certain embodiments, R$_2$ is a substituted or unsubstituted furanyl moiety. In certain embodiments, R$_2$ is a substituted or unsubstituted thiophenyl moiety. In certain embodiments, R$_2$ is a substituted or unsubstituted, monocyclic carbocyclic moiety. In certain embodiments, R$_2$ is a substituted or unsubstituted, cyclopentyl moiety. In certain embodiments, R$_2$ is a substituted or unsubstituted, cyclohexyl moiety. In certain embodiments, R$_2$ is a substituted or unsubstituted, monocyclic heterocyclic moiety. In certain embodiments, R$_2$ is a substituted or unsubstituted, piperidinyl moiety. In certain embodiments, R$_2$ is a substituted or unsubstituted, pyrrolidinyl moiety.

In certain embodiments, R$_3$ is a substituted or unsubstituted aryl moiety. In certain embodiments, R$_3$ is a substituted or unsubstituted heteroaromatic moiety. In certain embodiments, R$_3$ is a monocyclic moiety. In other embodiments, R$_3$ is a bicyclic moiety. In yet other embodiments, R$_3$ is a tricyclic moiety. In yet other embodiments, R$_3$ is a polycyclic moiety. In certain embodiments, R$_3$ is a substituted or unsubstituted five- or six-membered aromatic or heteroaromatic moiety. In certain embodiments, R$_3$ is a substituted or unsubstituted six-membered aromatic or heteroaromatic moiety. In certain embodiments, R$_3$ is a substituted or unsubstituted six-membered aromatic moiety. In certain embodiments, R$_3$ is a substituted or unsubstituted six-membered heteroaromatic moiety. In certain embodiments, R$_3$ is a substituted or unsubstituted non-aromatic carbocyclic or heterocyclic moiety. In certain embodiments, R$_3$ is unsubstituted aryl. In certain embodiments, R$_3$ is substituted aryl. In certain embodiments, $R_3$ is substituted or unsubstituted phenyl. In certain particular embodiments, $R_3$ is monosubstituted phenyl. In certain embodiments, $R_3$ is

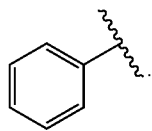

In certain embodiments, $R_3$ is para-substituted phenyl. In certain embodiments, $R_3$ is

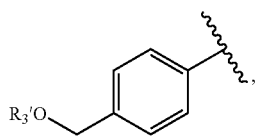

wherein $R_3'$ is hydrogen, a protecting group, a solid support unit, an alkyl, acyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety. In certain embodiments, $R_3$ is

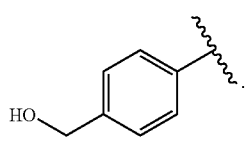

In certain embodiments, $R_3$ is not

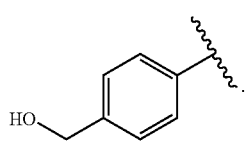

In other embodiments, $R_3$ is substituted or unsubstituted heteroaryl.

In certain embodiments, the invention provides compounds of the formula:

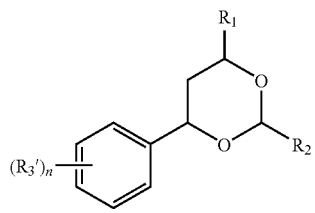

wherein $R_1$ and $R_2$ are defined as above;
n is an integer between 1 and 5, inclusive; and
each occurrence of $R_3'$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In certain embodiments, n is 0, and the phenyl ring is unsubstituted.

In other embodiments, n is 1, and the compounds are one of the formulae:

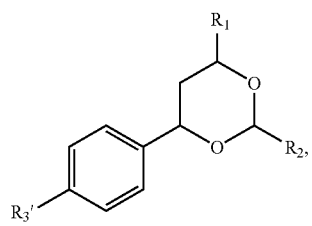

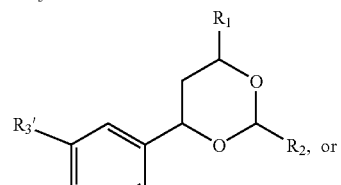

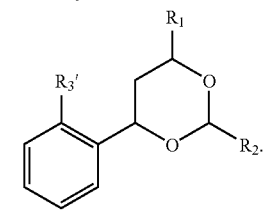

In certain embodiments, the para-substitution pattern is preferred. In other embodiments, the meta-substitution pattern is preferred. And in yet other embodiments, the ortho-substitution pattern is preferred.

In other embodiments, n is 2. Compounds of the invention include compounds of one of the formulae:

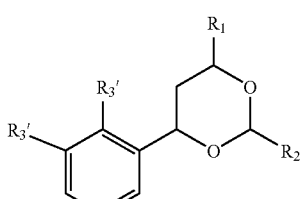

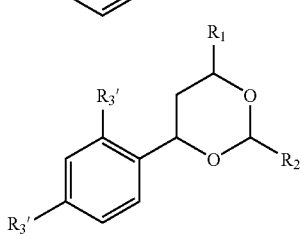

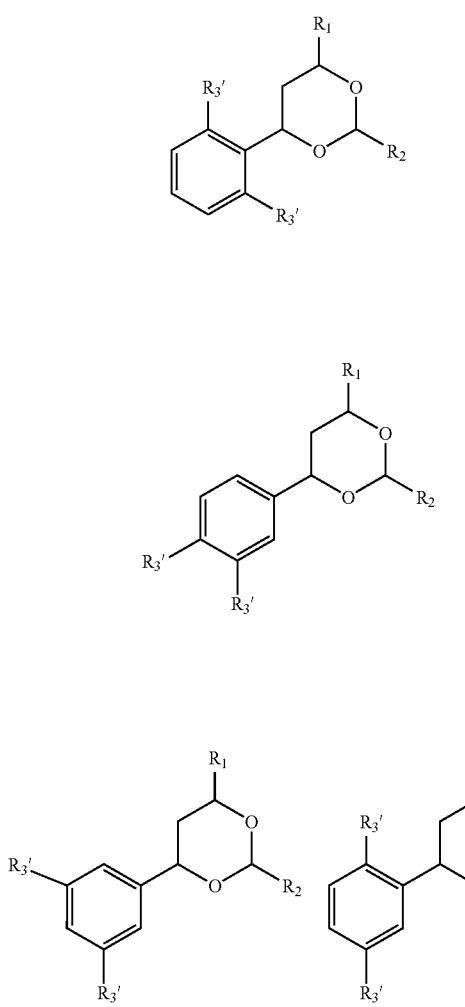

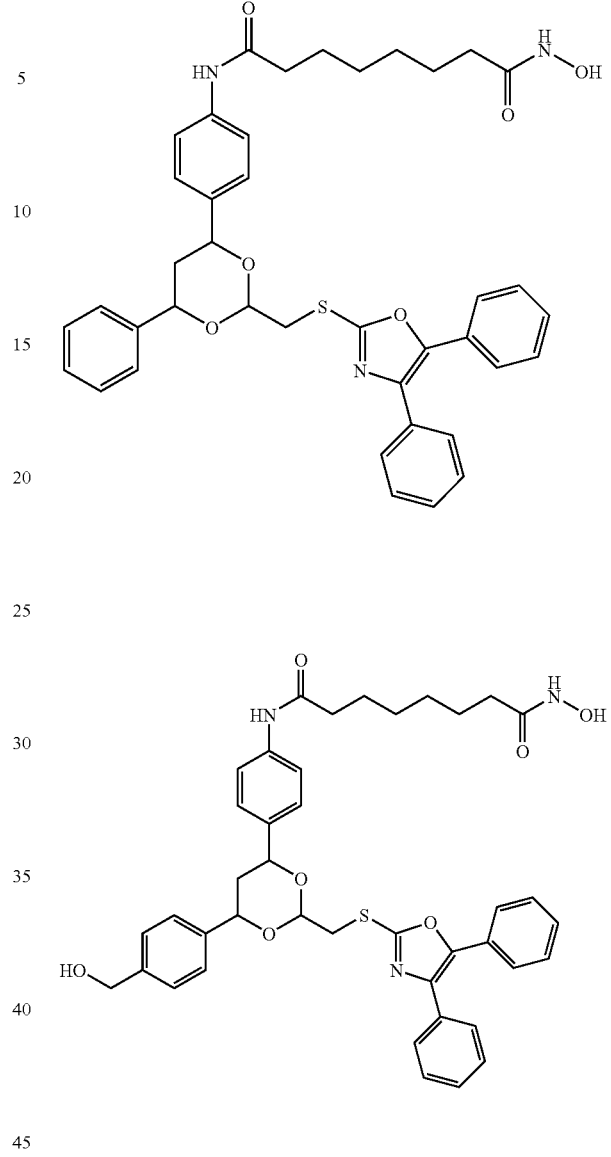

In other embodiments, n is 3. In still other embodiments, n is 4, and in other embodiments, n is 5.

In certain embodiments, $R_3'$ is halogen, hydroxyl, protected hydroxyl, alkoxy, amino, alkylamino, dialkylamino, —$NO_2$, $C_1$-$C_6$ alkyl, $C_1$-$C_6$ alkenyl, $C_1$-$C_6$ alkynyl, or acyl. In certain embodiments, $R_3'$ is —$NO_2$. In certain embodiments, $R_3'$ is —$CH_2OH$. In certain embodiments, $R_3'$ is —$NH_2$. In certain embodiments, $R_3'$ is —H. In other embodiments, $R_3'$ is —OH. In other embodiments, $R_3'$ is —CN. In yet other embodiments, $R_3'$ is —SCN. In still other embodiments, $R_3'$ is acyl. In certain embodiments, $R_3'$ is acetyl. In other embodiments, $R_3'$ is —F. In other embodiments, $R_3'$ is —Cl. In other embodiments, $R_3'$ is —Br. In other embodiments, $R_3'$ is —I. In other embodiments, $R_3'$ is methyl, ethyl, n-propyl, iso-propyl, n-butyl, tert-butyl, or iso-butyl. In certain embodiments, $R_3'$ is vinyl. In certain embodiments, $R_3'$ is halogen-substituted alkyl (e.g., trifluoromethyl). In certain embodiments, $R_3'$ is methoxy, ethyoxy, propoxy, butoxy, or pentoxy.

Exemplary compounds of the "isoisotubacin" class include compounds of the formula:

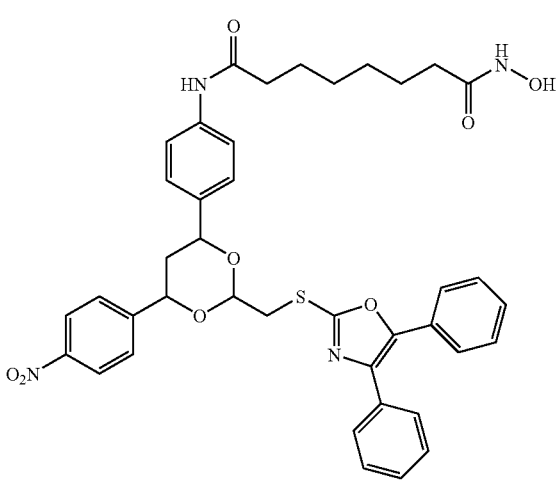

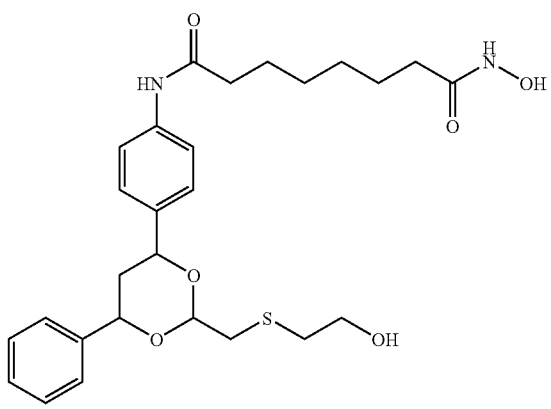

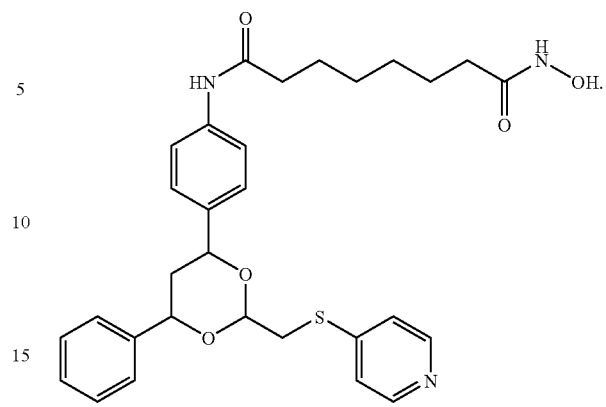

In another embodiments, the invention provides dimers, trimers, or multimers of HDAC inhibitors described herein. In certain embodiments, dimers are of the general formula,

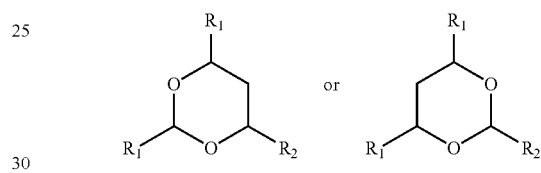

wherein each occurrence of $R_1$ comprises a functional group that inhibits histone deacetylase or tubulin deacetylase, wherein the two $R_1$ groups may be the same or different. Dimeric, trimeric, and multimeric HDAC inhibitors are further described in U.S. provisional patent application, U.S. Ser. No. 60/773,510, filed Feb. 14, 2006, which is incorporated herein by reference. The tubacin structures in the dimeric compounds therein may be changed to isotubacin and isoisotubacin structures. The dioxane core may also provide for a trimer wherein $R_2$ is —$R_1$.

In certain embodiments, $R_1$ is a substituted phenyl ring. In certain particular embodiments, $R_1$ is of the formula:

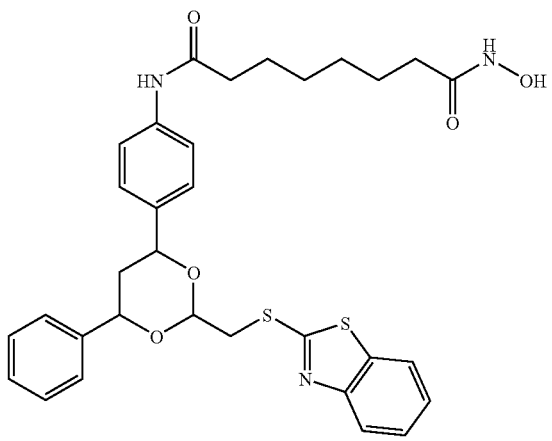

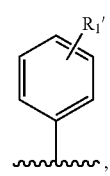

wherein $R_1'$ is

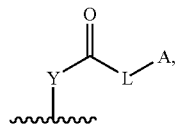

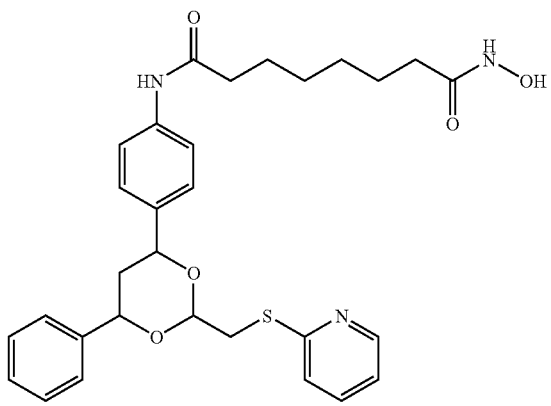

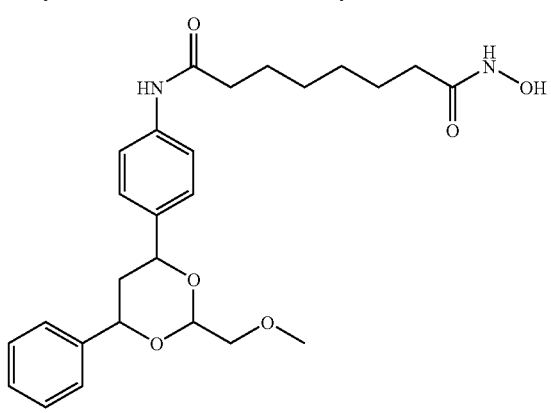

wherein Y is NH or O; L is a linker moiety; and A comprises a functional group that inhibits histone or tubulin deacetylase.

In certain embodiments, R₁ is of the formula:

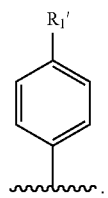

In other embodiments, R₁ is of the formula:

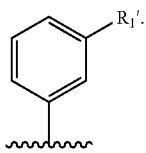

In certain embodiments, Y is NH. In other embodiments, Y is O. In certain embodiments, L is a substituted or unsubstituted, cyclic or acyclic, branched or unbranched aliphatic moiety; a substituted or unsubstituted, cyclic or acyclic, branched or unbranched heteroaliphatic moiety; a substituted or unsubstituted aryl moiety; a substituted or unsubstituted heteroaryl moiety. In certain embodiments, L is a substituted or unsubstituted, cyclic or acyclic, branched or unbranched aliphatic moiety. In certain embodiments, L is $C_1$-$C_{20}$ alkylidene, preferably $C_1$ to $C_{12}$ alkylidene, more preferably $C_4$-$C_7$ alkylidene. In certain embodiments, L is $C_1$-$C_{20}$ alkenylidene, preferably $C_1$ to $C_{12}$ alkenylidene, more preferably $C_4$-$C_7$ alkenylidene. In certain embodiments, L is $C_1$-$C_{20}$ alkynylidene, preferably $C_1$ to $C_{12}$ alkynylidene, more preferably $C_4$-$C_7$ alkynylidene. In certain embodiments, L is a substituted or unsubstituted, cyclic or acyclic, branched or unbranched heteroaliphatic moiety. In certain embodiments, L comprises a cyclic ring system, wherein the rings may be aryl, heteroaryl, non-aromatic carbocyclic, or non-aromatic heterocyclic. In still other embodiments, L comprises a substituted or unsubstituted heteroaryl moiety. In certain particular embodiments, L comprises a phenyl ring. In certain embodiments, L comprises multiple phenyl rings (e.g., one, two, three, or four phenyl rings).

In certain embodiments, L is

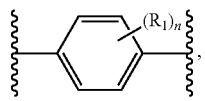

wherein n is an integer between 1 and 4, inclusive; preferably, between 1 and 3, inclusive; more preferably, 1 or 2; and R₁ is is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; —C(=O)R$_A$; —CO₂R$_A$; —CN; —SCN; —SR$_A$; —SOR$_A$; —SO₂R$_A$; —NO₂; —N(R$_A$)₂; —NHR$_A$; —NHC(O)R$_A$; or —C(R$_A$)₃; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, L is

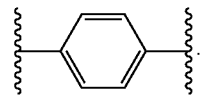

In certain embodiments, L is

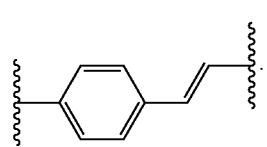

In certain embodiments, L is an unbranched, unsubstituted, acyclic alkyl chain. In certain embodiments, L is

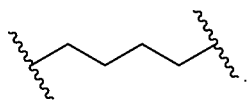

In other embodiments, L is

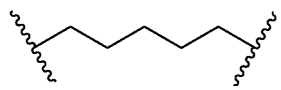

In certain other embodiments, L is

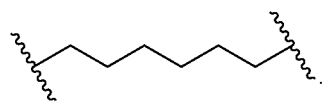

In other embodiments, L is

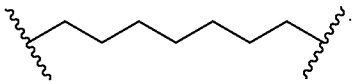

In yet other embodiments, L is

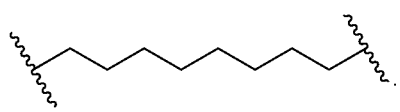

In certain embodiments, L is a substituted, acyclic aliphatic chain. In certain embodiments, L is

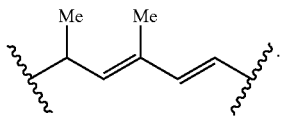

In certain embodiments, L is an unbranched, unsubstituted, acyclic heteroaliphatic chain. In certain particular embodiments, L is

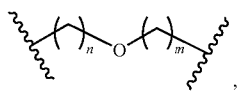

wherein n is an integer between 0 and 10, inclusive; preferably, between 0 and 5, inclusive; and m is an integer between 0 and 10, inclusive; preferably, between 0 and 5, inclusive. In certain particular embodiments, L is

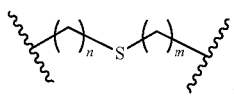

wherein n is an integer between 0 and 10, inclusive; preferably, between 0 and 5, inclusive; and m is an integer between 0 and 10, inclusive; preferably, between 0 and 5, inclusive. In certain particular embodiments, L is

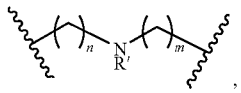

wherein n is an integer between 0 and 10, inclusive; preferably, between 0 and 5, inclusive; m is an integer between 0 and 10, inclusive; preferably, between 0 and 5, inclusive; and R' is hydrogen, $C_1$-$C_6$ aliphatic, heteroaliphatic, aryl, heteroaryl, or acyl. In certain particular embodiments, L is

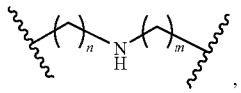

wherein n is an integer between 0 and 10, inclusive; preferably, between 0 and 5, inclusive; and m is an integer between 0 and 10, inclusive; preferably, between 0 and 5, inclusive. In certain embodiments, A comprises a metal chelating functional group. For example, A comprises a $Zn^{2+}$ chelating group. In certain embodiments, A comprises a functional group selected group consisting of:

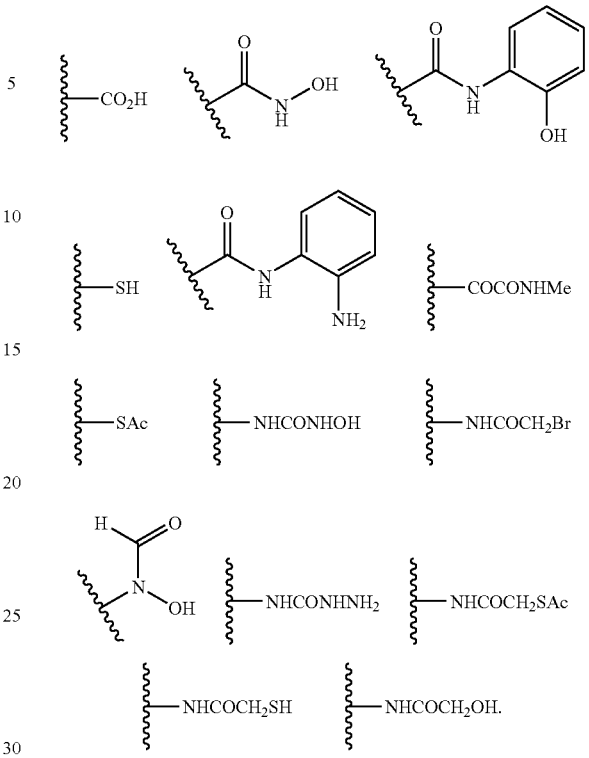

In certain embodiments, A comprises hydroxamic acid

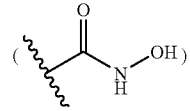

or a salt thereof. In other embodiments, A comprises the formula:

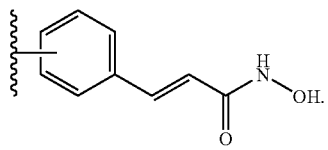

In certain particular embodiments, A comprises the formula:

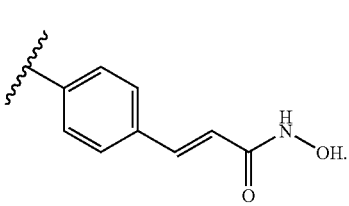

In other embodiments, A comprises a carboxylic acid (—$CO_2H$). In other embodiments, A comprises an o-aminoanilide

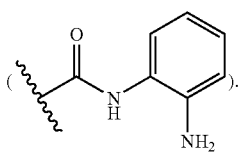

In other embodiments, A comprises an o-hydroxyanilide

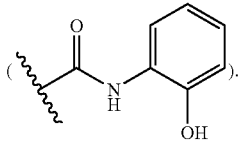

In yet other embodiments, A comprises a thiol (—SH). In certain embodiments, $R_1'$ is

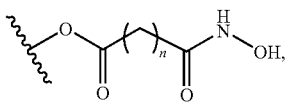

wherein n is an integer between 0 and 15, inclusive; preferably, between 0 and 10, inclusive; more preferably, between 1 and 8, inclusive; even more preferably, 4, 5, 6, 7, or 8. In certain embodiments, $R_1'$ is

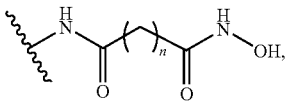

wherein n is an integer between 0 and 15, inclusive; preferably, between 0 and 10, inclusive; more preferably, between 1 and 8, inclusive; even more preferably, 4, 5, 6, 7, or 8. In certain embodiments, $R_1'$ is

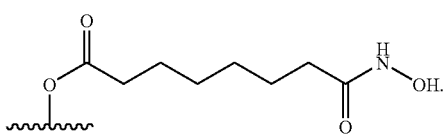

In other particular embodiments, $R_1'$ is

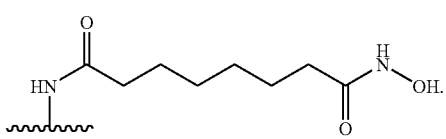

In certain embodiments of the invention, inventive compounds based on the structure of isotubacin are of the formula:

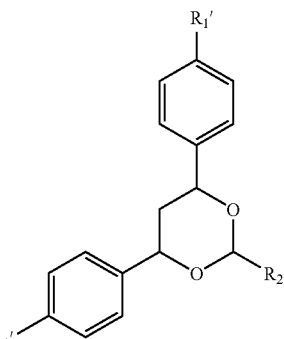

wherein each occurrence of $R_1'$ is defined as above and both occurrences of $R_1'$ are the same or different; and $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —$C(=O)R_B$; —$CO_2R_B$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_2$ is hydrogen. In other embodiments, $R_2$ is hydroxyl or a protected hydroxyl group. In certain embodiments, $R_2$ is alkoxy. In yet other embodiments, $R_2$ is a lower alkyl, alkenyl, or alkynyl group. In certain embodiments, $R_2$ is —$CH_2$—X$(R_B)_n$, wherein X is O, S, N, or C, preferably O, S, or N; and n is 1, 2, or 3. In certain embodiments, $R_2$ is —$CH_2$—$OR_B$. In other embodiments, $R_2$ is —$CH_2$—$SR_B$. In yet other embodiments, $R_2$ is —$CH_2$—$R_B$. In other embodiments, $R_2$ is —$CH_2$—$N(R_B)_2$. In still other embodiments, $R_2$ is —$CH_2$—$NHR_B$. In certain embodiments of the invention, $R_B$ is one of:

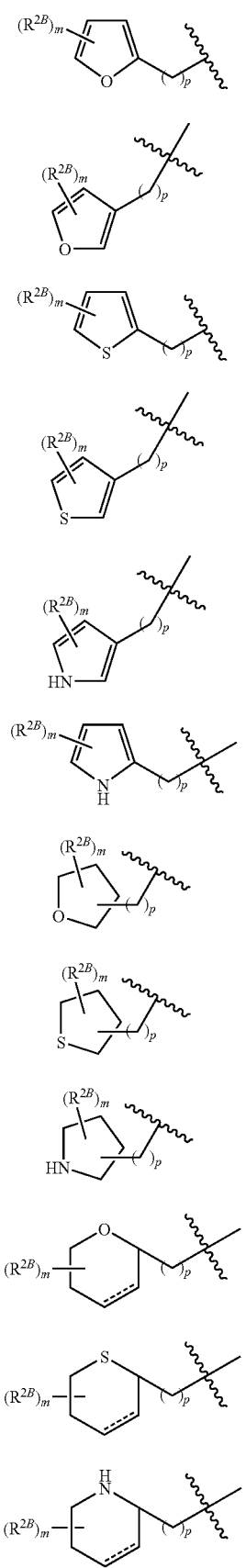
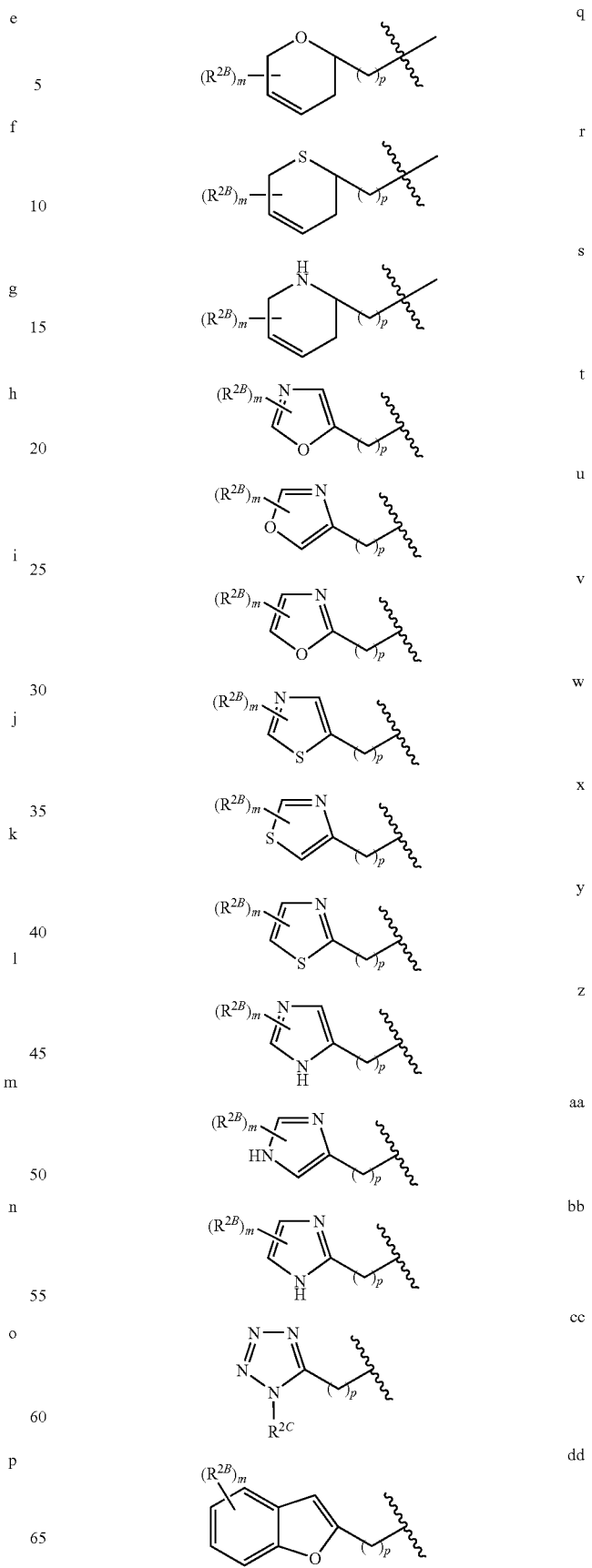

ee 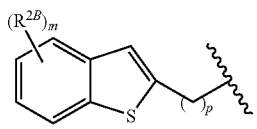

ff 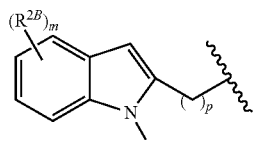
R = H, Alkyl gg 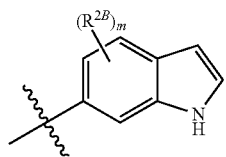

hh 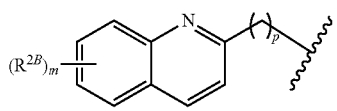

ii 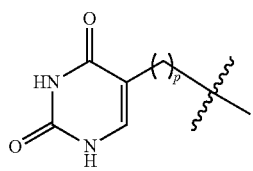

jj 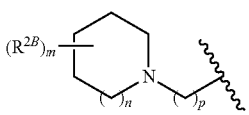
n = 0 or 1 kk 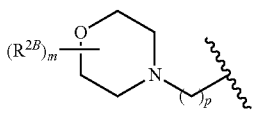

ll 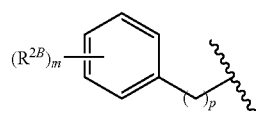

mm 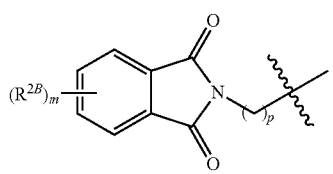

nn 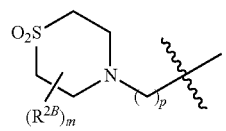

oo 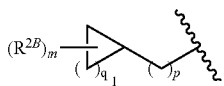

wherein m and p are each independently integers from 0 to 3; $q_1$ is an integer from 1 to 6; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —SO$_2$, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which hey are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety. In certain embodiments of the invention, $R_B$ is one of the structures:

pp 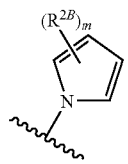

qq 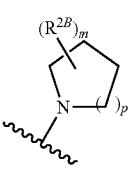

rr 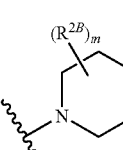

ss 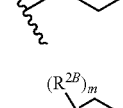

tt 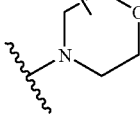

uu 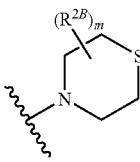

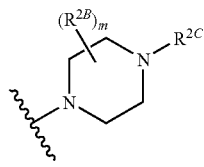

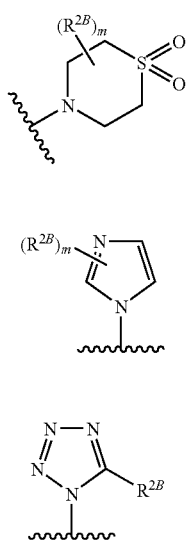

wherein m is an integer from 1 to 4; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —$SO_2$, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety.

In certain embodiments, —X($R_B$)$_n$ of —$CH_2$—X($R_B$)$_n$ has one of the structures:

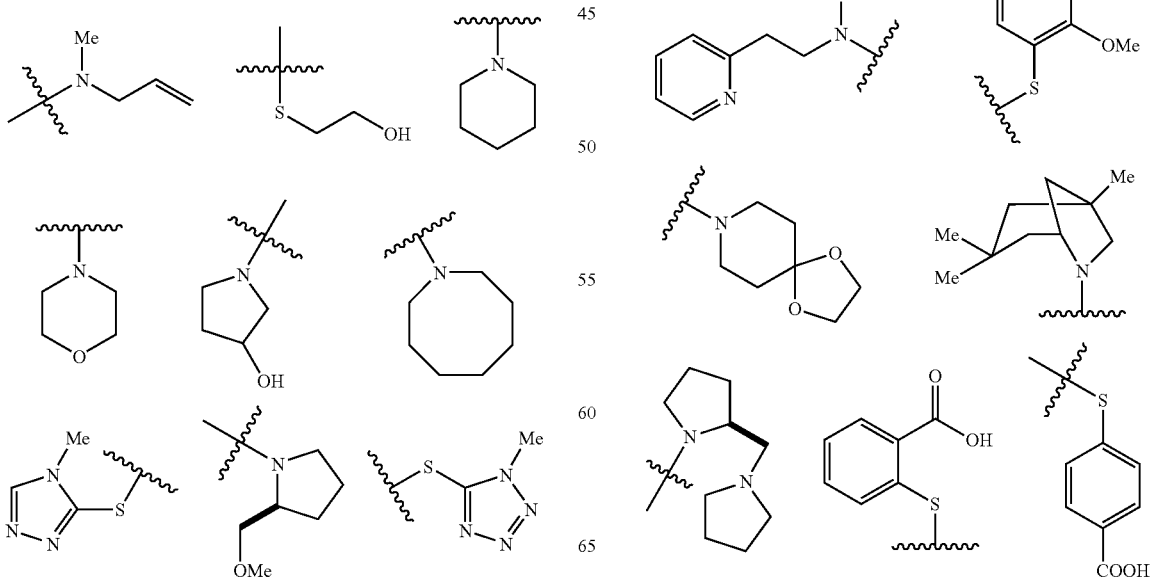

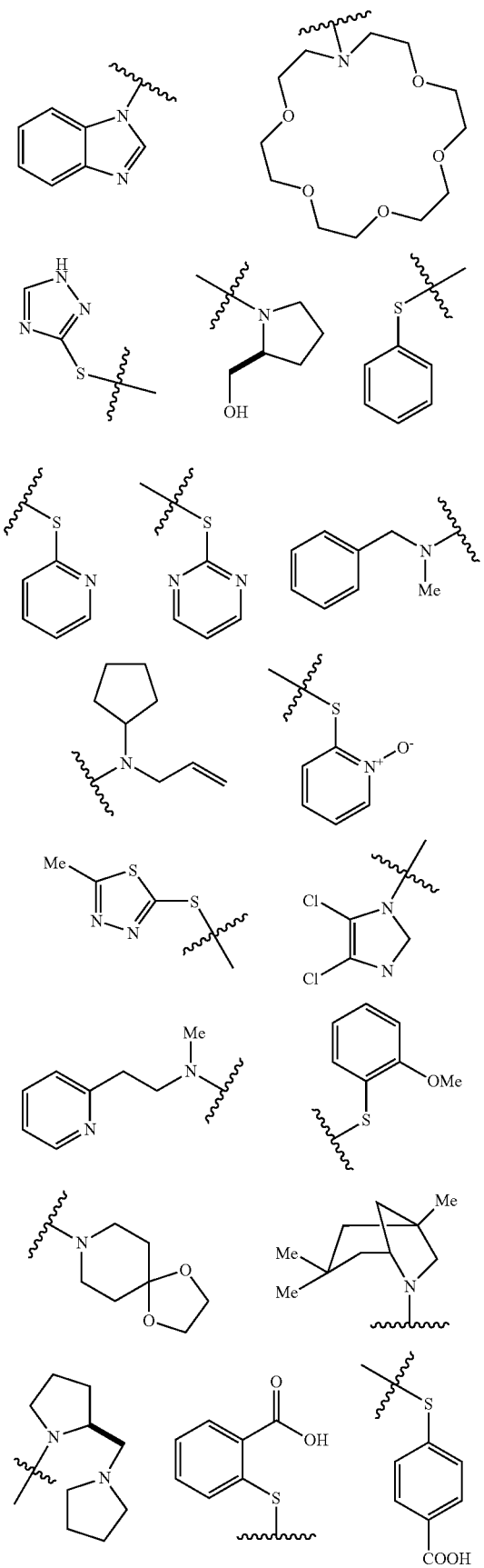

-continued
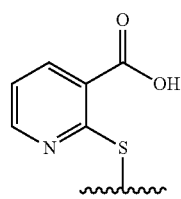
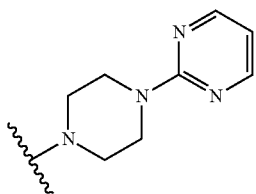
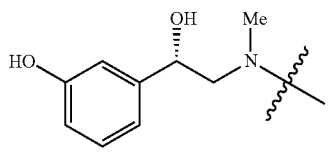
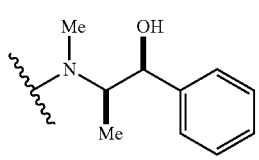
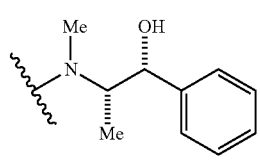
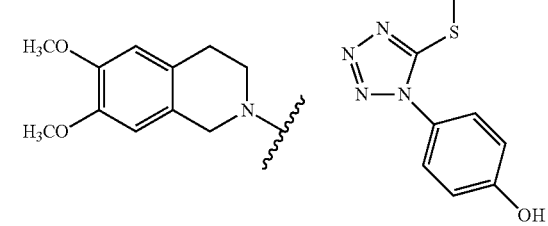
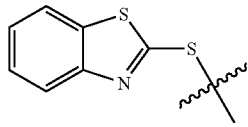
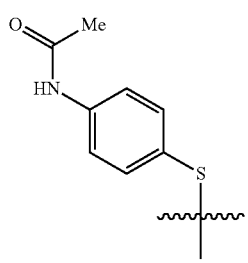
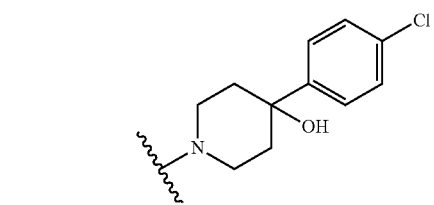
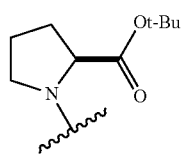
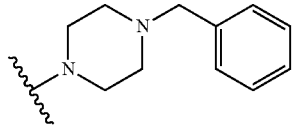
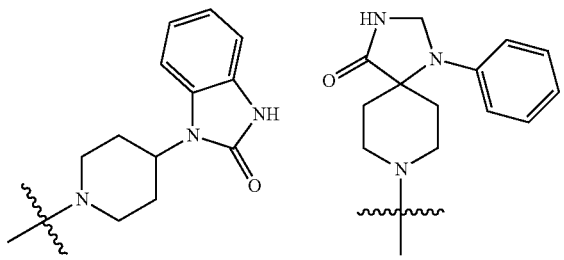
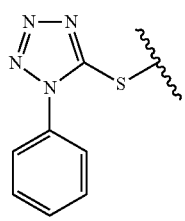
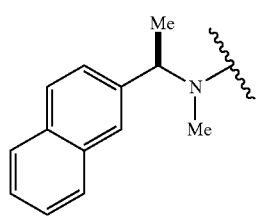
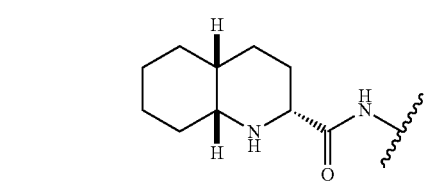
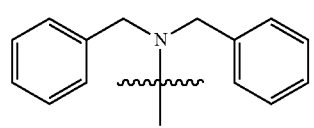
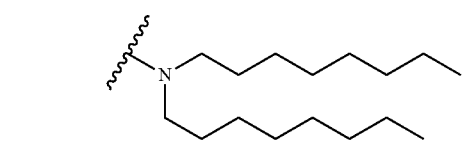

-continued
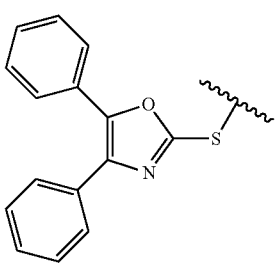
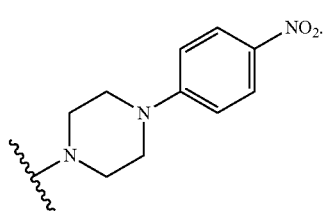
In certain embodiments, R$_2$ is
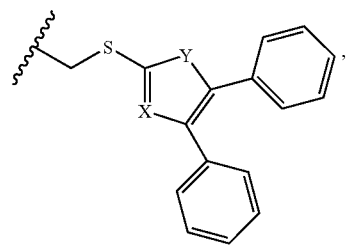
wherein X is N and Y is NH, S, or O. In other embodiments, R$_2$ is
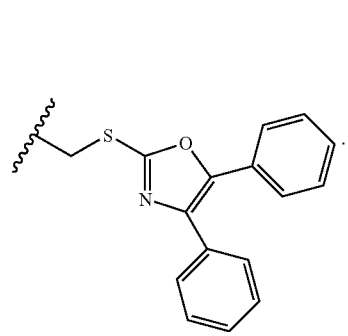
In certain embodiments of the invention, the stereochemistry of formula is chosen from one of the following:
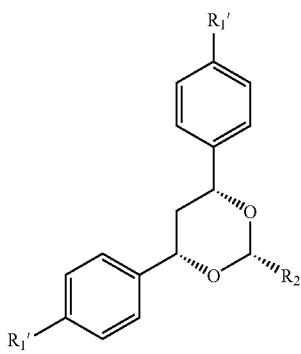
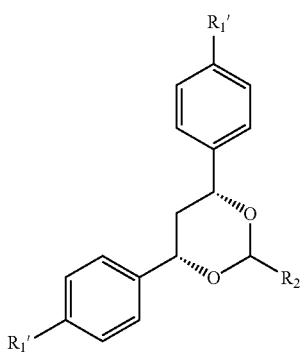
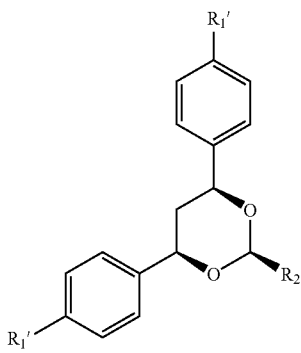
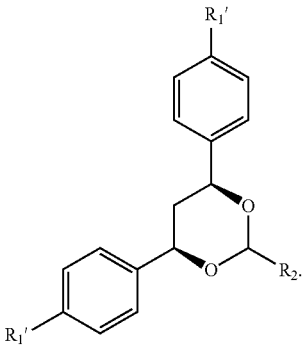

In certain embodiments of the invention, compounds are of the formula:

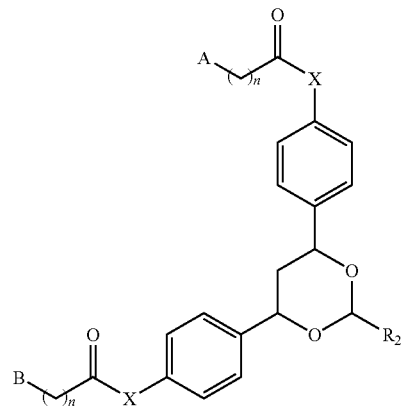

wherein

A, B, and $R_2$ are defined as above;

X is O or NH;

n is an integer between 1 and 20, inclusive; preferably, between 1 and 12, inclusive; more preferably between 2 and 8, inclusive. In certain embodiments, n is 2, 3, 4, 5, 6, 7, or 8; preferably, 6. In certain embodiments, X is NH. In other embodiments, X is O.

In certain embodiments of the invention, compounds are of the formula:

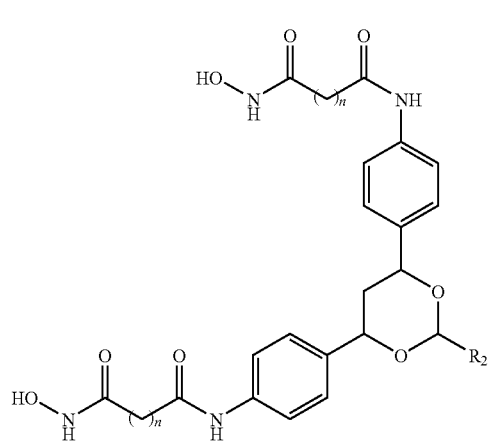

wherein $R_2$ is defined as above;

n is an integer between 1 and 20, inclusive; preferably, between 1 and 12, inclusive; more preferably between 2 and 8, inclusive. In certain embodiments, n is 2, 3, 4, 5, 6, 7, or 8; preferably, 6.

In certain embodiments of the invention, compounds are of the formula:

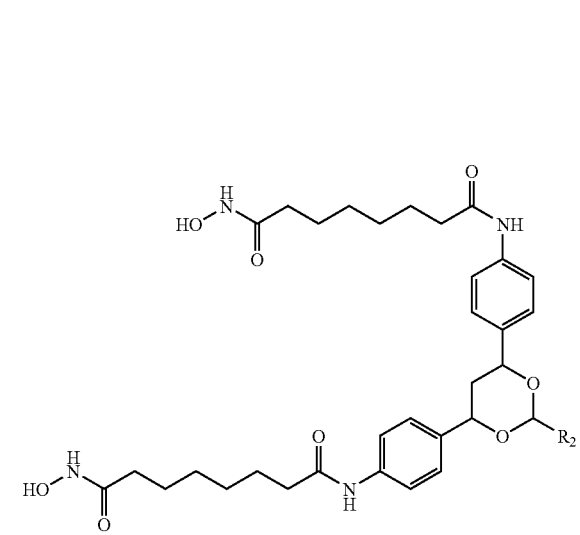

wherein $R_2$ is defined as above.

In certain embodiments of the invention, compounds are of the formula:

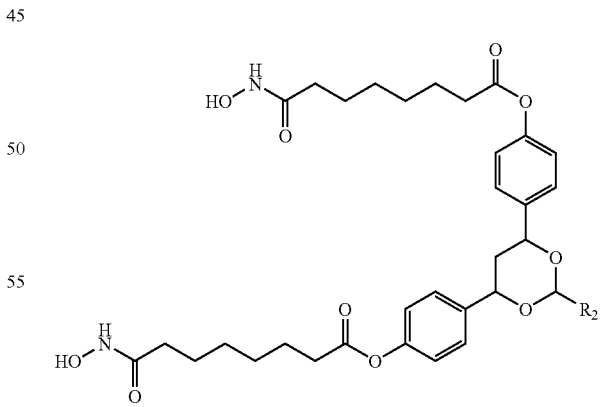

wherein $R_2$ is defined as above.

In certain embodiments of the invention, compounds are of the formula:

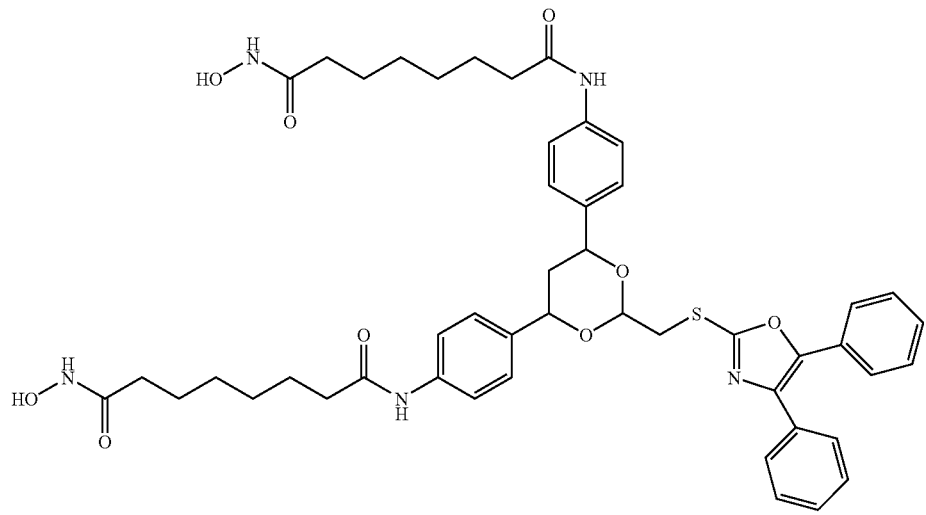

In certain embodiments of the invention, inventive compounds based on the structure of isoisotubacin are of the formula:

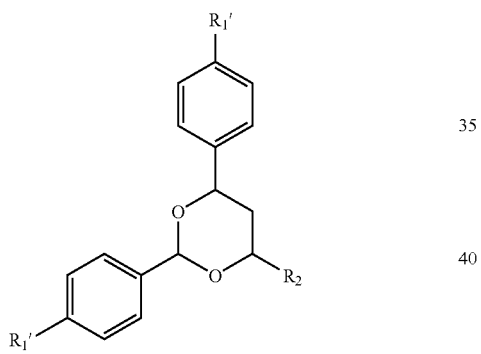

wherein
each occurrence of $R_1'$ is independently as defined above and both occurrences of $R_1'$ are the same or different; and
$R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —C(=O)$R_B$; —$CO_2R_B$; —CN; —SCN; —$SR_B$; —$SOR_B$; —$SO_2R_B$; —$NO_2$; —N($R_B$)$_2$; —NHC(O)$R_B$; or —C($R_B$)$_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_2$ is hydrogen. In other embodiments, $R_2$ is hydroxyl or a protected hydroxyl group. In certain embodiments, $R_2$ is alkoxy. In yet other embodiments, $R_2$ is a lower alkyl, alkenyl, or alkynyl group. In certain embodiments, $R_2$ is —$CH_2$—X($R_B$)$_n$, wherein X is O, S, N, or C, preferably O, S, or N; and n is 1, 2, or 3. In certain embodiments, $R_2$ is —$CH_2$—$OR_B$. In other embodiments, $R_2$ is —$CH_2$—$SR_B$. In yet other embodiments, $R_2$ is —$CH_2$—$R_B$. In other embodiments, $R_2$ is —$CH_2$—N($R_B$)$_2$. In still other embodiments, $R_2$ is —$CH_2$—$NHR_B$. In certain embodiments of the invention, $R_B$ is one of:

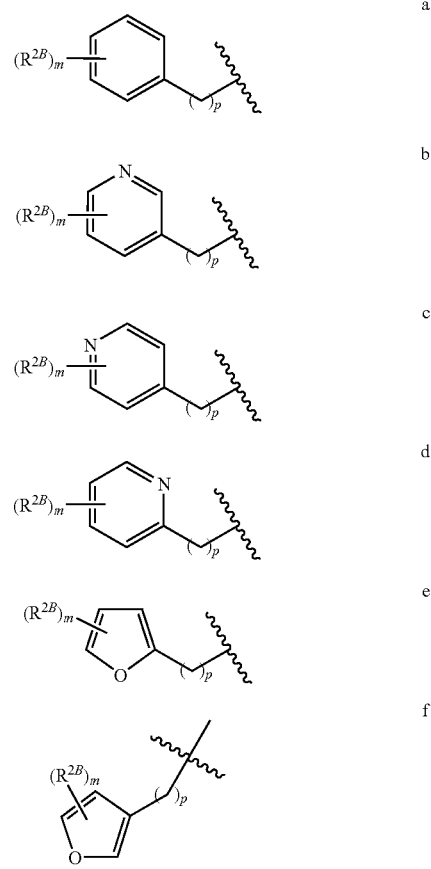

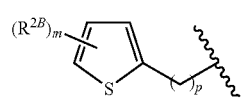 g
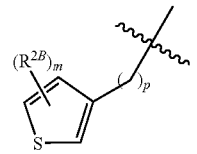 h
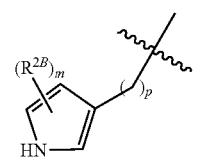 i
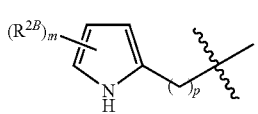 j
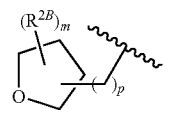 k
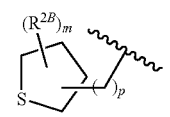 l
 m
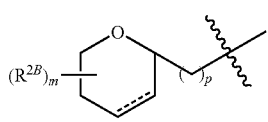 n
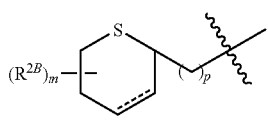 o
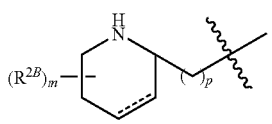 p
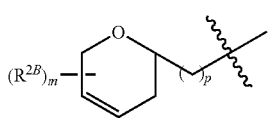 q
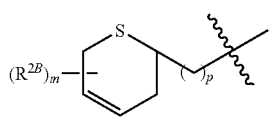 r
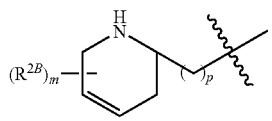 s
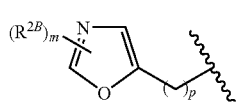 t
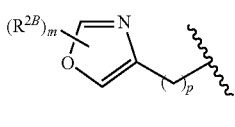 u
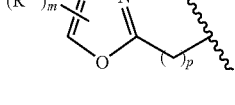 v
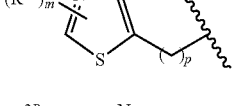 w
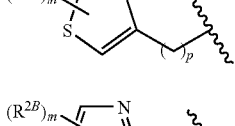 x
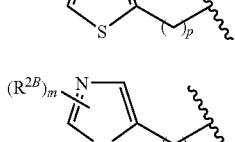 y
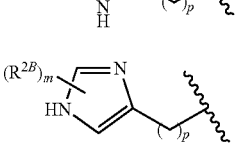 z
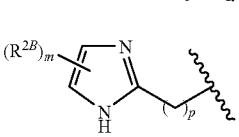 aa
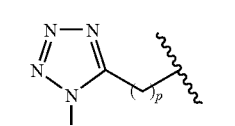 bb
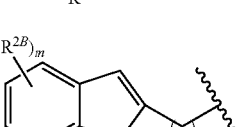 cc
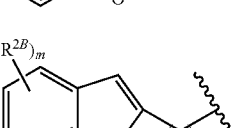 dd
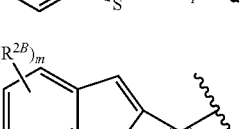 ee
ff
R = H, Alkyl -continued

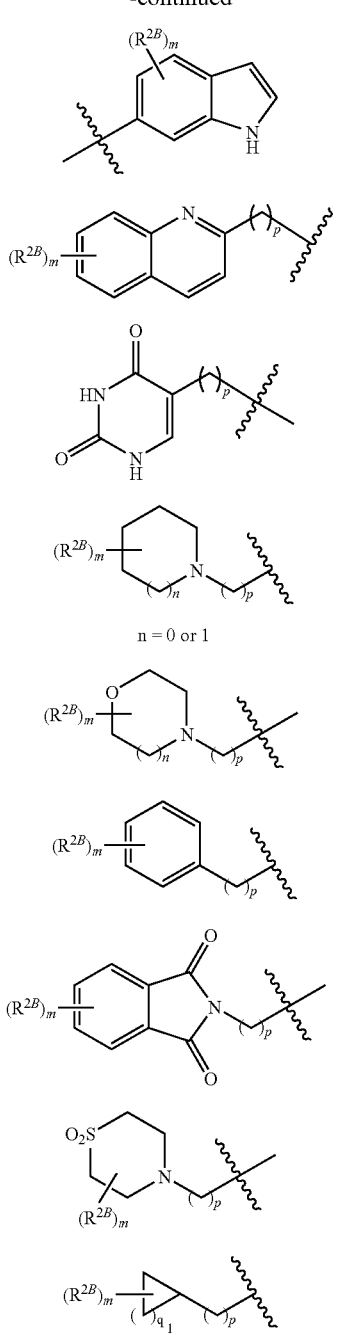

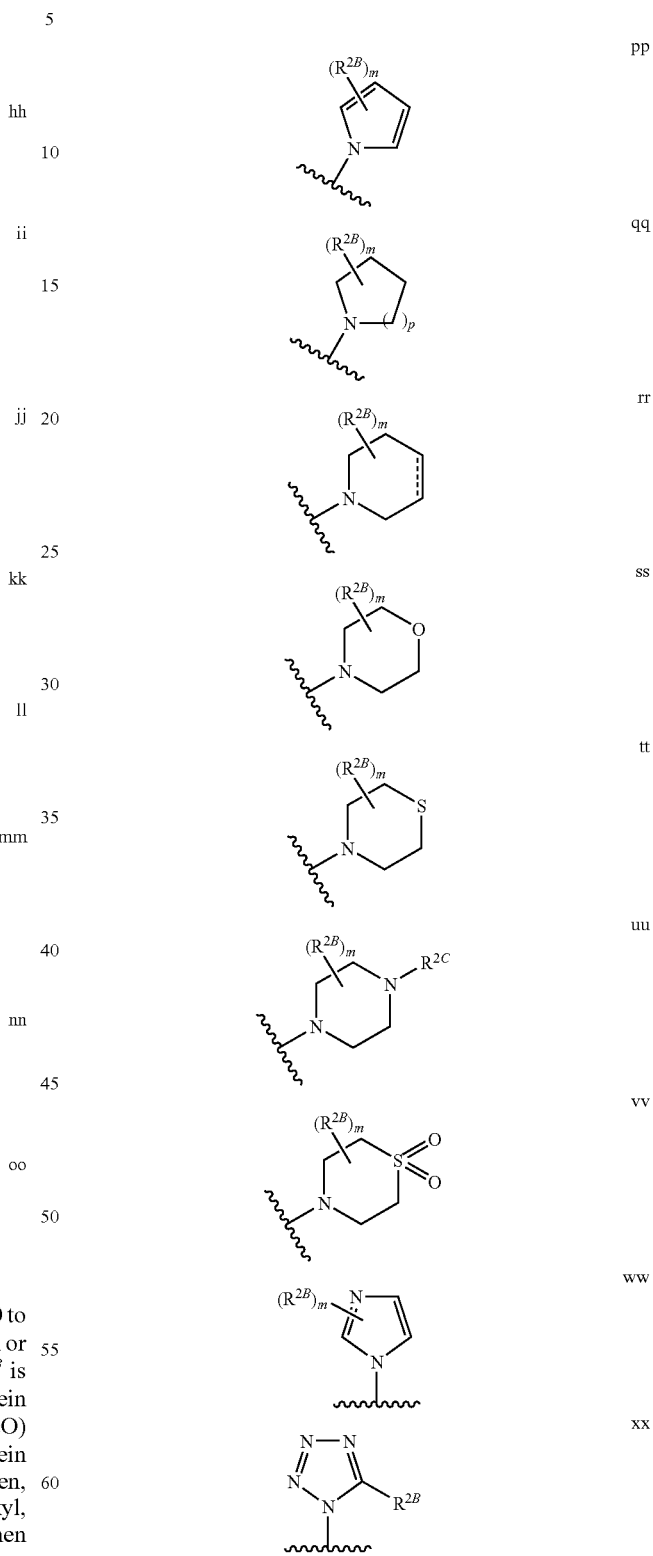

wherein m and p are each independently integers from 0 to 3; $q_1$ is an integer from 1 to 6; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —SO$_2$, —C(=O) O—, —OC(=O), —C(=O)$NR^{W2}$, $NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety. In certain embodiments of the invention, $R_B$ is one of the structures:

wherein m is an integer from 1 to 4; $R^{2C}$ is hydrogen, lower alkyl or a nitrogen protecting group; and each occurrence of $R_{2B}$ is independently hydrogen, halogen, —CN, or $WR^{W1}$ wherein W is O, S, NR$^{W2}$, —C(=O), —S(=O), —SO$_2$, —C(=O)O—, —OC(=O), —C(=O)NR$^{W2}$, NR$^{W2}$C(=O); wherein each occurrence of R$^{W1}$ and R$^{W2}$ is independently hydrogen, a protecting group, a prodrug moiety or an alkyl, cycloalkyl, heteroalkyl, heterocyclic, aryl or heteroaryl moiety, or, when W is NR$^{W2}$, R$^{W1}$ and R$^{W2}$, taken together with the nitrogen atom to which they are attached, form a heterocyclic or heteroaryl moiety; or any two adjacent occurrences of R$^{2B}$, taken together with the atoms to which they are attached, form a substituted or unsubstituted, saturated or unsaturated alicyclic or heterocyclic moiety, or a substituted or unsubstituted aryl or heteroaryl moiety.

In certain embodiments, —X(R$_B$)$_n$ of —CH$_2$—X(R$_B$)$_n$ has one of the structures:

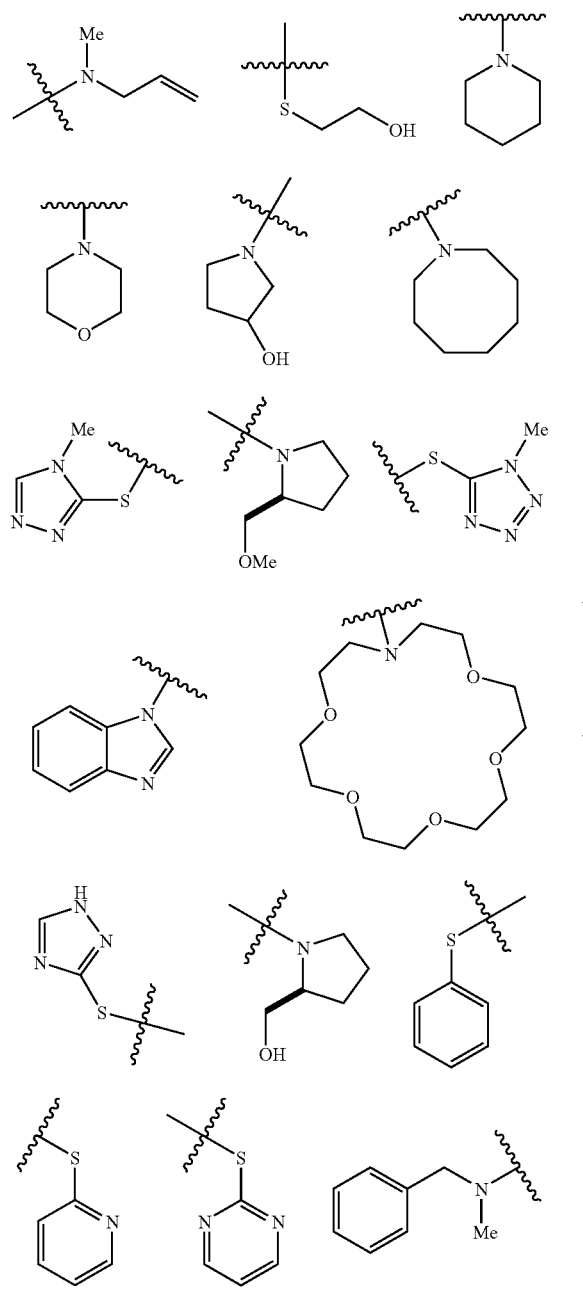

-continued

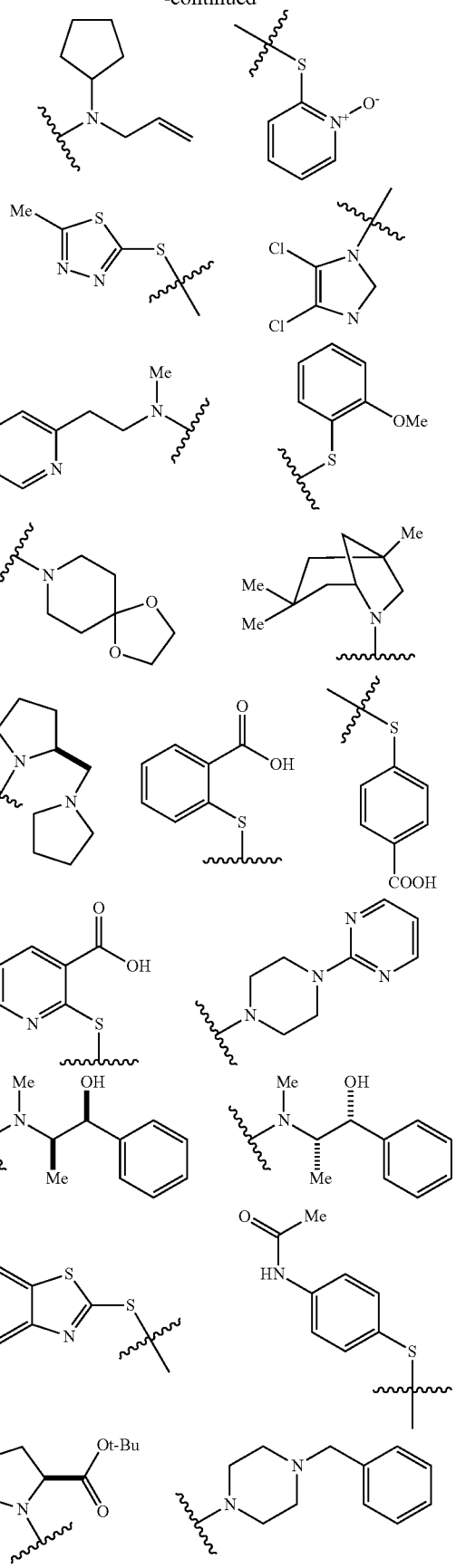

85
-continued
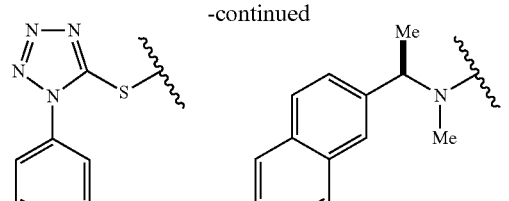
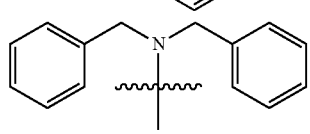
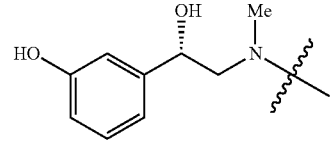
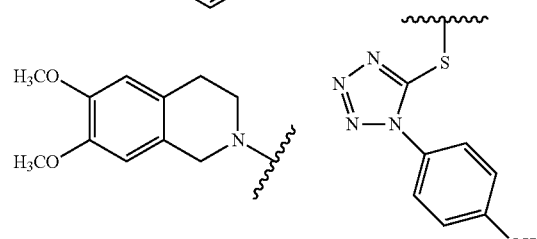
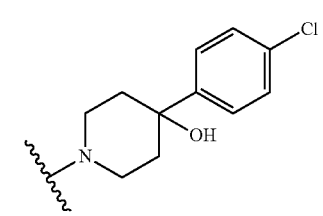
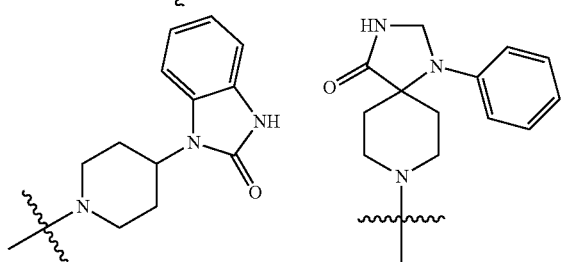
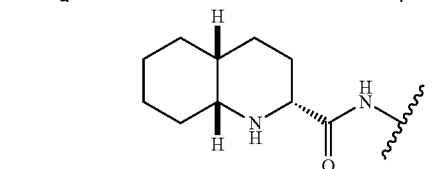
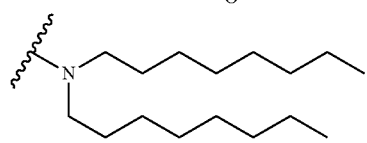
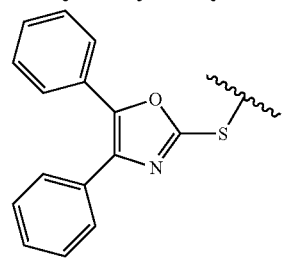
86
-continued
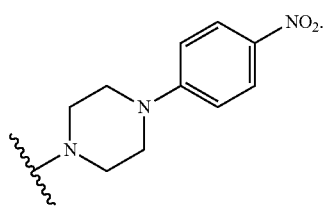
In certain embodiments, R₂ is
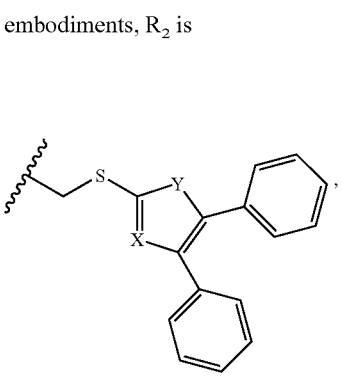
wherein X is N and Y is NH, S, or O. In other embodiments, R₂ is
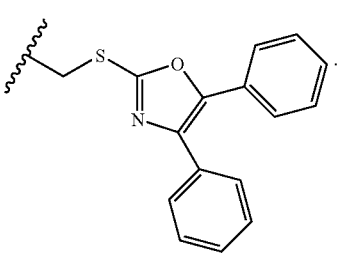
In certain embodiments of the invention, the stereochemistry of formula is chosen from one of the following:
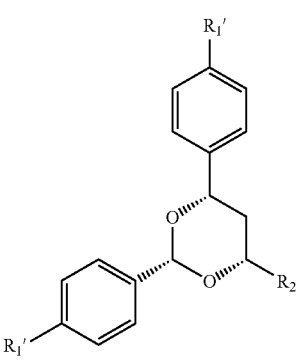

-continued

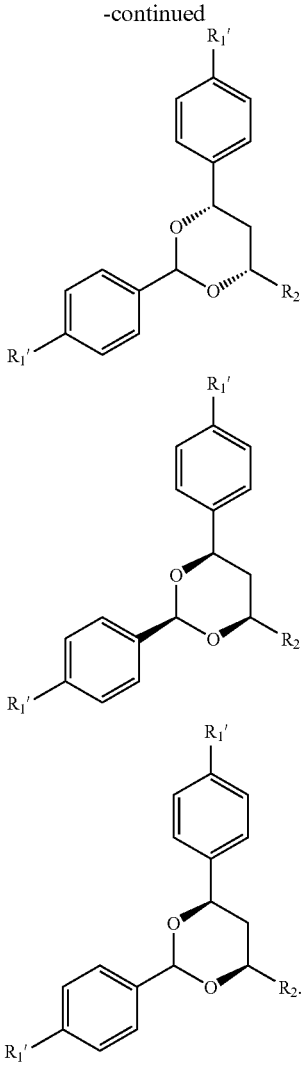

In certain embodiments of the invention, compounds are of the formula:

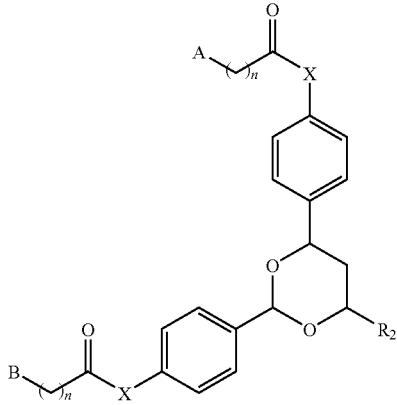

wherein
A, B, and $R_2$ are defined as above;
X is O or NH;

n is an integer between 1 and 20, inclusive; preferably, between 1 and 12, inclusive; more preferably between 2 and 8, inclusive. In certain embodiments, n is 2, 3, 4, 5, 6, 7, or 8; preferably, 6. In certain embodiments, X is NH. In other embodiments, X is O.

In certain embodiments of the invention, compounds are of the frmula:

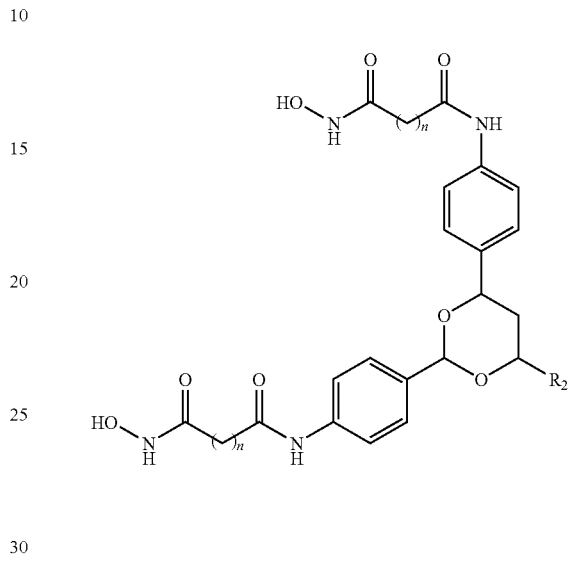

wherein
$R_2$ is defined as above;
n is an integer between 1 and 20, inclusive; preferably, between 1 and 12, inclusive; more preferably between 2 and 8, inclusive. In certain embodiments, n is 2, 3, 4, 5, 6, 7, or 8; preferably, 6.

In certain embodiments of the invention, compounds are of the formula:

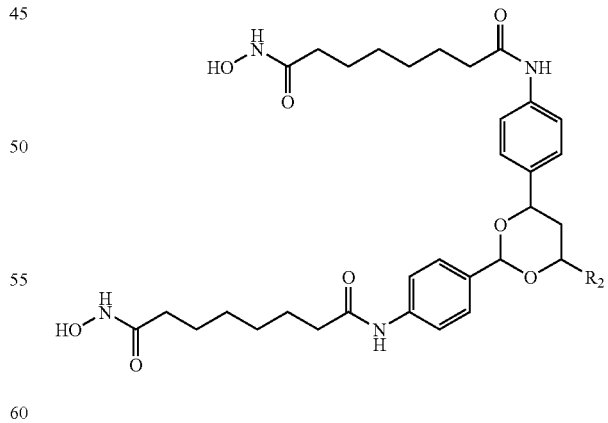

wherein
$R_2$ is defined as above.

In certain embodiments of the invention, compounds are of the formula:

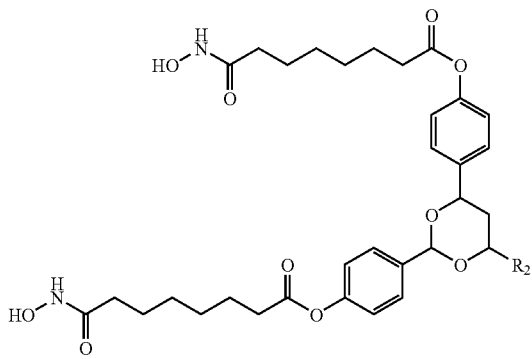

wherein

R$_2$ is defined as above.

In certain embodiments of the invention, compounds are of the formula:

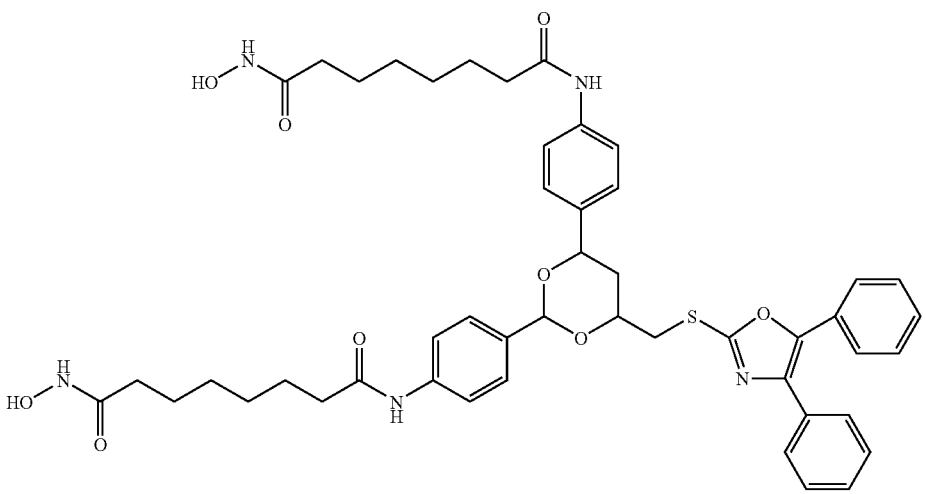

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of any of the formula above under different conditions and may exist as one or a combination of polymorphs of compound of any general formula above forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

Synthetic Overview

As described above, the present invention provides novel compounds, specifically compounds having a 1,3-dioxane core as described above. The synthesis of compounds of the "tubacin" class has been described in previously filed U.S. patent applications, U.S. Ser. No. 11/386,959, filed Mar. 22, 2006; U.S. Ser. No. 60/664,470, filed Mar. 22, 2005; U.S. Ser. No. 60/289,850, filed May 9, 2001; U.S. Ser. No. 10/144,316, filed May 9, 2002; and U.S. Ser. No. 10/621,276, filed Jul. 17, 2003; each of which is incorporated herein by reference. As would be appreciated by one of skill in this art, the various reactions and synthetic schemes described in these patent applications may be used in preparing the inventive compounds described herein.

A general synthetic scheme for preparing compounds of the isotubacin class is shown in FIG. 2. A particular exemplary synthesis of isotubacin is shown in FIG. 3. It will be appreciated that for compounds of the formula

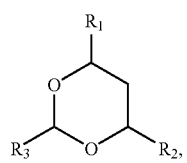

a method for the synthesis of the core structure is provided comprising steps of:

providing an epoxy alcohol having the structure:

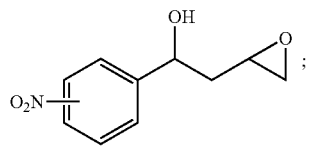

reacting the epoxy alcohol with a reagent having the structure $R_B XH$ under suitable conditions to generate a diol having the core structure:

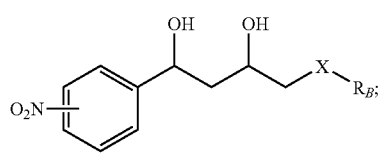

reducing the nitro group to generate a diol having the core structure:

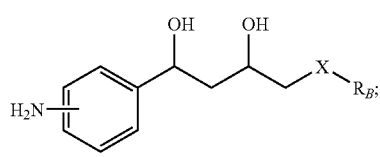

reacting the amino group with acylating agent to generate a diol having the core structure:

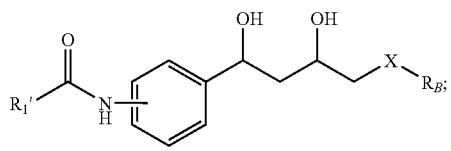

reacting the diol with a reagent having the structure $R_3CH(OMe)_2$ or other acetal under suitable conditions to generate a scaffold having the core structure:

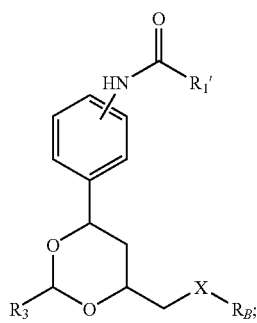

wherein $R_1'$ is -L-A, wherein L is a linker moiety; and A comprises a functional group that inhibits histone deacetylase as described herein;

$R_B$ is hydrogen, a protecting group, or an aliphatic, alicyclic, heteroaliphatic, heterocyclic, aromatic, or heteroaromatic moiety;

X is —O—, —C(R')$_2$—, —S—, or —NR'—, wherein R' is hydrogen, a protecting group, or an aliphatic, alicyclic, heteroaliphatic, heterocyclic, aromatic or heteroaromatic moiety; and $R^3$ is an aliphatic, alicyclic, heteroaliphatic, heterocyclic, aromatic, or heteroaromatic moiety. In certain embodiments rather than reacting the diol with a reagent having the structure $R_3CH(OMe)_2$ or other acetal, the diol is reacted with an aldehyde of structure $R_3CHO$. In other embodiments, the methods optionally comprises additional steps of protecting and/or deprotecting functional groups of $R_B$, $R_1$, $R_1'$, $R_2$, or $R_3$. In other embodiments, the method optionally comprises additional steps of modifying functional groups of $R_B$, $R_1$, $R_1'$, $R_2$, or $R_3$. For example, in FIG. 2 the methyl ester functionality of $R_1'$ is converted to a hydroxamic acid functional group.

In certain exemplary embodiments, the epoxy alcohol has the structure:

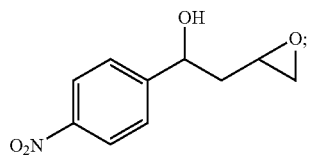

the diol has the structure:

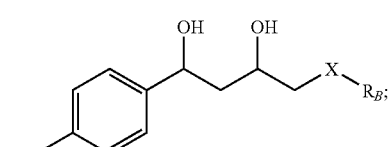

wherein X is S or O;

and the core scaffold has the structure:

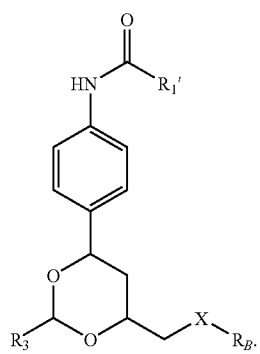

In certain other exemplary embodiments, the epoxy alcohol has the structure:

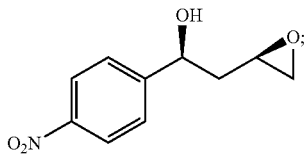

the diol has the structure:

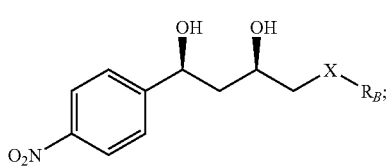

wherein X is S or O;
and the core scaffold has the structure:

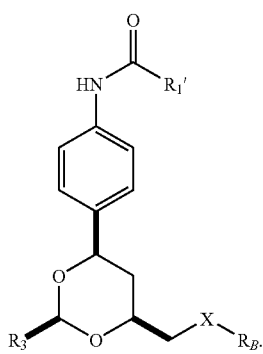

In certain other exemplary embodiments, the epoxy alcohol has the structure:

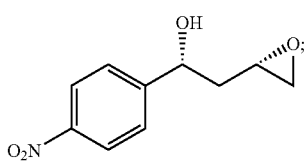

the diol has the structure:

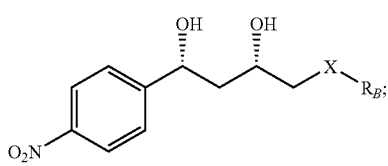

wherein X is S or O;

and the core scaffold has the structure:

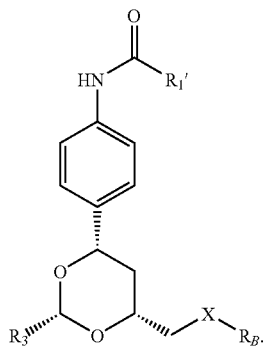

In certain exemplary embodiments, A is a hydroxamic acid. In certain embodiments, L is an $C_1$-$C_8$ alkylidene moiety. In certain embodiments, $R_3$ is a substituted or unsubstituted phenyl. In certain particular embodiments, $R_3$ is an unsubstituted phenyl. In certain embodiments, $R_3$ is a substituted phenyl. In certain embodiments, X is O. In other embodiments, X is S. In certain embodiments, X is NH or $NR_B$. In certain embodiments, $R_B$ is substituted or unsubstituted aryl or heteroaryl.

Figure 6:
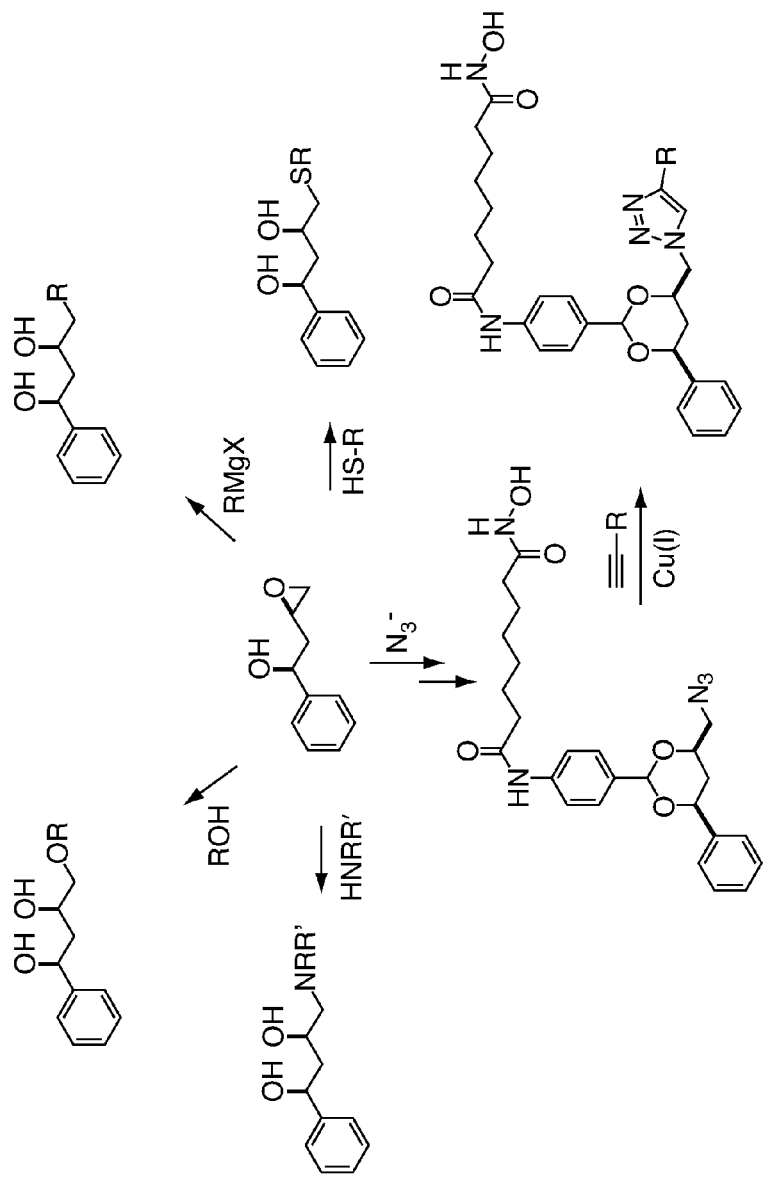
FIG. 6 shows exemplary epoxide-opening reactions useful in preparing various analogs of the inventive compounds. The scheme illustrates the use of various nucleophiles to open the epoxide group to create the diol functionality later capped to create the isotubacin and isoisotubacin structures.
Figure 7:
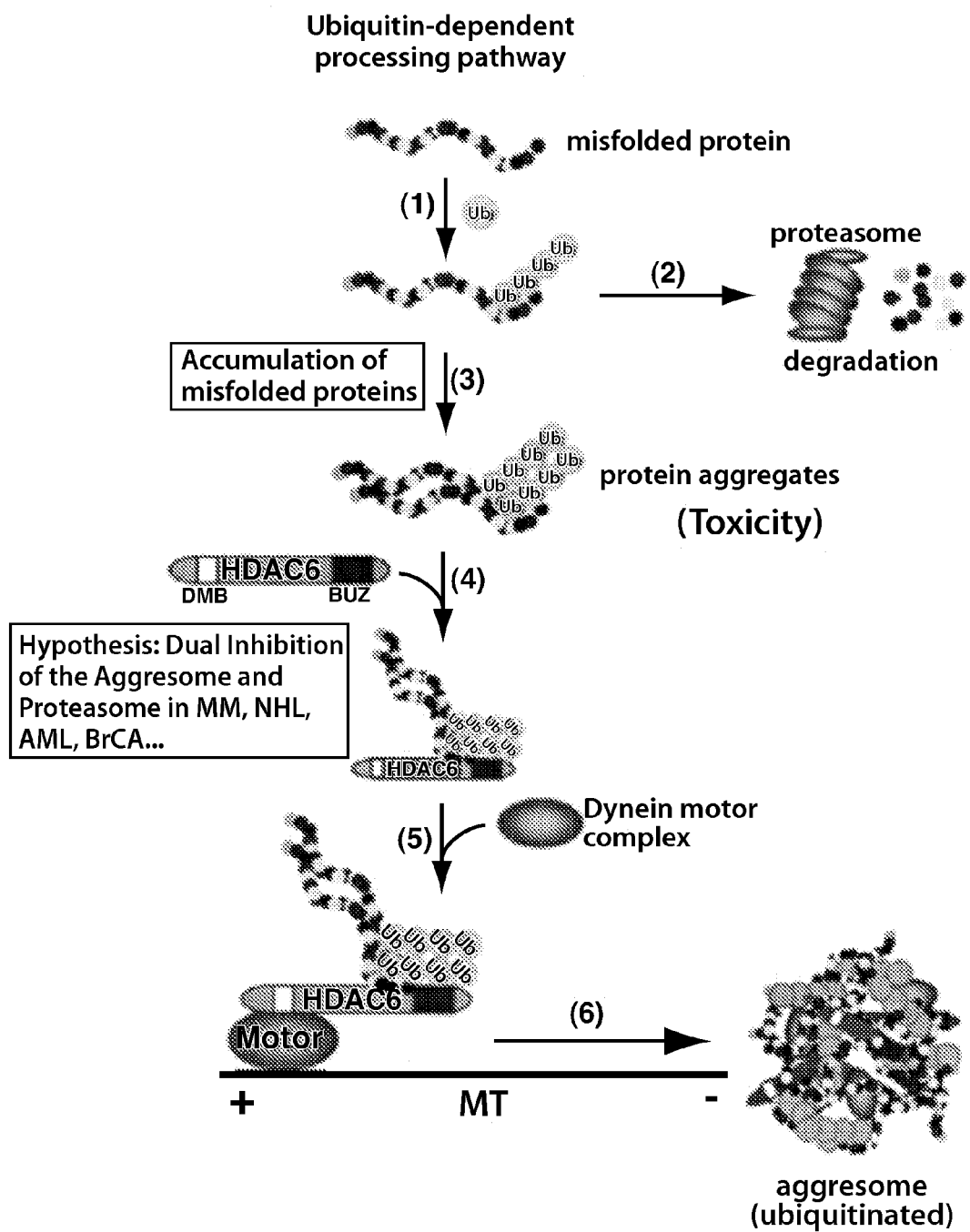
FIG. 7 graphically depicts protein degradation pathways and the scientific rationale for combining bortezomib (VELCADE®) with HDAC6 inhibitors (e.g., isotubacin, isoisotubacin) in the treatment of protein degradation disorders. There are two pathways which degrade misfolded/unfolded proteins which are ubiquitinated. The former is the proteasome pathway, and the latter is the aggresome pathway, which requires HDAC 6 activity. Therefore inhibition of both pathways by specific inhibitors, bortezomib (VELCADE®), and isotubacin or isoisotubacin, induced accumulation of cytotoxic misfolded/unfolded proteins.
Figure 8:
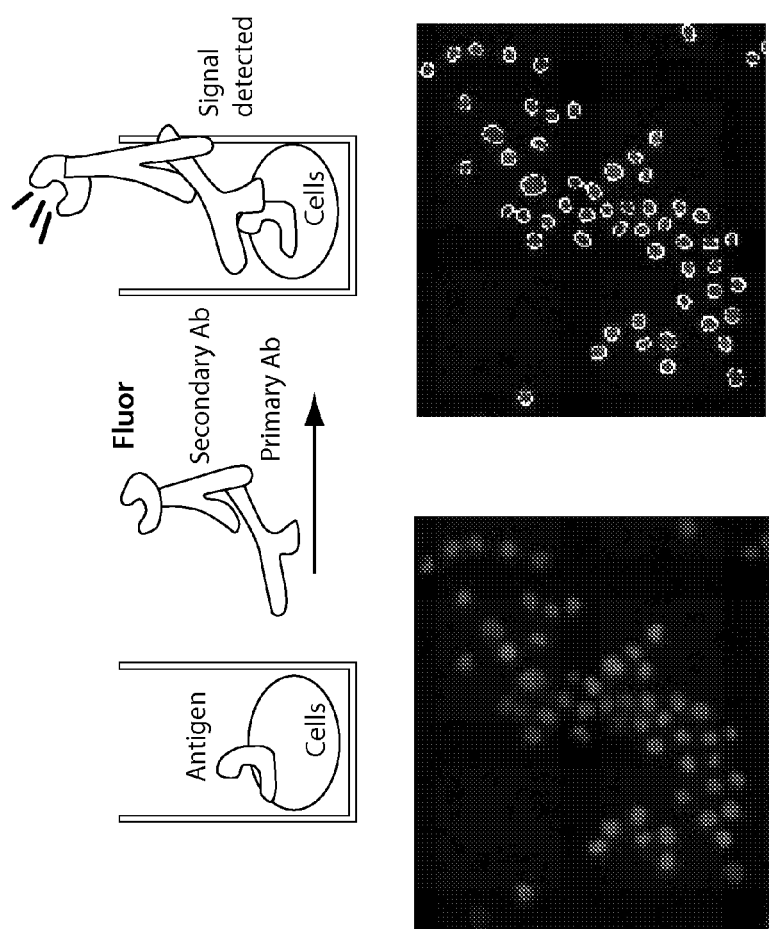
FIG. 8 is a schematic of the high-throughput immunofluorescence quantitative assay for acetylated tubulin versus acetylated lysine (as an indicator of acetylated histones) with resulting images.
Figure 9:
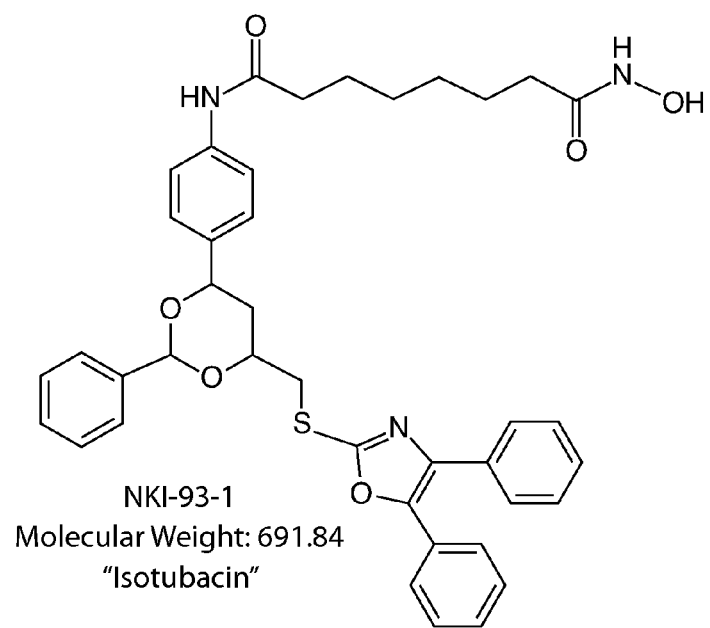
FIG. 9 shows the chemical structure for Isotubacin (NKI-93-1). The 1,3-dioxane core in tubacin derivatives is rotated 120° counter-clockwise to yield isotubacin.
Figure 10A:
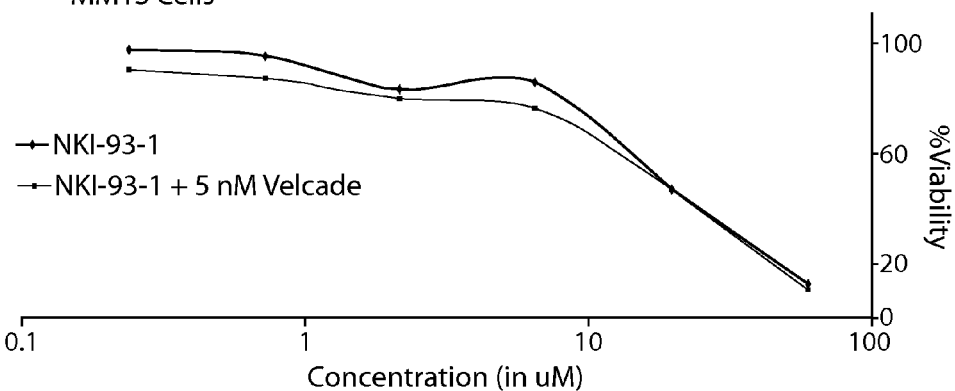
FIG. 10 shows the synergy between isotubacin (NKI-93-1) and bortezomib (VELCADE®) in myeloma cell lines (A) MM.1S, and (B) RPMI cells.
Figure 10B:
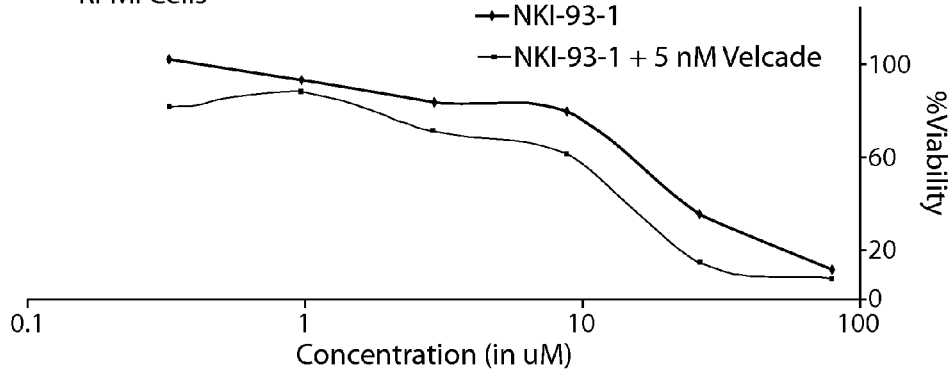
Figure 11:
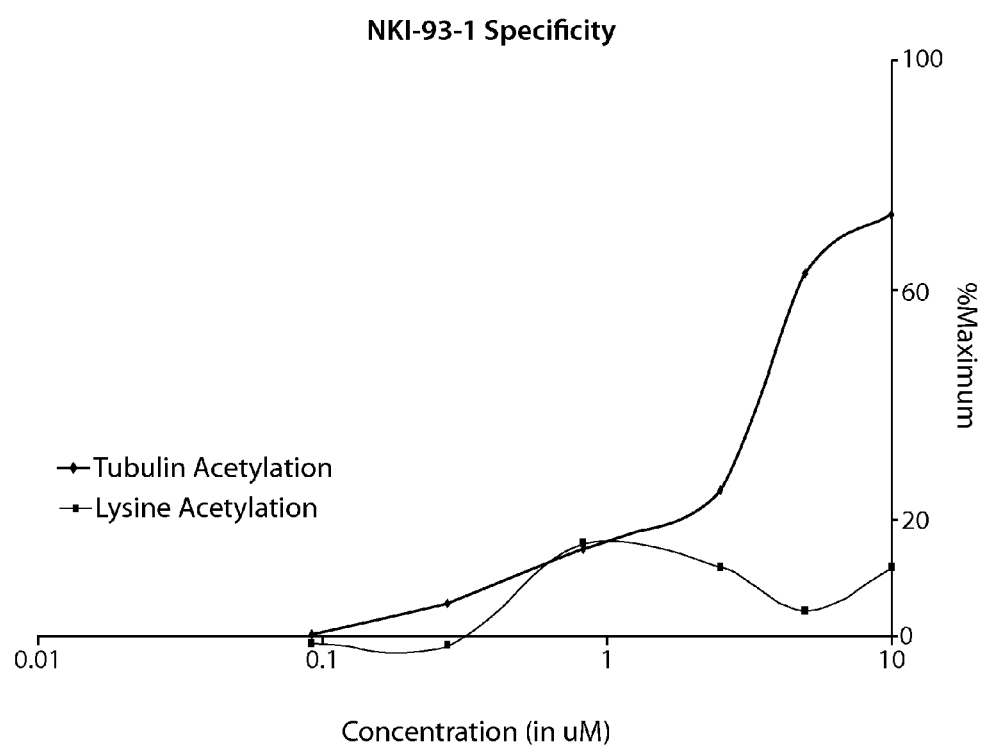
FIG. 11 demonstrates the specificity of isotubacin (NKI-93-1) for tubulin acetylation versus lysine acetylation.
Figure 12:
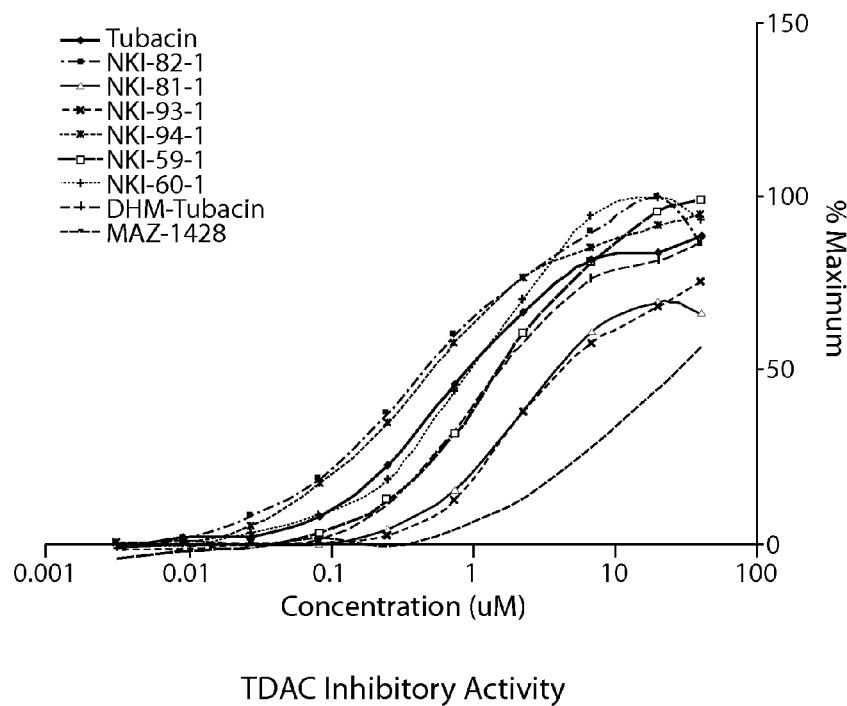
FIG. 12 shows the TDAC inhibitory activity of the compounds—tubacin, NKI-82-1, NKI-81-1, isotubacin (NKI-93-1), NKI-94-1, NKI-59-1-, NKI-60-1, DHM-Tubacin, and MAZ-1428.
Figure 13:
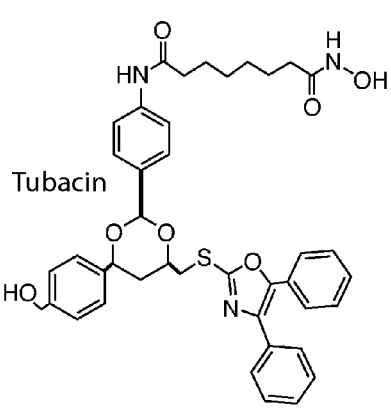
FIG. 13 is a chart showing the HDAC inhibition and TDAC inhibition of the compounds—tubacin, DHM-Tubacin, NKI-59-1, NKI-60-1, NKI-82-1, NKI-84-1, NKI-94-1 NKI-81-1, and isotubacin (NKI-93-1).
Figures 2, 14:
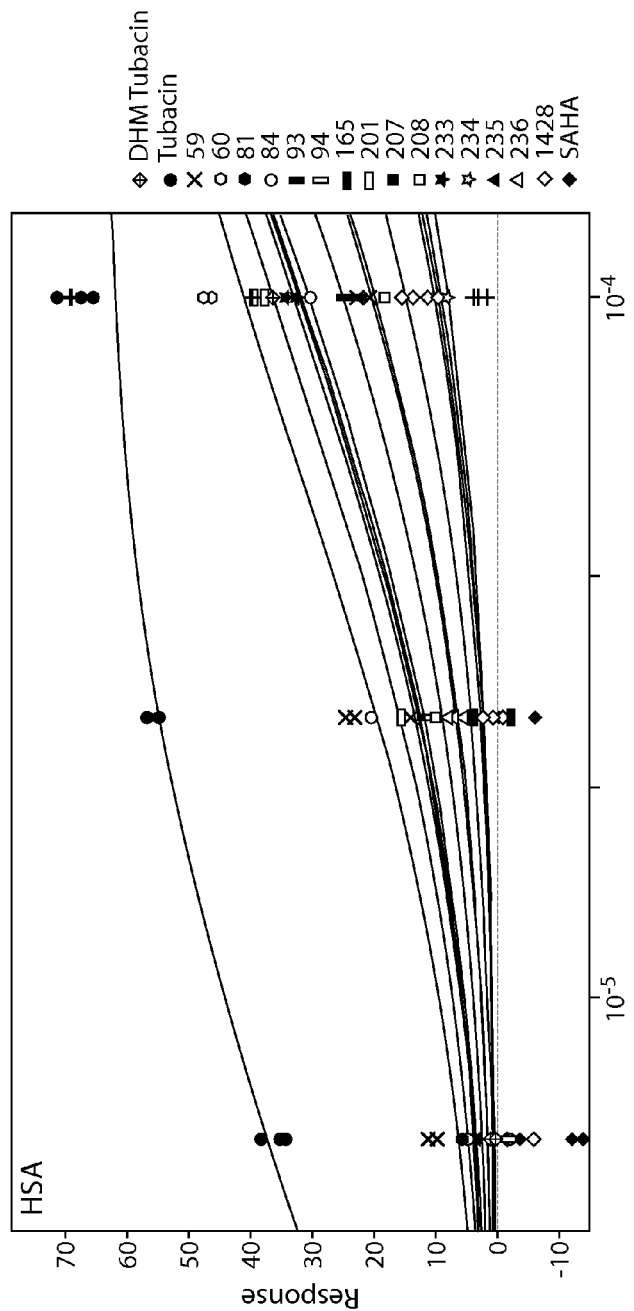
FIG. 14 shows the binding of various compounds including isotubacin (NKI-93-1) to HSA.
Figures 3, 14:
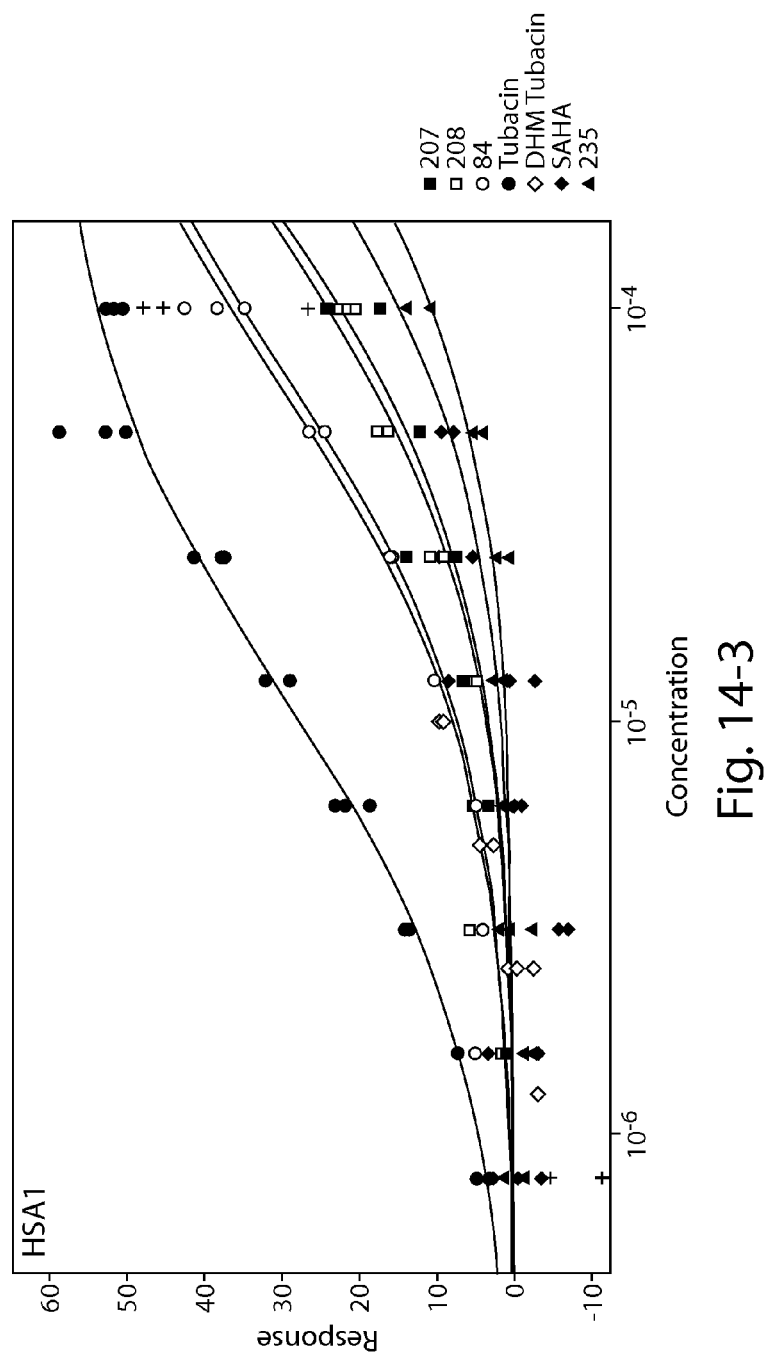

A general synthetic scheme for preparing compounds of the "isoisotubacin" class is shown in FIG. 6. A particular exemplary synthesis of isotubacin is shown in FIG. 7. It will be appreciated that for compounds of the formula

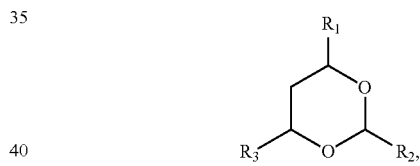

a method for the synthesis of the core structure is provided comprising steps of:

providing an beta-hydroxy ketone having the structure:

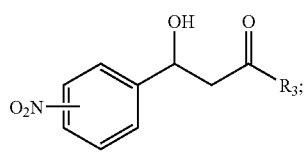

reducing the ketone to generate a diol having the core structure:

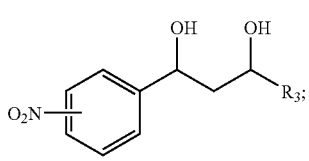

reducing the nitro group to generate a diol having the core structure:

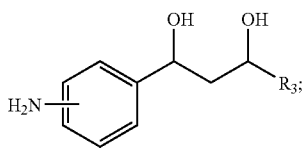

reacting the amino group with acylating agent to generate a diol having the core structure:

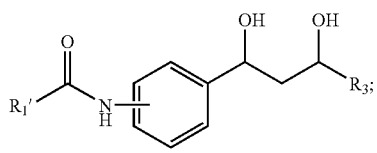

reacting the diol with a reagent having the structure R₂CH(OMe)₂ or other acetal under suitable conditions to generate a scaffold having the core structure:

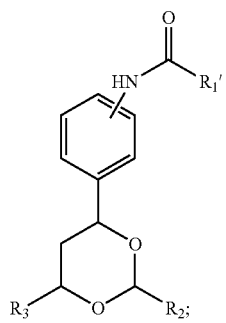

wherein R₁' is -L-A, wherein L is a linker moiety; and A comprises a functional group that inhibits histone or tubulin deacetylase as described herein;

R_B is hydrogen, a protecting group, or an aliphatic, alicyclic, heteroaliphatic, heterocyclic, aromatic, or heteroaromatic moiety;

X is —O—, —C(R')₂—, —S—, or —NR'—, wherein R' is hydrogen, a protecting group, or an aliphatic, alicyclic, heteroaliphatic, heterocyclic, aromatic or heteroaromatic moiety; and R³ is an aliphatic, alicyclic, heteroaliphatic, heterocyclic, aromatic, or heteroaromatic moiety. In certain embodiments rather than reacting the diol with a reagent having the structure R₂CH(OMe)₂ or other acetal, the diol is reacted with an aldehyde of structure R₂CHO. In certain embodiments, the reagent R₂CH(OMe)₂ or other acetal is formed from the corresponding aldehyde R₂CHO. In certain embodiments, R₂ is a substituted or unsubstituted aryl or heteroaryl moiety as described in the classes and subclasses herein. In other embodiments, the methods optionally comprises additional steps of protecting and/or deprotecting functional groups of R₁, R₁', R₂, or R₃. In other embodiments, the method optionally comprises additional steps of modifying functional groups of R₁, R₁', R₂, or R₃. For example, in FIG. 4 the protected hydroxamic acid functionality of R₁' is deprotected.

In certain embodiments, the step of providing a beta-hydroxy ketone having the structure:

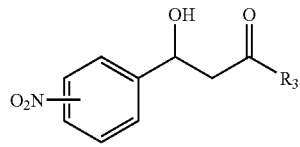

comprises reacting an aldehyde of formula:

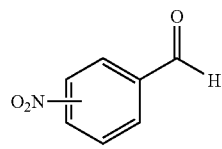

with a ketone of formula:

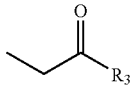

under suitable conditions (e.g., basic conditions) to form the beta-hydroxy ketone.

In certain exemplary embodiments, the epoxy alcohol has the structure:

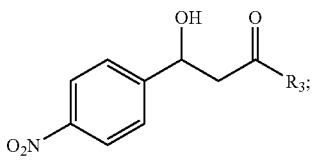

the diol has the structure:

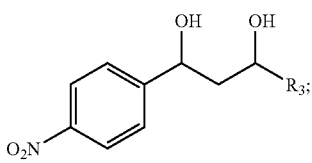

wherein X is S or O;
and the core scaffold has the structure:

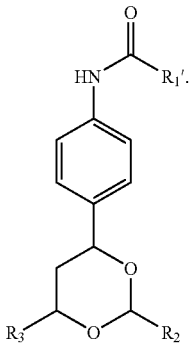

In certain other exemplary embodiments, the epoxy alcohol has the structure:

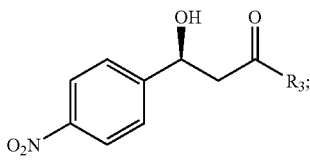

the diol has the structure:

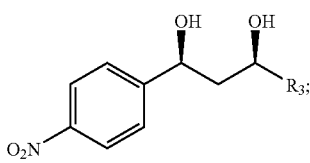

wherein X is S or O;
and the core scaffold has the structure:

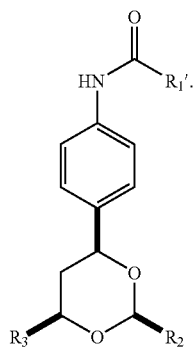

In certain other exemplary embodiments, the epoxy alcohol has the structure:

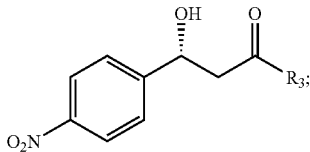

the diol has the structure:

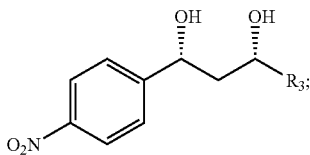

wherein X is S or O;

and the core scaffold has the structure:

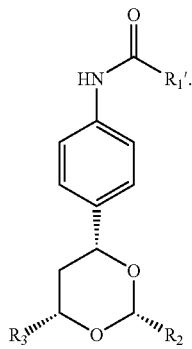

In certain exemplary embodiments, A is a hydroxamic acid. In certain embodiments, L is an $C_1$-$C_8$ alkylidene moiety. In certain embodiments, $R_3$ is a substituted or unsubstituted phenyl. In certain particular embodiments, $R_3$ is an unsubstituted phenyl. In certain embodiments, $R_3$ is a substituted phenyl. In certain embodiments, X is O. In other embodiments, X is S. In certain embodiments, X is NH or $NR_B$. In certain embodiments, $R_B$ is substituted or unsubstituted aryl or heteroaryl.

Pharmaceutical Compositions

As discussed above, the present invention provides novel compounds having antitumor, antineurodegernative, antibiotic, and antiproliferative activity, and thus the inventive compounds are useful for the treatment of cancer, benign neoplasms, neurodegenerative disorders, protein degradation disorders, and protein deposition disorders.

Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved chemotherapeutic agent, or it may be any one of a number of agents undergoing approval in the Food and Drug Administration that ultimately obtain approval for the treatment of protozoal infections and/or any disorder associated with cellular hyperproliferation. In certain other embodiments, the additional therapeutic agent is an anticancer agent, as discussed in more detail herein. In certain other embodiments, the compositions of the invention are useful for the treatment of protozoal infections. In the treatment of cancer or protein degradation disorders, the inventive compound may be combined with a proteasome inhibitor (e.g., bortezomib, R115777 FTI, MG132, NPI-0052, etc.). In the treatment of cancer or protein degradation disorders, the inventive compound may be combined with protein degradation inhibitor (e.g., another inventive compound, a tubacin-like compound, bortezomib, R115777 FTI, MG132, NPI-0052, SAHA, $^{166}$Ho-DOTMP, arsenic trioxide, 17-AAG, MG132, sapojargon, etc.).

As discussed above, the compounds of the present invention are useful as anticancer agents, and thus may be useful in the treatment of cancer, by effecting tumor cell death or inhibiting the growth of tumor cells. In general, the inventive anticancer agents are useful in the treatment of cancers, including, but not limited to breast cancer, brain cancer, skin cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells, and thus are useful for the treatment of leukemias (e.g., myeloid, lymphocytic, promyelocytic, myelocytic and lymphoblastic leukemias, whether acute or chromic forms). In still other embodiments, the inventive anticancer agents are active against solid tumors and also kill and/or inhibit the growth of multidrug resistant cells (MDR cells). In certain embodiments, the inventive anticancer agents are active against cancers which are resistant to other known anti-neoplastic agents or which have been found not to respond clinically to other known anti-neoplastic agents.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present invention encompasses pharmaceutically acceptable topical formulations of inventive compounds. The term "pharmaceutically acceptable topical formulation," as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent, anticancer agent or agent useful for the treatment of psoriasis), or they may achieve different effects (e.g., control of any adverse effects).

For example, other therapies or anticancer agents that may be used in combination with the inventive compounds of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (e.g., mechlorethamine, chlorambucil, Cyclophosphamide, Melphalan, Ifosfamide), antimetabolites (e.g., Methotrexate), purine antagonists and pyrimidine antagonists (e.g., 6-Mercaptopurine, 5-Fluorouracil, Cytarabile, Gemcitabine), spindle poisons (e.g., Vinblastine, Vincristine, Vinorelbine, Paclitaxel), podophyllotoxins (e.g., Etoposide, Irinotecan, Topotecan), antibiotics (Doxorubicin, Bleomycin, Mitomycin), nitrosoureas (e.g., Carmustine, Lomustine), inorganic ions (e.g., Cisplatin, Carboplatin), enzymes (e.g., Asparaginase), and hormones (e.g., Tamoxifen, Leuprolide, Flutamide, and Megestrol), to name a few. For a more comprehensive discussion of updated cancer therapies see, *The Merck Manual*, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe).

In certain embodiments, the pharmaceutical compositions of the present invention further comprise one or more additional therapeutically active ingredients (e.g., chemotherapeutic and/or palliative). For purposes of the invention, the term "palliative" refers to treatment that is focused on the relief of symptoms of a disease and/or side effects of a therapeutic regimen, but is not curative. For example, palliative treatment encompasses painkillers, antinausea medications, anti-pyretics, and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

Additionally, the present invention provides pharmaceutically acceptable derivatives of the inventive compounds, and methods of treating a subject using these compounds, pharmaceutical compositions thereof, or either of these in combination with one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

Research Uses, Pharmaceutical Uses and Methods of Treatment

Research Uses

According to the present invention, the inventive compounds may be assayed in any of the available assays known in the art for identifying compounds having antiprotozoal, HDAC inhibitory, TDAC inhibitory, aggresome inhibitory, and/or antiproliferative activity. For example, the assay may be cellular or non-cellular, in vivo or in vitro, high- or low-throughput format, etc.

Thus, in one aspect, compounds of this invention which are of particular interest include those which:

exhibit HDAC-inhibitory activity;
exhibit TDAC-inhibitory activity;
exhibit HDAC Class I inhibitory activity (e.g., HDAC1, HDAC2, HDAC3, HDAC8);
exhibit HDAC Class II inhibitory activity (e.g., HDAC4, HDAC5, HDAC6, HDAC7, HDAC9a, HDAC9b, HDRP/HDAC9c, HDAC10);
exhibit HDAC Class IV inhibitory activity;
exhibit the ability to inhibit HDAC1 (Genbank Accession No. NP_004955, incorporated herein by reference);
exhibit the ability to inhibit HDAC2 (Genbank Accession No. NP_001518, incorporated herein by reference);
exhibit the ability to inhibit HDAC3 (Genbank Accession No. O15739, incorporated herein by reference);
exhibit the ability to inhibit HDAC4 (Genbank Accession No. AAD29046, incorporated herein by reference);
exhibit the ability to inhibit HDAC5 (Genbank Accession No. NP_005465, incorporated herein by reference);
exhibit the ability to inhibit HDAC6 (Genbank Accession No. NP_006035, incorporated herein by reference);
exhibit the ability to inhibit HDAC7 (Genbank Accession No. AAP63491, incorporated herein by reference);
exhibit the ability to inhibit HDAC8 (Genbank Accession No. AAF73428, NM_018486, AF245664, AF230097, each of which is incorporated herein by reference);
exhibit the ability to inhibit HDAC9 (Genbank Accession No. NM_178425, NM_178423, NM_058176, NM_014707, BC111735, NM_058177, each of which is incorporated herein by reference)
exhibit the ability to inhibit HDAC10 (Genbank Accession No. NM_032019, incorporated herein by reference)
exhibit the ability to inhibit HDAC11 (Genbank Accession No. BC009676, incorporated herein by reference);
exhibit the ability to modulate the glucose-sensitive subset of genes downstream of Ure2p;
exhibit the ability to inhibit the degradation of protein by the aggresome;
exhibit cytotoxic or growth inhibitory effect on cancer cell lines maintained in vitro or in animal studies using a scientifically acceptable cancer cell xenograft model; and/or
exhibit a therapeutic profile (e.g., optimum safety and curative effect) that is superior to existing chemotherapeutic agents.

As detailed in the exemplification herein, in assays to determine the ability of compounds to inhibit cancer cell growth certain inventive compounds may exhibit $IC_{50}$ values $\leq 100$ µM. In certain other embodiments, inventive compounds exhibit $IC_{50}$ values $\leq 50$ µM. In certain other embodiments, inventive compounds exhibit $IC_{50}$ values $\leq 40$ µM. In certain other embodiments, inventive compounds exhibit $IC_{50}$ values $\leq 30$ µM. In certain other embodiments, inventive compounds exhibit $IC_{50}$ values $\leq 20$ µM. In certain other embodiments, inventive compounds exhibit $IC_{50}$ values $\leq 10$ µM. In certain other embodiments, inventive compounds exhibit $IC_{50}$ values $\leq 7.5$ µM. In certain embodiments, inventive compounds exhibit $IC_{50}$ values $\leq 5$ µM. In certain other embodiments, inventive compounds exhibit $IC_{50}$ values $\leq 2.5$ µM. In certain embodiments, inventive compounds exhibit $IC_{50}$ values $\leq 1$ µM. In certain embodiments, inventive compounds exhibit $IC_{50}$ values $\leq 0.75$ µM. In certain embodiments, inventive compounds exhibit $IC_{50}$ values $\leq 0.5$ µM. In certain embodiments, inventive compounds exhibit $IC_{50}$ values $\leq 0.25$ µM. In certain embodiments, inventive compounds exhibit $IC_{50}$ values $\leq 0.1$ µM. In certain other embodiments, inventive compounds exhibit $IC_{50}$ values $\leq 75$ nM. In certain other embodiments, inventive compounds exhibit $IC_{50}$ values $\leq 50$ nM. In certain other embodiments, inventive compounds exhibit $IC_{50}$ values $\leq 25$ nM. In certain other embodiments, inventive compounds exhibit $IC_{50}$ values $\leq 10$ nM. In other embodiments, exemplary compounds exhibited $IC_{50}$ values $\leq 7.5$ nM. In other embodiments, exemplary compounds exhibited $IC_{50}$ values $\leq 5$ nM.

Pharmaceutical Uses and Methods of Treatment

In general, methods of using the compounds of the present invention comprise administering to a subject in need thereof a therapeutically effective amount of a compound of the present invention. As discussed above, the compounds of the invention are selective inhibitors of histone deacetylases and, as such, are useful in the treatment of disorders modulated by histone deacetylases. As discussed above, the compounds of the invention are selective inhibitors of tubulin deacetylases and, as such, are useful in the treatment of disorders modulated by tubulin deacetylases. For example, compounds of the invention may be useful in the treatment of cancer (e.g., breast cancer, prostate cancer, multiple myeloma, leukemia, lymphoma, etc.). Accordingly, in yet another aspect, according to the methods of treatment of the present invention, tumor cells are killed, or their growth is inhibited by contacting said tumor cells with an inventive compound or composition, as described herein.

Thus, in another aspect of the invention, methods for the treatment of cancer are provided comprising administering a therapeutically effective amount of an inventive compound, as described herein, to a subject in need thereof. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like.

In certain embodiments, the method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer (including, but not limited to, glioblastoma, retinoblastoma, breast cancer, cervical cancer, colon and rectal cancer, leukemia (e.g., CML, AML, CLL, ALL), lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer).

In certain embodiments, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors.

In certain embodiments, the inventive compounds also find use in the prevention of restenosis of blood vessels subject to traumas such as angioplasty and stenting. For example, it is contemplated that the compounds of the invention will be useful as a coating for implanted medical devices, such as tubings, shunts, catheters, artificial implants, pins, electrical implants such as pacemakers, and especially for arterial or venous stents, including balloon-expandable stents. In certain embodiments inventive compounds may be bound to an implantable medical device, or alternatively, may be passively adsorbed to the surface of the implantable device. In certain other embodiments, the inventive compounds may be formulated to be contained within, or, adapted to release by a surgical or medical device or implant, such as, for example, stents, sutures, indwelling catheters, prosthesis, and the like. For example, drugs having antiproliferative and anti-inflammatory activities have been evaluated as stent coatings, and have shown promise in preventing restenosis (See, for example, Presbitero P. et al., "Drug eluting stents do they make the difference?", *Minerva Cardioangiol,* 2002, 50(5): 431-442; Ruygrok P. N. et al., "Rapamycin in cardiovascular medicine", *Intern. Med. J.,* 2003, 33(3):103-109; and Marx S. O. et al., "Bench to bedside: the development of rapamycin and its application to stent restenosis", *Circulation,* 2001, 104(8):852-855, each of these references is incorporated herein by reference in its entirety). Accordingly, without wishing to be bound to any particular theory, Applicant proposes that inventive compounds having antiproliferative effects can be used as stent coatings and/or in stent drug delivery devices, inter alia for the prevention of restenosis or reduction of restenosis rate. Suitable coatings and the general preparation of coated implantable devices are described in U.S. Pat. Nos. 6,099,562; 5,886,026; and 5,304,121; each of which is incorporated herein by reference. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. A variety of compositions and methods related to stent coating and/or local stent drug delivery for preventing restenosis are known in the art (see, for example, U.S. Pat. Nos. 6,517,889; 6,273,913; 6,258,121; 6,251,136; 6,248,127; 6,231,600; 6,203,551; 6,153,252; 6,071,305; 5,891,507; 5,837,313 and published U.S. patent application No.: US2001/0027340, each of which is incorporated herein by reference in its entirety). For example, stents may be coated with polymer-drug conjugates by dipping the stent in polymer-drug solution or spraying the stent with such a solution. In certain embodiment, suitable materials for the implantable device include biocompatible and nontoxic materials, and may be chosen from the metals such as nickel-titanium alloys, steel, or biocompatible polymers, hydrogels, polyurethanes, polyethylenes, ethylenevinyl acetate copolymers, etc. In certain embodiments, the inventive compound is coated onto a stent for insertion into an artery or vein following balloon angioplasty.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Within other aspects of the present invention, methods are provided for expanding the lumen of a body passageway, comprising inserting a stent into the passageway, the stent having a generally tubular structure, the surface of the structure being coated with (or otherwise adapted to release) an inventive compound or composition, such that the passageway is expanded. In certain embodiments, the lumen of a body passageway is expanded in order to eliminate a biliary, gastrointestinal, esophageal, tracheal/bronchial, urethral and/or vascular obstruction.

Methods for eliminating biliary, gastrointestinal, esophageal, tracheal/bronchial, urethral and/or vascular obstructions using stents are known in the art. The skilled practitioner will know how to adapt these methods in practicing the present invention. For example, guidance can be found in U.S. Patent Publication No.: 2003/0004209 in paragraphs [0146]-[0155], which paragraphs are hereby incorporated herein by reference.

Another aspect of the invention relates to a method for inhibiting the growth of multidrug resistant cells in a biological sample or a patient, which method comprises administering to the patient, or contacting said biological sample with a compound of the invention or a composition comprising said compound.

Additionally, the present invention provides pharmaceutically acceptable derivatives of the inventive compounds, and methods of treating a subject using these compounds, pharmaceutical compositions thereof, or either of these in combination with one or more additional therapeutic agents.

Another aspect of the invention relates to a method of treating or lessening the severity of a disease or condition associated with a proliferation disorder in a patient, said method comprising a step of administering to said patient, a compound of formula I or a composition comprising said compound.

It will be appreciated that the compounds and compositions, according to the method of the present invention, may be administered using any amount and any route of administration effective for the treatment of cancer and/or disorders associated with cell hyperproliferation. For example, when using the inventive compounds for the treatment of cancer, the expression "effective amount" as used herein, refers to a sufficient amount of agent to inhibit cell proliferation, or refers to a sufficient amount to reduce the effects of cancer. The exact amount required will vary from subject to subject, depending on the species, age, and general condition of the subject, the severity of the diseases, the particular anticancer agent, its mode of administration, and the like.

The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

Another aspect of the invention relates to a method for inhibiting histone deacetylase activity in a biological sample or a patient, which method comprises administering to the patient, or contacting said biological sample with a compound of formula I or a composition comprising said compound.

Furthermore, after formulation with an appropriate pharmaceutically acceptable carrier in a desired dosage, the pharmaceutical compositions of this invention, can be administered to humans and other animals orally, rectally, parenterally, intracisternally, intravaginally, intraperitoneally, topically (as by powders, ointments, creams or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art. The following examples contain important additional information, exemplification and guidance which can be adapted to the practice of this invention in its various embodiments and the equivalents thereof.

These and other aspects of the present invention will be further appreciated upon consideration of the following Examples, which are intended to illustrate certain particular embodiments of the invention but are not intended to limit its scope, as defined by the claims.

EXAMPLES

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

Example 1

Synthetic Methods

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of a variety combinatorial techniques, parallel synthesis and/or solid phase synthetic methods such as those discussed in detail below may be used. Alternatively or additionally, the inventive compounds may be prepared using any of a variety of solution phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

Example 2

Biological Assay Procedures

Cell culture and Transfections. TAg-Jurkat cells were transfected by electroporation with 5 µg of FLAG-epitope-tagged pBJ5 constructs for expression of recombinant proteins. Cells were harvested 48 h posttransfection.

HDAC assays. [$^3$H]Acetate-incorporated histones were isolated from butyrate-treated HeLa cells by hydroxyapatite chromatography (as described in Tong, et al. *Nature* 1997, 395, 917-921) Immunoprecipitates were incubated with 1.4 µg (10,000 dpm) histones for 3 h at 37° C. HDAC activity was determined by scintillation counting of the ethyl acetate-soluble [$^3$H]acetic acid (as described in Taunton, et al., *Science* 1996, 272, 408-411). Compounds were added in DMSO such that final assay concentrations were 1% DMSO. $IC_{50}$s were calculated using Prism 3.0 software. Curve fitting was done without constraints using the program's Sigmoidal-Dose Response parameters. All data points were acquired in duplicate and IC50s are calculated from the composite results of at least two separate experiments.

Example 3

In Vivo Activity

Although a variety of methods can be utilized, one exemplary method by which the in vivo activity of the inventive compounds is determined is by subcutaneously transplanting a desired tumor mass in mice. Drug treatment is then initiated when tumor mass reaches approximately 100 mm$^{-3}$ after transplantation of the tumor mass. A suitable composition, as described in more detail above, is then administered to the mice, preferably in saline and also preferably administered once a day at doses of 5, 10 and 25 mg/kg, although it will be appreciated that other doses can also be administered. Body weight and tumor size are then measured daily and changes in percent ratio to initial values are plotted. In cases where the transplanted tumor ulcerates, the weight loss exceeds 25-30% of control weight loss, the tumor weight reaches 10% of the body weight of the cancer-bearing mouse, or the cancer-bearing mouse is dying, the animal is sacrificed in accordance with guidelines for animal welfare.

Example 4

Assays to Identify Potential Antiprotozoal Compounds by Inhibition of Histone Deacetylase As detailed in U.S. Pat. No. 6,068,987, incorporated herein by reference, inhibitors of histone deacetylases may also be useful as antiprotozoal agents. Described therein are assays for histone deacetylase activity and inhibition and describe a variety of known protozoal diseases. The entire contents of U.S. Pat. No. 6,068,987 are hereby incorporated by reference.

Example 5

High-Throughput Immunofluorescence Assay

Compounds of the invention are tested from their HDAC or TDAC specificity using a high-throughput immunofluorescence-based assay. The assay is based on the use of specific antibodies for acetylated tubulin and acetylated lysine (i.e., a marker for acetylated histones).

Cells (e.g., 293T cells) are incubated the inventive compound over a test range of concentrations after the cells have been allowed to adhere to the cell culture plate overnight. After a determined time of incubation with the inventive compound (e.g., 6-8 hours), the cells are treated with a first primary antibody directed against acetylated tubulin and a second primary antibody directed against acetylated lysine. The cells are then contacted with two secondary antibodies specific for each of the primary antibodies and identifiable by a unique fluorescent signal.

The plates are then imaged, and the fluorescence signal from each of the secondary antibodies is quantitated. The data gathered is then used to calculate dose-response curves, to calculate $IC_{50}$ values, to establish structure-function relationships, to calculate the ratio of HDAC to TDAC inhibition, and to determine the specificity for HDAC or TDAC.

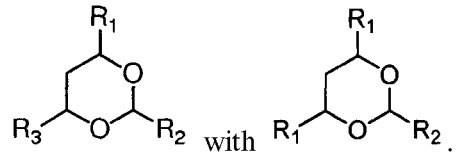

What is claimed is:

1. A compound of the formula:

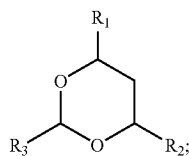

wherein
$R_1$ is

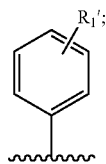

$R_1'$ is

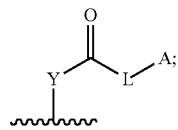

Y is NH;
L is a substituted or unsubstituted, cyclic or acyclic, branched or unbranched aliphatic moiety; a substituted or unsubstituted, cyclic or acyclic, branched or unbranched heteroaliphatic moiety; a substituted or unsubstituted aryl moiety; a substituted or unsubstituted heteroaryl moiety; or a cyclic ring system, wherein the rings may be aryl, heteroaryl, non-aromatic carbocyclic, or non-aromatic heterocyclic;

A comprises a functional group selected from the group consisting of:

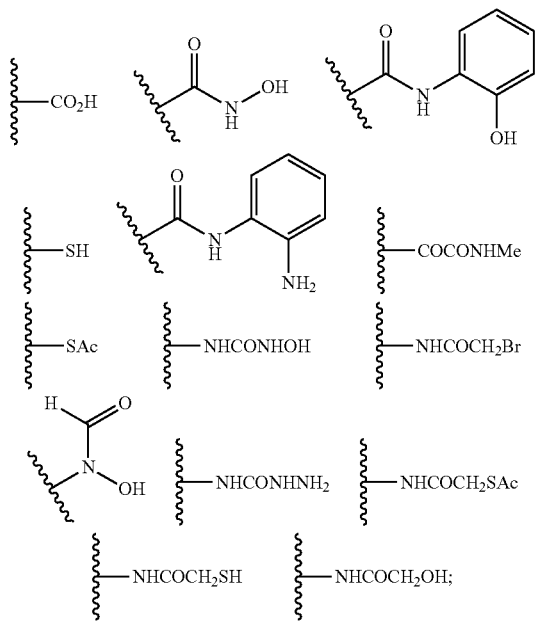

$R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_B$; —$C(=O)R_B$; —$CO_2R_B$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and $R_3$ is

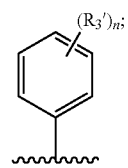

wherein n is an integer between 1 and 5, inclusive; and each occurrence of $R_3'$ is independently hydrogen; halogen; cyclic or acyclic, substituted or unsubstituted, branched or unbranched aliphatic; substituted or unsubstituted, branched or unbranched acyl; substituted or unsubstitued, branched or unbranched aryl; substituted or unsubstituted, branched or unbranched heteroaryl; —$OR_C$; —$C(=O)R_C$; —$CO_2R_C$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently hydrogen; a protecting group; alkyl; alkenyl; alkynyl; acyl; aryl;

heteroaryl; alkoxy; aryloxy; alkylthio; arylthio; amino, alkylamino, dialkylamino, heteroaryloxy; or heteroarylthio;

or a pharmaceutically acceptable salt thereof.

2. The compound of claim 1, wherein the compound is of one of the formulae:

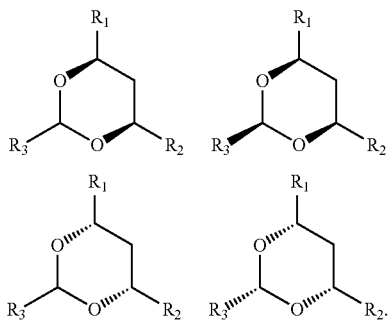

3. The compound of claim 1, wherein $R_1$ is of the formula:

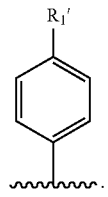

4. The compound of claim 1, wherein $R_1'$ is

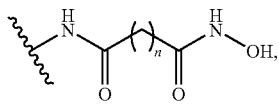

wherein n is an integer between 0 and 15, inclusive.

5. The compound of claim 4, wherein n is 5 or 6.

6. The compound of claim 1 wherein $R_2$, is of the formula:

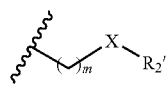

wherein m is an integer between 0 and 8, inclusive; preferably, between 1 and 6, inclusive;

X is O, S, $CH_2$, NH, or $NR_2'$; and $R_2'$ is aliphatic, heteroaliphatic, acyl, substituted or unsubstituted aryl, or substituted or unsubstituted heteroaryl.

7. The compound of claim 6, wherein X is O.

8. The compound of claim 6, wherein X is S.

9. The compound of claim 6, wherein m is 1.

10. The compound of claim 6, wherein $R_2'$ is substiuted or unsubstituted heteroaryl.

11. The compound of claim 1, wherein $R_2$ is selected from the group consisting of:

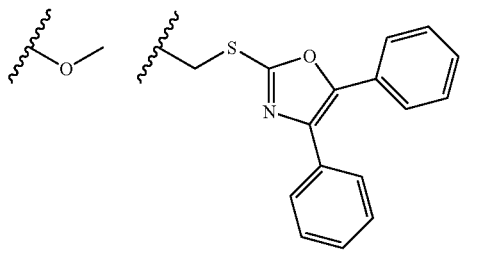

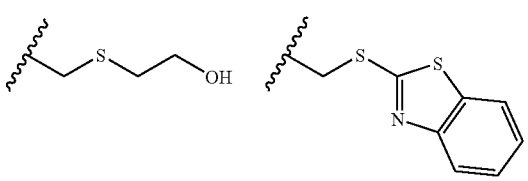

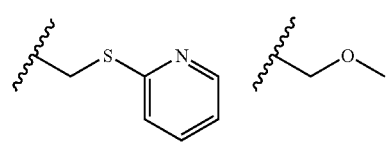

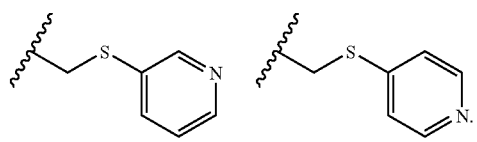

12. The compound of claim 1, wherein $R_2$ is selected from the group consisting of:

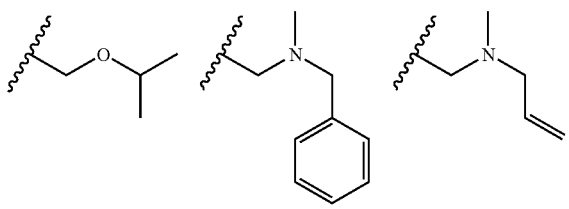

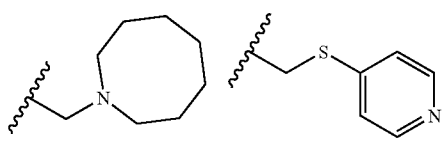

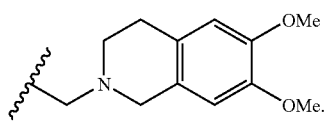

13. The compound of claim 1, wherein R₂ is

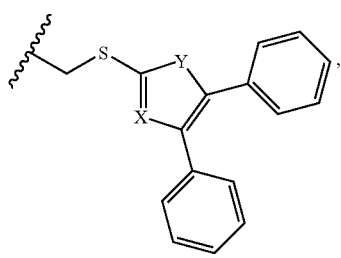

wherein X is N, and Y is NH, S, or O.

14. The compound of claim 1, wherein R₂ is

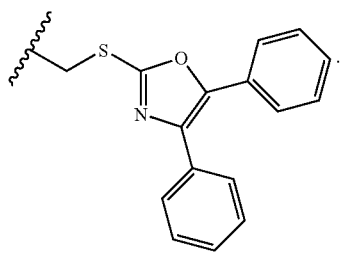

15. The compound of claim 1, wherein R₃ is an unsubstituted phenyl moiety.

16. The compound of claim 1 of the formula:

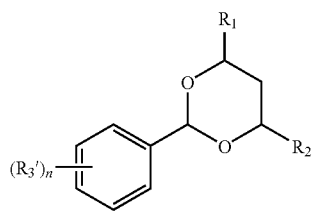

wherein n is an integer between 1 and 5, inclusive; and each occurrence of R₃' is independently halogen, hydroxyl, protected hydroxyl, alkoxy, amino, alkylamino, dialkylamino, —CN, —SCN, —NO₂, $C_1$-$C_6$ alkyl, $C_2$-$C_6$ alkenyl, $C_2$-$C_6$ alkynyl, acyl, or haloalkyl.

17. The compound of claim 1 of the formula:

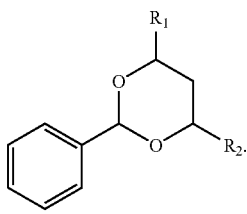

18. The compound of claim 1 selected from the group consisting of:

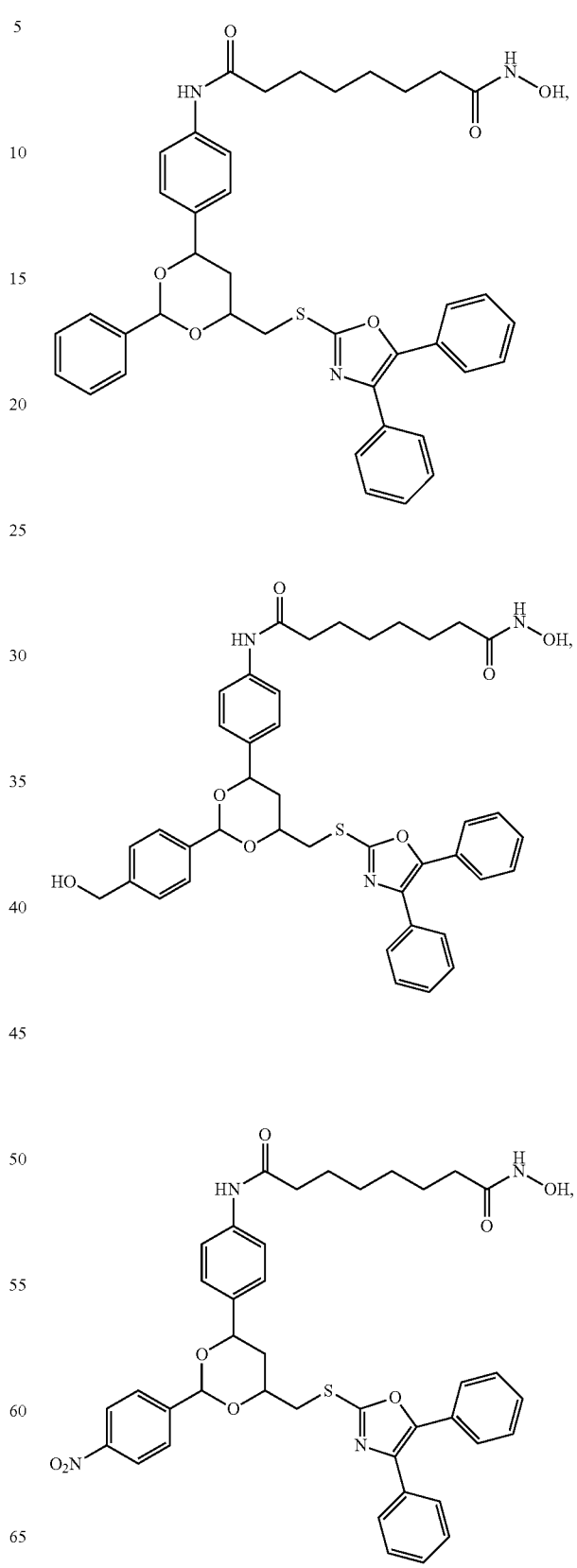

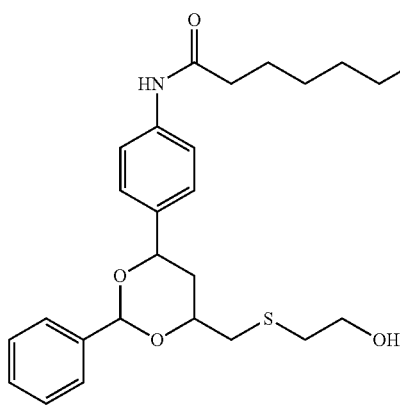
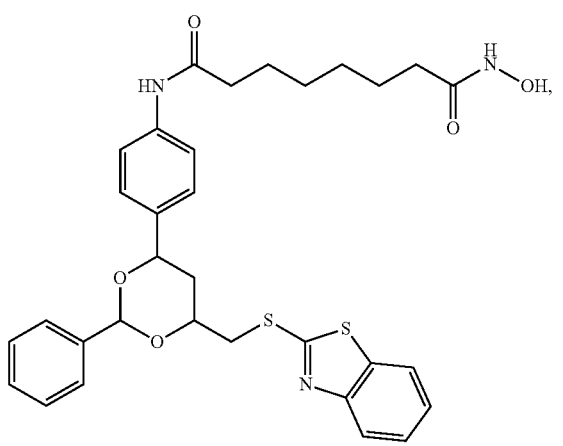
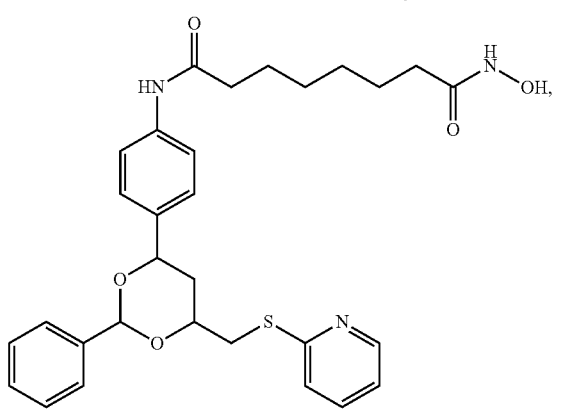
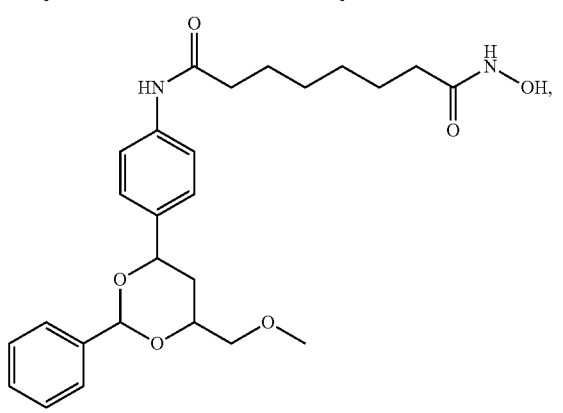
and
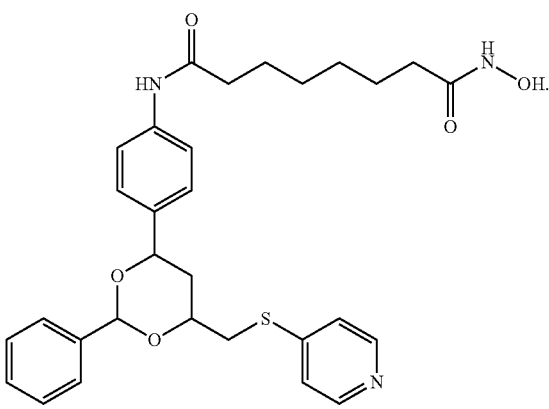
19. The compound of claim 1 of formula:
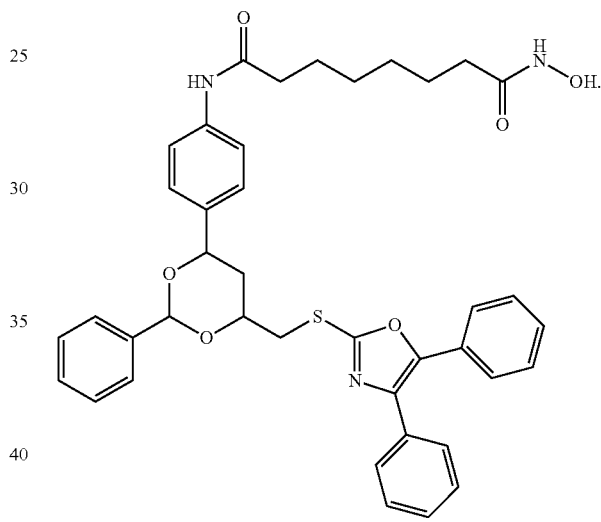
20. A compound of formula:
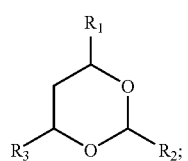
wherein
each occurrence of $R_1$ is independently
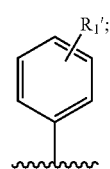

each occurrence of $R_1'$ is independently

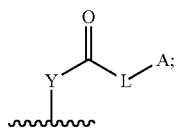

each occurrence of Y is independently NH or O;
each occurrence of L is independently a substituted or unsubstituted, cyclic or acyclic, branched or unbranched aliphatic moiety; a substituted or unsubstituted, cyclic or acyclic, branched or unbranched heteroaliphatic moiety; a substituted or unsubstituted aryl moiety; a substituted or unsubstituted heteroaryl moiety; or a cyclic ring system, wherein the rings may be aryl, heteroaryl, non-aromatic carbocyclic, or non-aromatic heterocyclic;
each occurrence of A comprises a functional group selected from the group consisting of:

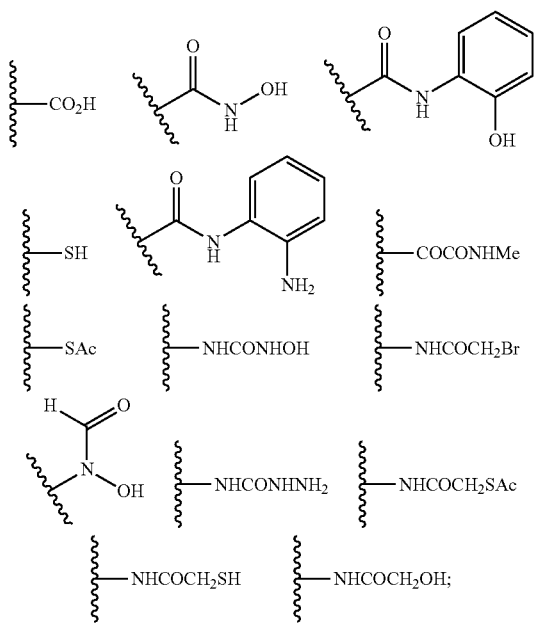

$R_2$ is —$R_1$; hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_B$; —$C(=O)R_B$; —$CO_2R_B$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; or a pharmaceutically acceptable salt thereof.

21. A pharmaceutical composition comprising a compound of claim 1 and a pharmaceutically acceptable excipient.

22. The pharmaceutical composition of claim 21 further comprising a cytotoxic agent.

23. The pharmaceutical composition of claim 21 further comprising a proteasome inhibitor.

24. The pharmaceutical composition of claim 23, wherein the proteasome inhibitor is bortezomib.

25. The pharmaceutical composition of claim 21 further comprising an aggresome inhibitor.

26. A method of inhibiting histone deacetylase, the method comprising steps of:
contacting a histone deacetylase with a compound of claim 1.

27. A method of inhibiting tubulin deacetylase, the method comprising steps of:
contacting a tubulin deacetylase with a compound of claim 1.

28. A method of inhibiting an aggresome, the method comprising steps of:
contacting a aggresome with a compound of claim 1.

29. The method of claim 26, wherein the histone deacetylase is purified.

30. The method of claim 26, wherein the histone deacetylase is in a cell.

31. The method of claim 26, wherein the histone deacetylase is HDAC6.

* * * * *

UNITED STATES PATENT AND TRADEMARK OFFICE
CERTIFICATE OF CORRECTION

PATENT NO. : 8,304,451 B2
APPLICATION NO. : 12/299430
DATED : November 6, 2012
INVENTOR(S) : Ralph Mazitschek et al.

It is certified that error appears in the above-identified patent and that said Letters Patent is hereby corrected as shown below:

*In the Drawings*

In Figure 3, please replace the following chemical structure:

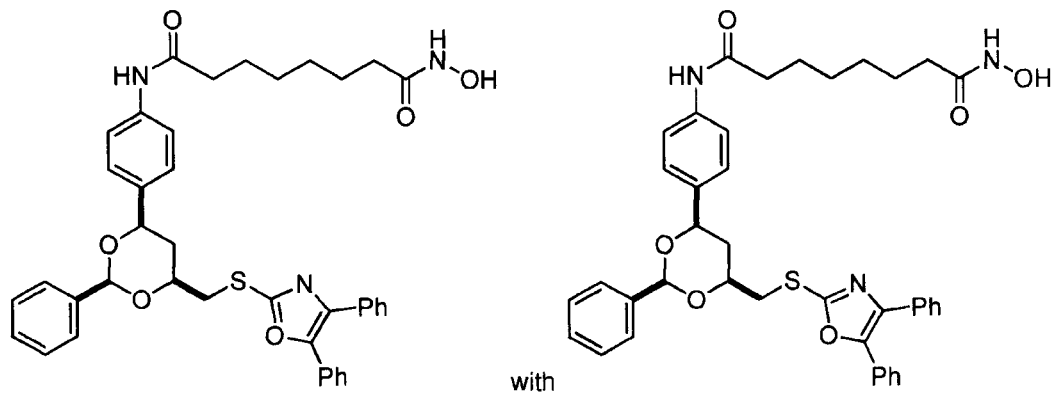

*In the Specification*

At column 31, lines 5-13, please replace the following chemical structure:

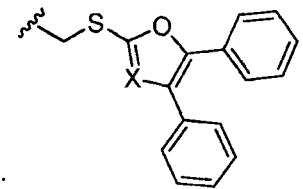

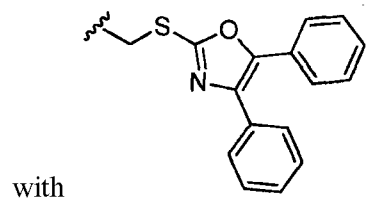

with

Signed and Sealed this
Nineteenth Day of February, 2013

Teresa Stanek Rea
*Acting Director of the United States Patent and Trademark Office*

CERTIFICATE OF CORRECTION (continued)

At column 45, lines 57-61, please replace Formula (jj): 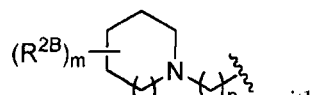 with

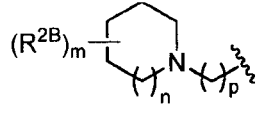
n = 0 or 1 .

At column 48, lines 1-9, please replace the following chemical structure: 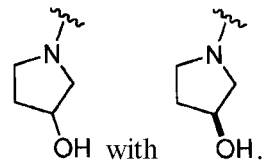 with 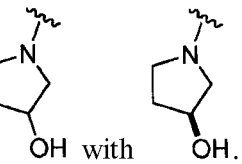.

At column 70, lines 37-42, please replace the following chemical structure: 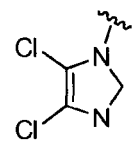 with

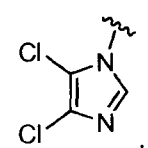 .

At column 81, lines 27-30, please replace Formula (kk): 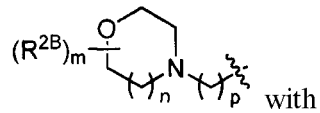 with

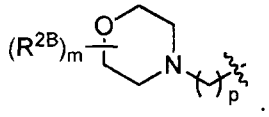 .

At column 84, lines 9-15, please replace the following chemical structure: 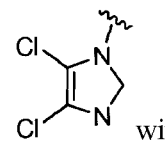 with

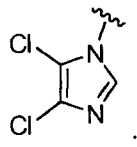 .

CERTIFICATE OF CORRECTION (continued)

U.S. Pat. No. 8,304,451 B2

*In the claims*

In claim 20, at column 120, lines 48-53, please replace the following chemical structure: